(12) United States Patent
Griffiths et al.

(10) Patent No.: US 9,193,678 B2
(45) Date of Patent: Nov. 24, 2015

(54) CHEMICAL AGENTS CAPABLE OF FORMING COVALENT 3-D NETWORKS

(75) Inventors: Jon-Paul Griffiths, Begbroke (GB); Michael Douglas Eason, Begbroke (GB); Sarah Louise Beal, Begbroke (GB); Sarah Vickers, Begbroke (GB); Richard Charles Wincewicz, Begbroke (GB); David Simon King, Begbroke (GB)

(73) Assignee: OXFORD ADVANCED SURFACES LTD, Yarnton (GB)

( * ) Notice: Subject to any disclaimer, the term of this patent is extended or adjusted under 35 U.S.C. 154(b) by 317 days.

(21) Appl. No.: 13/254,827

(22) PCT Filed: Mar. 2, 2010

(86) PCT No.: PCT/GB2010/000368
§ 371 (c)(1),
(2), (4) Date: Sep. 2, 2011

(87) PCT Pub. No.: WO2010/100410
PCT Pub. Date: Sep. 10, 2010

(65) Prior Publication Data
US 2012/0021223 A1    Jan. 26, 2012

(30) Foreign Application Priority Data

Mar. 2, 2009  (GB) .................................. 0903563.5
Aug. 21, 2009  (GB) .................................. 0914692.9

(51) Int. Cl.
*C08F 283/00*  (2006.01)
*C07C 311/49*  (2006.01)
*C08J 7/04*  (2006.01)

(52) U.S. Cl.
CPC ................. *C07C 311/49* (2013.01); *C08J 7/04* (2013.01); *Y10T 428/2998* (2015.01); *Y10T 428/31536* (2015.04)

(58) Field of Classification Search
USPC ............................................. 525/417, 333.5
See application file for complete search history.

(56) References Cited

U.S. PATENT DOCUMENTS 2,710,862 A   6/1955  Schroeder
3,226,381 A  12/1965  Breslow et al.
(Continued)

FOREIGN PATENT DOCUMENTS

CA          812736     5/1969
CN         1475471     2/2004
(Continued)

OTHER PUBLICATIONS

Itoh et al., preparation of oligodiazo compounds by using the suzuki coupling reaction and characterization of their photoproducts, JACS. 2004, 126, 1130-1140.*
(Continued)

*Primary Examiner* — Monique Peets
(74) *Attorney, Agent, or Firm* — Morrison & Foerster LLP

(57) ABSTRACT

The invention provides a functionalized compound of formula (II), which functionalized compound comprises n carbene precursor groups which are the same or different, wherein n is an integer equal to or greater than 3: wherein x is 1, E is a group which is capable of being converted into a carbene reactive intermediate group, Q is a core moiety, a polymer or a dendrimer, and each of the [R]$_x$-E-L- groups, which are the same or different, is independently selected from a group of formula (Ie) and a group of formula (Ia): wherein L is a single bond or a linker group as defined herein, R is a terminal group as defined herein, and R$^1$ is as defined herein. Further provided is the use of the functionalized compound as an agent for producing a chemically-bound three-dimensional network on or within a substrate. Processes for producing the following products using the functionalized compounds of the invention are also provided, as are the resulting products: a chemically-bound three-dimensional network on or within a substrate; a chemically-bound three-dimensional network between a first substrate and a second substrate; a film or a coating; a coated substrate; a product which comprises a first substrate, a second substrate and a composition at an interface of the first and second substrates; a treated particle. The invention further provides a process for cross linking a first substrate to a second substrate, using a functionalized compound of the invention, and the resulting cross-linked product. The invention also provides a process for producing the functionalized compounds of the invention.

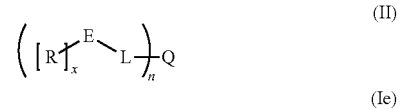

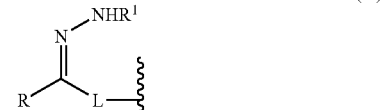

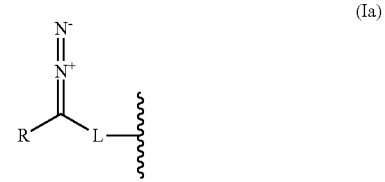

16 Claims, 6 Drawing Sheets

(56) References Cited

U.S. PATENT DOCUMENTS

| | | | |
|---|---|---|---|
| 3,376,278 | A | 4/1968 | Morgan et al. |
| 3,796,754 | A | 3/1974 | Shindo et al. |
| 3,838,117 | A | 9/1974 | Shindo et al. |
| 3,852,256 | A | 12/1974 | Parker et al. |
| 4,010,226 | A | 3/1977 | Crossland et al. |
| 4,280,819 | A | 7/1981 | Hartle et al. |
| 4,309,427 | A | 1/1982 | Lombardino |
| 4,309,453 | A | 1/1982 | Reiner et al. |
| 4,391,949 | A | 7/1983 | St. Clair |
| 4,444,953 | A | 4/1984 | St. Clair |
| 4,556,464 | A | 12/1985 | St. Clair |
| 5,002,582 | A | 3/1991 | Guire et al. |
| 5,075,427 | A | 12/1991 | Kang et al. |
| 5,104,921 | A | 4/1992 | Erickson et al. |
| 5,124,405 | A | 6/1992 | Erickson |
| 5,154,808 | A | 10/1992 | Miyasaka et al. |
| 5,446,104 | A | 8/1995 | Handlin et al. |
| 5,490,983 | A | 2/1996 | Worley et al. |
| 6,060,046 | A | 5/2000 | Steinberg et al. |
| 6,110,936 | A | 8/2000 | Gravestock |
| 6,699,527 | B1 | 3/2004 | Moloney et al. |
| 7,034,129 | B2 | 4/2006 | Moloney et al. |
| 7,125,835 | B2 | 10/2006 | Bennett et al. |
| 7,294,612 | B2 | 11/2007 | Popplewell et al. |
| 7,939,581 | B2 | 5/2011 | Moloney et al. |
| 2003/0186448 | A1 | 10/2003 | Bourget et al. |
| 2004/0127691 | A1 | 7/2004 | Moloney et al. |
| 2005/0182148 | A1 | 8/2005 | Gaud et al. |
| 2006/0003260 | A1 | 1/2006 | Nakagawa et al. |
| 2006/0240358 | A1 | 10/2006 | Powell et al. |
| 2008/0146731 | A1 | 6/2008 | Moloney et al. |
| 2010/0068783 | A1 | 3/2010 | Moloney et al. |

FOREIGN PATENT DOCUMENTS

| | | |
|---|---|---|
| CN | 1518536 | 8/2004 |
| DE | 2216837 | 10/1972 |
| EP | 0014843 | 1/1980 |
| EP | 0177248 | 9/1987 |
| EP | 0227163 | 5/1992 |
| EP | 0425485 | 10/2000 |
| EP | 1533364 | 7/2008 |
| EP | 1916261 | 12/2010 |
| FR | 1500512 | 10/1966 |
| GB | 1344991 | 1/1974 |
| GB | 1344993 | 1/1974 |
| GB | 1412963 | 11/1975 |
| GB | 1482923 | 8/1977 |
| GB | 1529552 | 10/1978 |
| GB | 2013201 | 8/1979 |
| JP | 48097855 | 12/1973 |
| JP | 59212832 | 12/1984 |
| JP | 04031404 | 2/1992 |
| WO | WO-92/17436 | 10/1992 |
| WO | WO-95/19949 | 7/1995 |
| WO | WO-96/01294 | 1/1996 |
| WO | WO-99/01514 | 1/1999 |
| WO | WO-00/26180 | 5/2000 |
| WO | WO-01/58230 | 8/2001 |
| WO | WO-01/92344 | 12/2001 |
| WO | WO-02/32590 | 4/2002 |
| WO | WO-02/074430 | 9/2002 |
| WO | WO-2004/076511 | 9/2004 |
| WO | WO-2005/028423 | 3/2005 |
| WO | WO-2005/095507 | 10/2005 |
| WO | WO-2006/075183 | 7/2006 |
| WO | WO-2006/096221 | 9/2006 |
| WO | WO-2008/023170 | 2/2008 |
| WO | WO-2009/146018 | 12/2009 |

OTHER PUBLICATIONS

Iwamura et al., approaches to superparamagnetic polycarbenes and polynitrenes, molecular crystal and liquid crystals science and technology, section a 1992, 218, 207-212.*

Hirai et al., "A Dendrimer Approach to High-Spin Polycarbenes. Conversion of Connectivity from Disjoint to Non-Disjoint by Perturbation of Nonbonding Molecular Orbital Coefficients," Organic Letters (2006) 8(9):1847-1850.

International Preliminary Report on Patentability and Written Opinion of the International Searching Authority for International Application No. PCT/GB2010/000368, mailed Sep. 6, 2011, 8 pages.

International Search Report for International Application No. PCT/GB2010/000368, mailed Jun. 21, 2010, 4 pages.

Itoh et al., "Preparation of Oligodiazo Compounds by Using the Suzuki Coupling Reaction and Characterization of Their Photoproducts," Journal of the American Chemical Society (2004) 126:1130-1140.

Itoh et al., "Synthesis of Phenylacetylene Dendrimers Having Sterically Congested Diazo Units and Characterization of Their Photoproducts," European Journal of Organic Chemistry (2004):2991-3003.

Iwamura et al., "Approaches to Superparamagnetic Polycarbenes and Polynitriles," (1992) Database CA Chemical Abstracts Service, Accession No. 1992:532030.

Nakamura et al., "Novel Organic Ions of High-Spin States. 5. Generation of a High-Spin Ground-State Anion from an Intramolecularly Spin-Frustrated System," Journal of the American Chemical Society (1996) 118(36):8684-8687.

Tanaka et al., "Extremely .pi.-Delocalited Nature of Dianthrylcarbene-Based High Spin Systems as Studied by CW and Pulsed 2D Electron Spin Transient Mutation Spectroscopy," (2002) Chemical Abstracts Service Database CA Online Accession No. 2002:595968.

Tsuchiya et al., "A Tris (Carbene) Constructed with Stable Triplet Carbene Units," Bulletin of the Chemical Society of Japan (2005) 78:2037-2050.

U.S. Appl. No. 10/741,288, filed Jul. 2004, Moloney et al.
U.S. Appl. No. 11/795,253, filed Jun. 2008, Moloney et al.
U.S. Appl. No. 12/377,487, filed Mar. 2010, Moloney et al.

Anonymous (1998) "Water Treatment with Biocidal Polymers," Journal of Environmental Health 60(9):47-48.

Avent et al. (2000) "Synthesis and Electrochemical Behavior of [60]Fullerene Possessing Poly(arylacetylene) Dendrimer Addends," J. Chem. Soc. Perkins Trans. 2:1409-1414.

Bergbreiter et al. (1996) "New Approaches in Polymer Surface Modification," Journal of Plastic Film & Sheeting 12:15-26.

Bernier et al. (1990) "Polymer Surface Modification by Dual-Frequency Plasma Treatment," ACS Symposium Series 440:147-160.

Bhowmick and Inoue (1996) "Polymer-Polmer Adhesion in the Presence of Compatibilizer,"Journal of Adhesion 59:265-280.

Braybrook et al. (1993) "The Preparation and Reactivity of Some Photoactivable Reactive Dyes," J. Photochem. Photobiol A: Chem 70:171-178.

Brewis and Briggs (1981) "Adhesion to Polyethylene and Polypropylene," Polymer 22:7-16.

Bridgett et al. (1992) "Control of Staphylococcal Adhesion to Polystyrene Surfaces by Polymer Surface Modification with Surfactants," Biomaterials 13(7):411-416.

Carlsohn et al. (1983) "Biocide Polymere," Pharmazie 38:823-826 (English abstract).

Cellulose Tracetate—http://en.wikipedia.org/wiki/Triacetate accessed May 26, 2009.

Chan et al. (1996) "Polymer Surface Modification by Plasmas and Photons," Surface Science Reports 24:1-54.

Charbonnier et al. (2001) "Functionalization of Polymer Surfaces Using Excimer VUV Systems and Silent Discharges. Application to Electroless Metallization," Journal of Adhesion 75(4):381-404.

Chiriac (2001) "The Improvement of Adhesive Character of an Acrylovinylic Macromolecular Compound," Polymer Testing 20:873-877.

Choi et al. (2005) Characteristics of Atmospheric Pressure N2 Cold Plasma Torch Using 60-Hz AC Power and its Application to Polymer Surface Modification,: Surface & Coatings Technology 193:319-324.

Cole and Macosko (2000) "Polymer-Polymer Adhesion in Melt-Processed Layered Structures," Journal of Plastic Film & Sheeting 16:213-222.

(56) References Cited

OTHER PUBLICATIONS

Crosby (2003) "Combinatorial Characterization of Polymer Adhesion," Journal of Materials Science 38:4439-4449.
Crosby et al. (2005) "Controlling Polymer Adhesion with Pancakes," Langmuir 21:11738-11743.
Davies (2004) "Understanding Biofilm Resistance to Antibacterial Agents," Nature 2:114-122.
Delmar-Greenberg et al. (2003) "Polymer Surface Modification for Cell Adhesion," Abstracts of Papers of the American Chemical Society 325:U579.
Dhayal et al. (2006) "Using Fast Atomic Source and Low-Energy Plasma Ions for Polymer Surface Modification," Vacuum 80:643-646.
Eknoian and Worley (1998) "New N-Halamine Biocidal Polymers," Journal of Bioactive and Compatible Polymers 13:303-314.
Elrod and Worley (1999) "Synthesis of Novel N-Halamine Biocidal Polymers," Journal of Bioactive and Compatible Polymers 14:258-269.
Felton and McGinity (1999) "Adhesion of Polymeric Films to Pharmaceutical Solids," European Journal of Pharmaceutics and Biopharmaceutics 47:3-14.
Fourche (1995) "An Overview of the Basic Aspects of Polymer Adhesion. Part 1: Fundamentals," Polymer Engineering and Science 35:957-967.
Fourche (1995) "An Overview of the Basic Aspects of Polymer Adhesion. Part II: Application to Surface Treatments," Polymer Engineering and Science 35(12):968-975.
Friedrich et al. (2003) "Polymer Surface Modification with Monofunctional Groups of Variable Types and Densities," Journal of Adhesion Science and Technology 17(12):1591-1617.
Ginn and Steinbock (2003) "Polymer Surface Modification Using Microwave-Oven-Generated Plasma," Langmuir 19:8117-8118.
Griessner and Hodgkin (1988) "Biopolymer Surface Modification Using Plasma Grafting," Biomaterials 9:292.
Guo et al. (2006) "Chemoresponsive Monolayer Transistors," PNAS 103(31):11452-11456.
Guzman et al. (1998) "Polymer Surface Modification by Ion Implantation and Reactive Deposition of Transparent Films," Surface & Coatings Technology 104:375-379.
Hazziza-Laskar et al. (1993) "Biocidal Polymers Active by Contact. I. Synthesis of Polybutadiene with Pendant Quaternary Ammonium Groups," Journal of Applied Polymer Science 50:651-662.
Hazziza-Laskar et al. (1995) "Biocidal Polymers Active by Contact. IV. Polyurethanes Based on Polysiloxanes with Pendant Primary Alcohols and Quarternary Ammonium Groups," Journal of Applied Polymer Science 58:77-84.
Herrero et al. (2006) "Bacterial Adhesion to Poly (Vinyl Chloride) Films: Effect of Chemical Modification and Water Induced Surface Reconstruction," Journal of Adhesion Science and Technology 20:183-195.
Hünig et al. (2002) "Electrochromics by Intramolecular Redox Switching of Single Bonds," European Journal of Organic Chemistry 10:1603-1613.
Ikada (1994) "Surface Modification of Polymers for Medical Applications," Biomaterials 15(10):725-736.
International Search Report issued for International Patent Application No. PCT/GB2007/003194, dated Oct. 6, 1997, 3 pages.
Jansen and Kohnen (1995) "Prevention of Biofilm Formation by Polymer Modification," Journal of Industrial Microbiology 15:391-396.
Kato et al. (2003) Polymer Surface with Graft Chains, Progress in Polymer Science 28:209-259.
Kirmse and Homberger (1991) "Intramolecular Addition Reactions of Functionalized Arylcarbenes to Double Bonds," Journal of the American Chemical Society 113:3925-3934.
Kirmse and Kund (1990) "Carbenes and the O—H Bond: Hydroxyalkyl-Substituted Arylcarbenes," Journal of Organic Chemistry 55:2325-2332.
Kirmse and Özkir (1992) "Intramolecular Hydrogen Abstraction by Functionalized Arylcarbenes," Journal of the American Chemical Society 114:7590-7591.
Kizlink et al. (1996) "Evolutional Organotin Compounds for Biocidal Wood Protection Suitable for Small Tonnage Production," Drevarsky Vyskum 41(2):19-29.
Koberstein et al. (1998) "Creating Smart Polymer Surfaces with Selective Adhesion Properties," The Journal of Adhesion 66:229-249.
Krishnan et al. (1988) "Reactions of Hydroxybenzophenone with Hydrazines," Journal of Heterocyclic Chemistry 25(2):447-452.
Laurens and Petit (2003) "Modifications Induites en Surface de Polymeres par Traitement Laser," Annales De Chimie-Science Des Materiaux 28:67-80. (English abstract).
Lee and Wool (2000) "Polymer Adhesion vs. Substrate Receptor Group Density," Macromolecules 33:2680-2687.
Lin et al. (2002) "Bactericidal Properties of Flat Surfaces and Nanoparticles Derivatized with Alkylated Polyethylenimines," Biotechnology Progress 18:1082-1086.
Lin et al. (2002) "Insights into Bactericidal Action of Surface-Attached Poly(vinyl-N-hexylpyridinium) Chains," Biotechnology Letters 24:801-805.
Lin et al. (2003) "Mechanism of Bactericidal and Fungicidal Activities of Textiles Covalently Modified with Alkylated Polyethylenimine," Biotechnology Bioengineering 83:168-172.
Liu et al. (2004) "Effects of DBD Plasma Operating Parameters on the Polymer Surface Modification," Surface & Coatings Technology 185:311-320.
Maeda et al. (2002) "Adhesion and Friction Mechanisms of Polymer-on-Polymer Surfaces," Science 297:379-382.
Makioka et al. (1996) "Synthetic Utility of Umpoled Diaryl Thioketone-Lanthanoid Intermediates: Desulfurization, Cross Coupling with Electrophiles, and Desulfurizative Homocoupling," Journal of Organic Chemistry 61:372-375.
Neamtu et al. (1999) "Acrylovinylic Macromolecular Compounds with Adhesive Properties," Polymer Testing 18:415-427.
Nurdin et al. (1993) "Biocidal Polymers Active by Contact. II. Biological Evaluation of Polyurethane Coatings with Pendant Quaternary Ammonium Salts," Journal of Applied Polymer Science 50:663-670.
Nurdin et al. (1993) "Biocidal Polymers Active by Contact. III. Ageing of Biocidal Polyurethane Coatings in Water," Journal of Applied Polymer Science 50:671-678.
Official Action issued for Chinese Patent Application No. 200780037974.5, dated Jun. 29, 2011, 10 pages.
Official Action issued for U.S. Appl. No. 12/377,487, dated Aug. 29, 2012, 9 pages.
Ozdemir and Sadikoglu (1998) "A New and Emerging Technology: Laser-Induced Surface Modification of Polymers," Trends in Food Science & Technology 9:159-167.
Ozdemir et al. (1999) "Physical Polymer Surface Modfiication Methods and Applications in Food Packaging Polymers," Critical Reviews in Food Science and Nutrition 39:457-477.
Packham (2003) "Surface Energy, Surface Topography and Adhesion," International Journal of Adhesion and Adhesives 23:437-448.
Pappas et al. (1991) "Studies of Adhesion of Metal Films to Polyimide," Journal of Vacuum Science & Technology 9:2704-2708.
Ranucci et al. (2001) "Improved Polyimide/Metal Adhesion by Chemical Modification Approaches," Journal of Applied Polymer Science 82:1971-1985.
Rudoy and Ogarev (1991) "Modification of Polymer Surface Properties by Inert and Reactive Surface-Active compounds," Makromolekulare Chemie-Macromolecular Symposia 44:303-315.
Ruhmann and Wentrup (1994) "Synthesis of a Photoactivatable 9-Z-Oleic Acid for Protein Kinase C Labeling," Tetrahedron 50(12):3785-3796.
Sancaktar (1993) "Polymer Adhesion by Ultrasonic Welding," Journal of Adhesion Science and Technology 13(2):179-201.
Sartomer Application Bulletin (2005) "Adhesion of Radiation Cured Coatings to Plastics," 4025:1-7.
Sauvet et al. (2000) "Biocidal Polymers Active by Contact. V. Synthesis of Polysiloxanes with Biocidal Activity," Journal of Applied Polymer Science 75:1005-1012.

(56) References Cited

OTHER PUBLICATIONS

Shao et al. (2004) "Synthesis and Surface Antimicrobial Activity of a Novel Perfluorooctylated Quarternary Ammonium Silane Coupling Agent," Journal of Fluorine Chemistry 125:721-724.
Shi et al. (2004) "Surface-Grafted Viologen for Precipitation of Silver Nanoparticles and Their Combined Bactericidal Activities," Langmuir 20:6847-6852.
Shin et al. (2002) "Preparation of Plastic and Biopolymer Multilayer Films by Plasma Source Ion Implantation," Journal of Agricultural and Food Chemistry 50:4608-4614.
Siau et al. (2006) "Epoxy Polymer Surface Modification Through Wet-Chemical Organic Surface Synthesis for Adhesion Improvement in Microelectronics," Thin Solid Films 495:348-356.
Sofia and Merrill (1998) "Grafting of PEO to Polymer Surfaces Using Electron Beam Irradiation," Journal of Biomedical Materials Research 40:153-163.
Sun and Williams (1999) "Dressing to Kill," Chemistry & Industry 658-661.
Sun and Xu (1998) "Durable and Regenerable Antibacterial Finishing of Fabrics: Biocidal Properties," Textile Chemist and Colorist 30(6):26-30.
Sun and Xu (1999) "Durable and Regenerable Antibacterial Finishing of Fabrics: Chemical Structures," Textile Chemist and Colorist 31-37.
Sun et al. (1995) "Disinfection of Water by N-Halamine Biocidal Polymers," Industrial & Engineering Chemistry Research 34:4106-4109.
Sun et al. (1999) "New-Type Sulphonated Polymer Surfaces for Improving Blood Compatibility," Journal of Applied Polymer Scence. 74:2826-2831.
Sunthankar et al. (1973) "Reactive Disperse Dyes: Part I—Reactivity Involving Nitrene Intermediate from Azido Group," Ind. J. Chem. 11:503-504.
Tanner et al. (1980) "Polar Radicals. 15. Interpretation of Substituent Effects on the Mechanism of Electrolytic Reduction of the Carbon—Halogen bond in Series of Substituted Benzyl Halides," Journal of Organic Chemistry 45:5177-5183.
Tew et al. (2002) "De Novo Design of Biomimetic Antimicrobial Polymers," PNAS 99(8):5110-5114.
Tiller et al. (2001) "Designing Surfaces that Kill Bacteria on Contact," PNAS 98(11):5981-5985.
Tomcik et al. (2001) "Modification of Wettability of Polymer Surfaces by Microwave Plasmas," Journal of Polymer Research 8:259-266.
Tomioka (1997) "Matrix Isolation Study of Reactive O-Quinoid Compounds: Generation, Detection and Reactions," Pure & Applied Chemistry 69(4):837-840.
Tomioka and Taketsuji (1993) "Formation of Heptafulvene in Reactions of [(Methoxycarbonyl)methyl]phenylcarbene in the Gas Phases," Journal of Organic Chemistry 58:4196-4197.
Tomioka et al. (1985) "The Effect of Aryl Substituents on Arylcarbene Reactivity," Tetrahedron 41(8):1435-1440.
Tomioka et al. (1989) "Behavior of $\alpha$-(Alkoxycarbonyl)phenylcarbenes—Reactivity Under Flash Vacuum Pyrolysis Conditions and Observation of Reactive Intermediates by Low Temperature Matrix Isolation Technique," Nippon Kagaku Kaishi 8:1431-1439 (English abstract included).
UKIPO Search Report issued for British Patent Application No. 0616724.1, dated Dec. 22, 2006, 5 pages.
UKIPO Search Report issued for British Patent Application No. 0903563.5, dated Jun. 8, 2009, 6 pages.
UKIPO Search report issued for British Patent Application No. 0914692.9, dated Jan. 26, 2010, 4 pages.
Vorotnikov et al. (1991) "Formation and Conversion of Biradicals in Polymer Matrixes During Photodecomposition of Dephenyldiazomethane in Quasiclusters," Khim Fiz. 10(11):1475-1479 (English abstract only).
Waddell et al.(1992) "Polymer Surface Modification," Rubber Chemistry and Technology 65:687-696.
Worley and Sun (1996) "Biocidal Polymers," Trends in Polymer Science 4:364-370.
Wu and Lu (1997) Metal/Polymer Adhesion Enhancement by Reactive Ion Assisted Interface Bonding and Mixing, Applied Physics Letters 71:2710-2712.
Wu et al. (2006) "Preparation of Highly Reflective and Conductive Metallized Polyimide Films Through Surface Modification: Processing, Morphology and Properties," Journal of Materials Chemistry 16:310-316.
Xie and Yang (2004) "Interface and Mechanical Properties of Poly(methylmethacrylate)-Fiber Composites," Journal of Applied Polymer Science 93:2478-2483.
Yan (2000) "Covalent Functionalization of Natural Rubber Latex," Reactive and Functional Polymers 45:137-144.
Yang and Gupta (2004) "Surface Modification of Polyethyleneterephthalate by an Atmospheric-Pressure Plasma Source,: Surface & Coatings Technology 187:172-176.
Yang et al. (1997) "Study of Metal-Polymer Adhesion—A New Technology: Cu Plasma PIB," Journal of Electronic Materials 26:78-82.
Examination Report issued in EP 10707334.8, dated Jan. 13, 2014, 6 pages.
Nakazawa et al., "Electronic and molecular structures of 2D septet tris($p$-methoxyphenylmethylene)benzine as studied by ESR: a model for discotic high-spin assemblages," Mol. Cryst. Liq. Cryst. (1995) 271:163-171.
Lv et al., "Improvements in synthesis of diphenyldiazomethane," Huaxue Shiji (Chemical Reagents) (2008) 30(2):147.
Second Office Action in CN201080010264.5, dated Apr. 3, 2014, 17 pages.

* cited by examiner

CHEMICAL AGENTS CAPABLE OF FORMING COVALENT 3-D NETWORKS

CROSS-REFERENCE TO RELATED APPLICATION

This application is the national phase of PCT application PCT/GB2010/000368 having an international filing date of Mar. 2, 2010, which claims priority from European applications 0903563.5 filed Mar. 2, 2009 and 0914692.9 filed Aug. 21, 2009. The contents of these documents are incorporated herein by reference.

FIELD OF THE INVENTION

The invention relates to compounds (chemical agents) which are capable of forming extended 3-dimensional networks between multiple materials, coatings or substrates and to processes for producing such compounds. The invention further relates to the use of the compounds to alter the physical and chemical nature of materials, to produce changes in the rheological, thermal, cohesive and adhesive properties of materials, and to alter the molecular weight of a material. The invention further relates the use of the compounds to produce particle-delivery compounds, to produce products in which two or more substrates or coatings are adhered, and to convert the rheological properties of a material.

BACKGROUND TO THE INVENTION

Modern technology and products are critically dependent on the use of advanced materials, including macroscopic materials, microscopic materials and nanomaterials, with properties carefully tailored to the desired specific application. These properties can rarely be achieved with one homogeneous material or compound, but are readily available by attaching one material or compound to another, giving a composite whose properties combine the desired properties of each component. Of particular importance is the control of thermal, rheological, cohesive and adhesive properties as well as solvent resistance of materials. Such properties dictate the end application of material and limit the use of a material in challenging environments. By the addition of a linking agent which has the ability to interact with a material at two sites it is possible to influence these properties to a degree; examples of this can be found in JP59212832 or WO0158230. However since the interactions from such agents are confined to two dimensions using this approach the magnitude of the change in properties is limited. Also, the examples are limited to photo activation which precludes their use in many applications where the application of UV light is prevented, either because of sample stability, by ease of irradiation or by film thickness/composition.

By creating a 3-dimensional network on or within a material via the addition of a second chemical agent which is capable of forming strong interactions (either physically or chemically) it is possible to produce composites possessing hybrid properties and/or enhanced function. Such materials find application in a wide variety of industries, including for instance the medical, chemical, hygiene, aeronautical, automotive, computing, and consumer product industries, for example as adhesives, composite matrix materials (carbon fibre, Kevlar, etc) and coatings. They are frequently used as components which are critical for the successful function of a particular chemical product or device, or as chemical agents having an increased efficacy for a specific purpose.

There is therefore a continuing need to develop improved agents which can be used to form such three-dimensional networks, which can be used with a wide variety of substrates and materials, which offer safe handling in a production environment, and which possess curing conditions that are applicable for the market.

SUMMARY OF THE INVENTION

The inventors have provided a series of compounds which comprise multiple functionalities. The functionalities are readily convertible into reactive intermediate carbene groups which can in turn react with a wide variety of substrates, including individual compounds, nanoparticles, microparticles and bulk materials. Such functionalised compounds can be used as agents for creating 3-dimensional networks within a material or between materials for a wide variety of applications, for instance to produce products in which two or more substrates are adhered, to increase the thermal properties of coating, to alter the rheological properties of a material or to alter the chemical nature of a product such as in producing a particle-delivery compound. The process for carrying out the network formation typically involves the use of a heat cure at a temperature which is low enough to allow the process to be carried out on a plastic or polymer substrate. Furthermore, in some embodiments of the invention a protected precursor to the reactive intermediate is employed which allows a greater level of control over unwanted degradation of the materials, such as in transport or storage.

Accordingly, the invention provides a functionalised compound of formula (II), which functionalised compound comprises n carbene precursor groups which are the same or different, wherein n is an integer equal to or greater than 3:

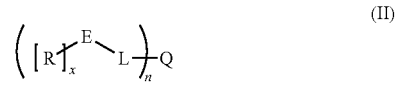

(II)

wherein x is 1, E is a group which is capable of being converted into a carbene reactive intermediate group, Q is a core moiety, a polymer or a dendrimer, and each of the [R]$_x$-E-L- groups, which are the same or different, is independently selected from a group of formula (Ie) and a group of formula (Ia):

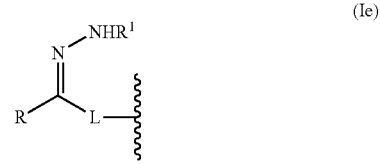

(Ie)

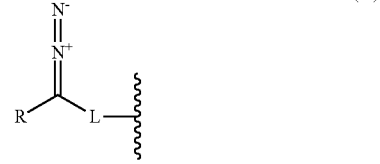

(Ia)

wherein
R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

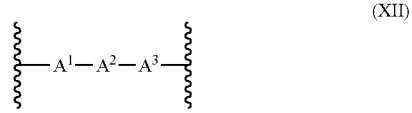

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R''), C(O)O, OC(O), C(O)N(R'') and N(R'')C(O), wherein * is the point of attachment of $A^2$ to $A^1$, wherein each of said $C_{1-20}$ alkylene and $C_{1-20}$ perfluoroalkylene groups is optionally interrupted by N(R''), O, S or arylene, and wherein each R'' is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R'')C(O), O, S, N(R''), *—C(O)O, *—C(O)N(R''), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R''), C(O), S(O), S(O)$_2$, C(O)O, OC(O), C(O)N(R'') and N(R'')C(O), wherein each R'' is independently selected from H, $C_{1-6}$ alkyl and aryl, and wherein * is the point of attachment of $A^3$ to $A^2$; and $R^1$ is —S(O)$_2R^2$ or H, wherein $R^2$ is an unsubstituted or substituted $C_{1-6}$ alkyl group or an unsubstituted or substituted aryl group;

with the proviso that when none of the [R]$_x$-E-L- groups is a group of formula (Ie) in which $R^1$ is —S(O)$_2R^2$, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

In another aspect, the invention provides a process for producing a chemically-bound three-dimensional network on or within a substrate, which process comprises:

(a) contacting a substrate with a functionalised compound of formula (II) of the invention as defined herein; and (b) generating carbene reactive intermediate groups from said carbene precursor groups, so that said carbene reactive intermediate groups react with the substrate to produce said chemically-bound three-dimensional network on or within the substrate.

In another aspect, the invention provides a composition which comprises a chemically-bound three-dimensional network on or within a substrate, the composition comprising:

(i) a substrate; and
(ii) a chemically-bound three-dimensional network on or within the substrate, which chemically-bound three-dimensional network is of formula (XXVIVa)

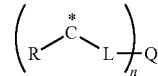

wherein
n is an integer equal to or greater than 3;
C is a carbon atom;
* is a point of attachment of the carbon atom to the substrate or to another molecule or moiety in the composition;
R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ aryldi($C_{1-20}$ diaryl ($C_{1-20}$ alkyl)silyl and triarylsilyl;

each L, which is the same or different, is a single bond or a group of formula (XII)

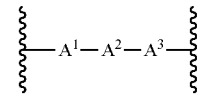

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R''), C(O)O, OC(O), C(O)N(R'') and N(R'')C(O), wherein * is the point of attachment of $A^2$ to $A^1$, wherein each of said $C_{1-20}$ alkylene and $C_{1-20}$ perfluoroalkylene groups is optionally interrupted by N(R''), O, S or arylene, and wherein each R'' is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$- arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer.

In another aspect, the invention provides a process for producing a composition which comprises:
(i) a substrate; and
(ii) a chemically-bound three-dimensional network on or within the substrate, which chemically-bound three-dimensional network is of formula (XXVIa)

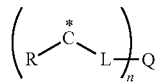

(XXVIa)

wherein:
n is an integer equal to or greater than 3;
C is a carbon atom;
* is a point of attachment of the carbon atom to the substrate or to another molecule or moiety in the composition;
R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;
each L, which is the same or different, is a single bond or a group of formula (XII)

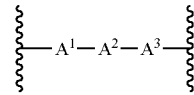

(XII)

wherein:
$A^1$ is bonded to the carbon atom bonded to R, wherein $A^1$ is an unsubstituted or substituted group selected from arylene and heteroarylene;
$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer,
which process comprises:
(a) contacting a substrate with a functionalised compound of formula (II) of the invention as defined herein; and
(b) generating carbene reactive intermediate groups from said carbene precursor groups, so that said carbene reactive intermediate groups react with the substrate to produce said composition.

In another aspect, the invention provides a process for producing a chemically-bound three-dimensional network between a first substrate and a second substrate, which process comprises:
(a) contacting a first substrate and a second substrate with a functionalised compound of formula (II) of the invention as defined herein; and
(b) generating carbene reactive intermediate groups from said carbene precursor groups, so that said carbene reactive intermediate groups react with the first substrate and the second substrate to produce said chemically-bound three-dimensional network between said first and second substrates.

In another aspect, the invention provides a composition which comprises:
a first substrate;
a second substrate; and
a three-dimensional network of formula (XXVIa), which is bound to said first and second substrates:

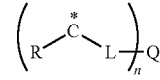

(XXVIa)

wherein
n is an integer equal to or greater than 3;
C is a carbon atom;
* is a point of attachment of the carbon atom to the first or second substrate or to another molecule or moiety in said composition;
R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ aryldi($C_{1-20}$ diaryl ($C_{1-20}$ alkyl)silyl and triarylsilyl;
each L, which is the same or different, is a single bond or a group of formula (XII)

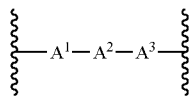

(XII)

wherein:
A$^1$ is bonded to the carbon atom bonded to R, wherein A$^1$ is an unsubstituted or substituted group selected from arylene and heteroarylene;

A$^2$ is a single bond or an unsubstituted or substituted group selected from C$_{1-20}$ alkylene, C$_{1-20}$ perfluoroalkylene, arylene, heteroarylene, *—C$_{1-20}$ alkylene-(O—C$_{1-20}$ alkylene-)$_m$ wherein m is 1 to 20, *—Z$^1$—C$_{1-20}$ alkylene, *—Z$^1$—C$_{1-20}$ perfluoroalkylene, *—Z$^1$-arylene, *—Z$^1$-heteroarylene and *—Z$^1$—C$_{1-20}$ alkylene-(O—C$_{1-20}$ alkylene-)$_m$ wherein m is 1 to 20, wherein Z$^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said C$_{1-20}$ alkylene and C$_{1-20}$ perfluoroalkylene groups is optionally interrupted by N(R"), O, S or arylene, and wherein each R" is independently selected from H, C$_{1-6}$ alkyl and aryl; and A$^3$ is a single bond or an unsubstituted or substituted group selected from *—Z$^2$-arylene, *—Z$^2$-heteroarylene, *—Z$^2$—C$_{1-20}$ alkylene, arylene, heteroarylene, C$_{1-20}$ alkylene, *—Z$^2$-arylene-O, *—Z$^2$-heteroarylene-O, *—Z$^2$—C$_{1-20}$ alkylene-O, *-arylene-O, *-heteroarylene-O, *—C$_{1-20}$ alkylene-O, C(O), S(O)$_2$, *—OC(O), *—N(R")C(O), O, S, N(R"), *—C(O)O, *—C(O)N(R"), *—S(O)$_2$O, C$_{1-20}$ alkenylene, C$_{1-20}$ alkynylene, *—Z$^2$—C$_{1-20}$ alkenylene and *—Z$^2$—C$_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$; and Q is a core moiety, a polymer or a dendrimer.

In another aspect, the invention provides a process for producing a composition which comprises:
a first substrate;
a second substrate; and
a three-dimensional network of formula (XXVIVa):

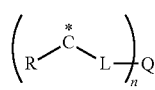

(XXVIVa)

wherein
n is an integer equal to or greater than 3;
C is a carbon atom;
* is a point of attachment of the carbon atom to the first or second substrate or to another molecule or moiety in said composition;
R is aryl or heteroaryl, which aryl or heteroaryl is unsubstituted or substituted by one, two, three, four or five groups, which groups are the same or different and are independently selected from C$_{1-20}$ alkyl, C$_{2-20}$ alkenyl, C$_{2-20}$ alkynyl, C$_{1-20}$ haloalkyl, C$_{1-20}$ fluoroalkyl, C$_{1-20}$ perfluoroalkyl, aryl, cyano, nitro, hydroxy, halo, carboxy, amino, C$_{1-10}$ alkylamino, di(C$_{1-10}$)alkylamino, arylamino, diarylamino, arylalkylamino, amido, acyl, acyloxy, acylamido, ester, C$_{1-10}$ alkoxy, aryloxy, haloalkyl, thiol, C$_{1-10}$ alkylthio, arylthio, sulfonic acid, sulfonyl, sulfonamide, tri(C$_{1-20}$ alkyl)silyl, aryldi(C$_{1-20}$ alkyl)silyl, diaryl(C$_{1-20}$ alkyl)silyl and triarylsilyl;

each L, which is the same or different, is a single bond or a group of formula (XII)

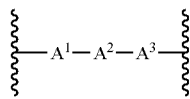

(XII)

wherein:
A$^1$ is bonded to the carbon atom bonded to R, wherein A$^1$ is an unsubstituted or substituted group selected from arylene and heteroarylene;

A$^2$ is a single bond or an unsubstituted or substituted group selected from C$_{1-20}$ alkylene, C$_{1-20}$ perfluoroalkylene, arylene, heteroarylene, *—C$_{1-20}$ alkylene-(O—C$_{1-20}$ alkylene-)$_m$ wherein m is 1 to 20, *—Z$^1$—C$_{1-20}$ alkylene, *—Z$^1$—C$_{1-20}$ perfluoroalkylene, *—Z$^1$-arylene, *—Z$^1$-heteroarylene and *—Z$^1$—C$_{1-20}$ alkylene-(O—C$_{1-20}$ alkylene-)$_m$ wherein m is 1 to 20, wherein Z$^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said C$_{1-20}$ alkylene and C$_{1-20}$ perfluoroalkylene groups is optionally interrupted by N(R"), O, S or arylene, and wherein each R" is independently selected from H, C$_{1-6}$ alkyl and aryl; and A$^3$ is a single bond or an unsubstituted or substituted group selected from *—Z$^2$-arylene, *—Z$^2$-heteroarylene, *—Z$^2$—C$_{1-20}$ alkylene, arylene, heteroarylene, C$_{1-20}$ alkylene, *—Z$^2$-arylene-O, *—Z$^2$-heteroarylene-O, *—Z$^2$—C$_{1-20}$ alkylene-O, *-arylene-O, *-heteroarylene-O, *—C$_{1-20}$ alkylene-O, C(O), S(O)$_2$, *—OC(O), *—N(R")C(O), O, S, N(R"), *—C(O)O, *—C(O)N(R"), *—S(O)$_2$O, C$_{1-20}$ alkenylene, C$_{1-20}$ alkynylene, *—Z$^2$—C$_{1-20}$ alkenylene and *—Z$^2$—C$_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$; and Q is a core moiety, a polymer or a dendrimer,
which process comprises:
(a) contacting a first substrate and a second substrate with a functionalised compound of formula (II) of the invention as defined herein; and
(b) generating carbene reactive intermediate groups from said carbene precursor groups, so that said carbene reactive intermediate groups react with the first substrate and the second substrate to produce said composition.

In another aspect, the invention provides a process for producing a film or a coating, which process comprises:
(a) disposing a film or coating formulation onto the surface of a substrate, which film or coating formulation comprises a functionalised compound of formula (II) of the invention as defined herein; and
(b) generating carbene reactive intermediate groups from said carbene precursor groups, thereby forming a film or a coating on said substrate.

In one embodiment, the process is for producing a film, and the process further comprises (c) removing said film from said substrate.

In another aspect, the invention provides a coated substrate which comprises:
a substrate; and
a coating on a surface of the substrate, which coating comprises a three-dimensional network of formula (XXVIVa):

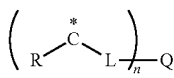

(XXVIVa)

wherein n is an integer equal to or greater than 3;

C is a carbon atom;

* is a point of attachment of the carbon atom to the substrate or to another molecule or moiety in the coating;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)allylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

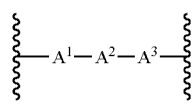

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer.

In another aspect, the invention provides a process for producing a coated substrate of the invention as defined above, comprises:

(a) disposing a coating formulation onto the surface of a substrate, which coating formulation comprises a functionalised compound of formula (II) of the invention as defined herein; and (b) generating carbene reactive intermediate groups from said carbene precursor groups, thereby forming a coating on said substrate.

In another aspect, the invention provides a product which comprises:

a first substrate;

a second substrate; and a composition at an interface of the first and second substrates, which composition comprises (i) a third material and (ii) a three-dimensional network of formula (XXVIVa):

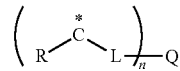

(XXVIVa)

wherein n is an integer equal to or greater than 3;

C is a carbon atom;

* is a point of attachment of the carbon atom to the first substrate, the second substrate, the third material, or to another molecule or moiety in said composition at said interface of the first and second substrates;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)allylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

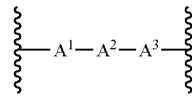

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, $Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer.

In another aspect, the invention provides a process for producing a product of the invention as defined above, which process comprises:

(a) providing a composition at an interface of a first substrate and a second substrate, which composition comprises (i) a third material and (ii) a functionalised compound of formula (II) of the invention as defined herein; and (b) generating carbene reactive intermediate groups from said carbene precursor groups, so that said carbene reactive intermediate groups react with the first substrate, the second substrate, and the third material, to produce said product.

In another aspect, the invention provides a process for producing a treated particle, which process comprises:

(a) contacting a functionalised cross linking compound with a substrate particle, wherein the functionalised cross linking compound is a compound of formula (II) of the invention as defined herein; and (b) generating carbene reactive intermediate groups from said carbene precursor groups, so that a carbene reactive intermediate group reacts with the substrate particle to attach the particle to the compound, thereby yielding said particle-delivery compound.

The invention also provides a treated particle, which treated particle comprises a substrate particle attached to a cross linking moiety of formula (XXVIVa):

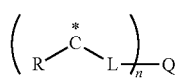

(XXVIVa)

wherein n is an integer equal to or greater than 3;

C is a carbon atom;

* is a point of attachment of the carbon atom to the substrate particle or to another moiety or molecule;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

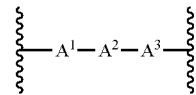

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer.

The treated particle of the invention may be used as a particle-delivery compound. Accordingly, the treated particle may be termed a particle-delivery compound.

In another aspect, the invention provides a process for cross linking a first substrate to a second substrate, which first and second substrates are the same or different, which process comprises (a) contacting the first and second substrates with a functionalised cross linking compound, wherein the functionalised cross linking compound is a compound of formula (II) of the invention as defined herein; and (b) generating carbene reactive intermediate groups from said carbene precursor groups, so that at least one reactive intermediate group reacts with the first substrate and at least one other reactive intermediate group reacts with the second substrate, thereby cross linking the first and second substrates.

In another aspect, the invention provides a cross-linked product comprising:
(a) a first substrate;
(b) a second substrate; and
(c) a cross linking moiety of formula (XXVIVa):

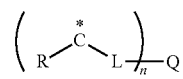

(XXVIVa)

wherein n is an integer equal to or greater than 3;

C is a carbon atom;

* is a point of attachment of the carbon atom to the first substrate, the second substrate, or to another moiety or molecule;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ aryldi($C_{1-20}$ alkyl)silyl, diaryl($C_{1-20}$ alkyl)silyl and triarylsilyl;

each L, which is the same or different, is a single bond or a group of formula (XII)

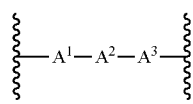

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a polymer or a dendrimer.

In another aspect, the invention provides a process for producing a functionalised compound of formula (II), which functionalised compound comprises n carbene precursor groups which are the same or different, wherein n is an integer equal to or greater than 3

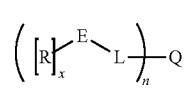

(II)

wherein x is 1, E is a group which is capable of being converted into a carbene reactive intermediate group, Q is a core moiety, a polymer or a dendrimer, and each of the [R]$_x$-E-L- groups, which are the same or different, is independently selected from a group of formula (Ie) and a group of formula (Ia):

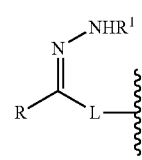

(Ie)

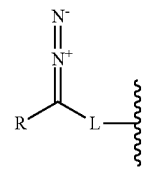

(Ia)

wherein

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

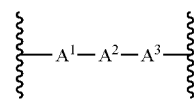

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and $R^1$ is —S(O)$_2R^2$ or H, wherein $R^2$ is an unsubstituted or substituted $C_{1-6}$ alkyl group or an unsubstituted or substituted aryl group;

with the proviso that when none of the [R]$_x$-E-L- groups is a group of formula (Ie) in which $R^1$ is —S(O)$_2R^2$, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

which process comprises:
(a) treating a first compound, Q', which is a core moiety, a polymer or a dendrimer and which bears n functional groups, with at least one second compound of formula (VIa)

$$\overset{Y}{\underset{R \quad L'}{\|}} \quad (VIa)$$

wherein:
L' is a leaving group or a reactive precursor to said group of formula (XII), wherein L' is reactable with a said functional group to couple the second compound to the first compound,
R is aryl or heteroaryl, which aryl or heteroaryl is unsubstituted or substituted by one, two, three, four or five groups, which groups are the same or different and are fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl, and
Y is N=N, O or N—NHR$^1$, wherein R$^1$ is H or —S(O)$_2R^2$ and wherein R$^2$ is an unsubstituted or substituted $C_{1-6}$ alkyl group or an unsubstituted or substituted aryl group, provided that when none of the [R]$_x$-E-L- groups in the functionalised compound of formula (II) to be produced is a group of formula (Ie) in which R$^1$ is —S(O)$_2R^2$, then each L' is a reactive precursor to said group of formula (XII) and Q' is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

thereby producing a third compound of formula (IXa):

$$\left( \overset{Y}{\underset{R \quad L}{\|}} \right)_n Q \quad (IXa)$$

wherein Q, L, R, Y and n are as defined above;
provided that:
when Y is O, the process further comprises:
(b) treating the third compound with $H_2N$—NHR$^1$ in the presence of heat, wherein R$^1$ is as defined above, thereby producing a fourth compound of formula (X):

$$\left( \overset{N\diagdown NHR^1}{\underset{R \quad L}{\|}} \right)_n Q \quad (X)$$

wherein Q, L, R, R$^1$ and n are as defined above; and, optionally,
(c) converting some or all of the N—NHR$^1$ groups of said fourth compound into diazo groups, N=N;
and provided that:
when Y is N—NHR$^1$, the process optionally further comprises:
(b) converting some or all of the Y groups of said third compound into diazo groups;
thereby producing said functionalised compound of formula (II).

DETAILED DESCRIPTION OF THE INVENTION

Figure 1:
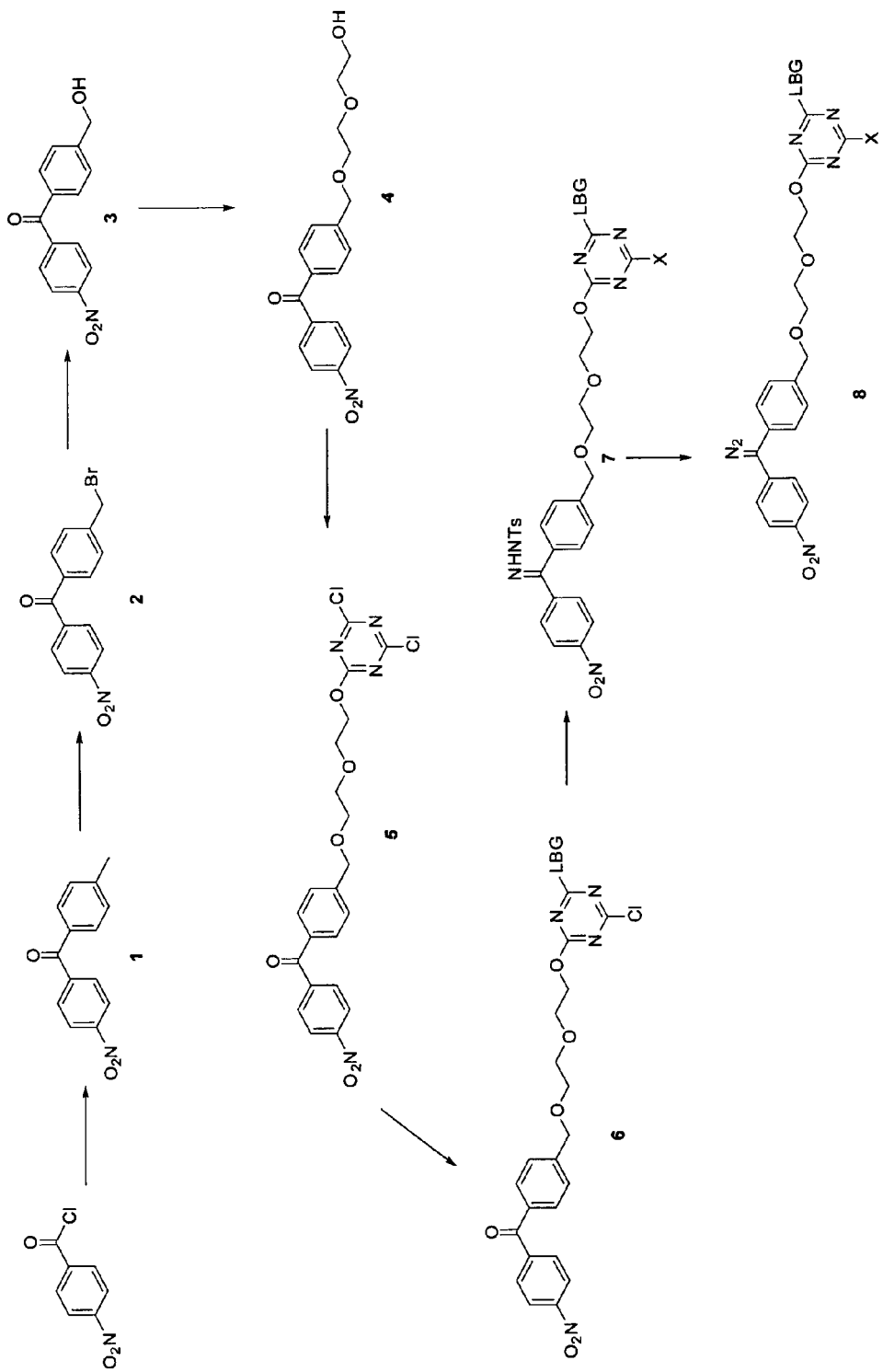
FIG. 1 is a schematic representation of the synthesis of triazine linked diazomethane locust bean gum.

As used herein, a $C_{1-20}$ alkyl group is an unsubstituted or substituted, straight or branched chain saturated hydrocarbon radical having from 1 to 20 carbon atoms. Typically it is $C_{1-10}$ alkyl, for example methyl, ethyl, propyl, butyl, pentyl, hexyl, heptyl, octyl, nonyl or decyl, or $C_{1-6}$ alkyl, for example methyl, ethyl, propyl, butyl, pentyl or hexyl, or $C_{1-4}$ alkyl, for example methyl, ethyl, i-propyl, n-propyl, t-butyl, s-butyl or n-butyl. In one embodiment, it is a $C_{2-20}$ alkyl group or, for instance, a $C_{3-20}$ alkyl or a $C_{4-20}$ alkyl group. When an alkyl group is substituted it typically bears one or more (e.g. one, two, three or four) substituents selected from substituted or unsubstituted $C_{1-20}$ alkyl; substituted or unsubstituted $C_{2-20}$ alkenyl; substituted or unsubstituted $C_{2-20}$ alkynyl; substituted or unsubstituted aryl; substituted or unsubstituted aralkyl; halo; cyano; keto; amino; $C_{1-10}$ alkylamino; di($C_{1-10}$) allylamino; arylamino; diarylamino; arylalkylamino; amido; acylamido; $C_{1-20}$ haloalkyl (e.g. —$CF_3$); ester; acyl; acyloxy; $C_{1-10}$ alkoxy; aryloxy; nitro; hydroxyl, carboxy; sulfonic acid; sulfonyl; sulphonamide; sulfhydryl (i.e. thiol, —SH); $C_{1-10}$ alkylthio; arylthio; tri($C_{1-20}$ alkyl)silyl; aryldi($C_{1-20}$ alkyl)silyl; diaryl($C_{1-20}$ alkyl)silyl; and triarylsilyl.

Examples of substituted alkyl groups include $C_{1-20}$ haloalkyl, alkoxyalkyl and alkaryl groups. The term alkaryl, as used herein, pertains to a $C_{1-20}$ alkyl group in which at least one hydrogen atom (e.g., 1, 2, 3) has been replaced with an aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, $Ph-CH_2CH_2$—), styryl ($Ph-CH=CH$—), cinnamyl ($Ph-CH=CH-CH_2$—).

Typically a substituted $C_{1-20}$ alkyl group carries 1, 2 or 3 substituents, for instance 1 or 2.

A $C_{1-20}$ haloalkyl group is a straight or branched chain saturated $C_{1-20}$ alkyl group in which at least one hydrogen atom has been replaced with a halogen atom, typically F, Cl or Br. In a $C_n$ haloalkyl group, where n is from 1 to 20, the number of hydrogen atoms replaced with a halogen atom may be from n to (2n+1). The halogen atoms may be the same or different. $C_{1-20}$ haloalkyl groups include $C_{1-20}$ fluoroalkyl groups and $C_{1-20}$ perfluoroalkyl groups, as defined below. A $C_{1-20}$ haloalkyl group may have at least two halogen atoms or, for instance, at least three halogen atoms.

A $C_{1-20}$ fluoroalkyl group is a straight or branched chain saturated $C_{1-20}$ alkyl group in which at least one hydrogen atom has been replaced with a fluorine atom. In a $C_n$ fluoroalkyl group, where n is from 1 to 20, the number of hydrogen atoms replaced with a fluorine atom may be from n to (2n+1). Thus, $C_{1-20}$ fluoroalkyl groups include $C_{1-20}$ perfluoroalkyl groups, in which all the hydrogen atoms that would otherwise have been present are replaced with a fluorine atom. Typically, a $C_{1-20}$ fluoroalkyl group has at least two fluorine atoms, more typically at least three fluorine atoms. Typically a $C_{1-20}$ fluoroalkyl group is a $C_{2-20}$ fluoroalkyl group, or for instance a $C_{3-20}$ fluoroalkyl group. Typically, a $C_{2-20}$ fluoroalkyl group has at least three fluorine atoms, more typically at least four fluorine atoms. Typically, a $C_{3-20}$ fluoroalkyl group has at least three fluorine atoms, more typically at least four fluorine atoms or, for instance, at least six fluorine atoms.

A $C_{1-20}$ perfluoroalkyl group is a straight or branched chain saturated perfluorinated hydrocarbon radical having from 1 to 20 carbon atoms. "Perfluorinated" in this context means completely fluorinated such that there are no carbon-bonded hydrogen atoms replaceable with fluorine. Typically it is $C_{1-12}$ perfluoroalkyl, for example trifluoromethyl ($C_1$), pentafluoroethyl ($C_2$), perfluoropropyl ($C_3$) (including perfluoro-n-propyl and perfluoro-iso-propyl), perfluorobutyl ($C_4$) (including perfluoro-n-butyl, perfluoro-iso-butyl, perfluoro-sec-butyl and perfluoro-tert-butyl), perfluoropentyl ($C_5$), perfluorohexyl ($C_6$), perfluoroheptyl ($C_7$), perfluorooctyl ($C_8$), perfluorononyl ($C_9$), perfluorodecyl ($C_{10}$), perfluoroundecyl ($C_{11}$) and perfluorododecyl ($C_{12}$), including straight chained and branched isomers thereof.

A $C_{1-20}$ hydrocarbon moiety is a straight-chained or branched, saturated or unsaturated hydrocarbon moiety having from 1 to 20 carbon atoms. A $C_{1-20}$ hydrocarbon moiety may be unsubstituted or substituted, the substituents, unless otherwise specified, being selected from those listed above for $C_{1-20}$ alkyl groups. Typically, when a $C_{1-20}$ hydrocarbon moiety is substituted, it is substituted by from one to four (e.g. one, two, three or four) substituents.

A tri($C_{1-20}$ alkyl)silyl group represents a group of formula: —Si(R')(R")(R'") wherein R', R" and R'", which are the same or different, are unsubstituted or substituted, straight or branched chain $C_{1-20}$ alkyl groups as defined above.

A aryldi($C_{1-20}$ alkyl)silyl group represents a group of formula: —Si(R')(R")(R'") wherein R' and R", which are the same or different, are unsubstituted or substituted, straight or branched chain $C_{1-20}$ alkyl groups as defined above, and wherein R'" is an unsubstituted or substituted aryl group.

A diaryl($C_{1-20}$ alkyl)silyl group represents a group of formula: —Si(R')(R")(R'") wherein R' is an unsubstituted or substituted, straight or branched chain $C_{1-20}$ alkyl group as defined above, and wherein R" and R'", which are the same or different, are unsubstituted or substituted aryl groups.

A triarylsilyl group represents a group of formula: —Si(R')(R")(R'") wherein R', R" and R'", which are the same or different, are unsubstituted or substituted aryl groups.

A $C_{2-20}$ alkenyl group is a straight or branched group, which contains from 2 to 20 carbon atoms. One or more double bonds may be present in the alkenyl group, typically one double bond. A $C_{2-20}$ alkenyl group is typically ethenyl or a $C_{3-10}$ alkenyl group, i.e. a $C_{2-10}$ alkenyl group, more typically a $C_{2-6}$ alkenyl group. A $C_{3-10}$ alkenyl group is typically a $C_{3-6}$ alkenyl group, for example allyl, propenyl, butenyl, pentenyl or hexenyl. A $C_{2-4}$ alkenyl group is ethenyl, propenyl or butenyl. An alkenyl group may be unsubstituted or substituted by one to four (e.g. one, two, three or four) substituents, the substituents, unless otherwise specified, being selected from those listed above for $C_{1-20}$ alkyl groups. Where two or more substituents are present, these may be the same or different.

A $C_{2-20}$ alkynyl group is a straight or branched group which, unless otherwise specified, contains from 2 to 20 carbon atoms. One or more triple bonds, and optionally one or more double bonds may be present in the alkynyl group, typically one triple bond. A $C_{2-20}$ alkynyl group is typically ethynyl or a $C_{3-10}$ alkynyl group, i.e. a $C_{2-10}$ alkynyl group, more typically a $C_{2-6}$ alkynyl group. A $C_{3-10}$ alkynyl group is typically a $C_{3-6}$ alkynyl group, for example propynyl, butynyl, pentynyl or hexynyl. A $C_{2-4}$ alkynyl group is ethynyl, propynyl or butynyl. An alkynyl group may be unsubstituted or substituted by one to four substituents (e.g. one, two, three or four), the substituents, unless otherwise specified, being selected from those listed above for $C_{1-20}$ alkyl groups. Where two or more substituents are present, these may be the same or different.

An aryl ring is an unsubstituted or substituted aromatic ring of covalently linked carbon atoms. Typically, the aryl ring is a 5- or 6-membered aryl ring, examples of which include cyclopentadienyl ($C_p$) and phenyl. An aryl ring may be unsubstituted or substituted by, typically, one to five substituents (e.g. one, two, three, four or five), the substituents, unless otherwise specified, being selected from those listed above for $C_{1-20}$ alkyl groups. Where two or more substituents are present, these may be the same or different.

A heteroaryl ring is an unsubstituted or substituted heteroaromatic ring of covalently linked atoms including one or more heteroatoms. The one or more heteroatoms are typically selected from nitrogen, phosphorus, silicon, oxygen and sulfur (more commonly from nitrogen, oxygen and sulfur). A heteroaryl ring is typically a 5- or 6-membered heteroaryl ring containing at least one heteroatom selected from nitrogen, phosphorus, silicon, oxygen and sulfur (more commonly selected from nitrogen, oxygen and sulfur). It may contain, for example, 1, 2 or 3 heteroatoms. Examples of heteroaryl rings include pyridine, pyrazine, pyrimidine, pyridazine, furan, thiofuran, pyrazole, pyrrole, oxazole, oxadiazole, isoxazole, thiadiazole, thiazole, isothiazole, imidazole and pyrazole. A heteroaryl ring may be unsubstituted or substituted by, typically, one to four substituents (e.g. one, two, three or four), the substituents, unless otherwise specified, being selected from those listed above for $C_{1-20}$ alkyl groups. Where two or more substituents are present, these may be the same or different.

A $C_{5-10}$ carbocyclic ring is an unsubstituted or substituted closed ring of from 5 to 10 covalently linked carbon atoms, which ring is saturated or unsaturated. Typically, the $C_{5-10}$ carbocyclic ring is not an aromatic ring. Typically the $C_{5-10}$ carbocyclic ring is a $C_{5-6}$ carbocyclic ring. The carbocyclic ring may be saturated or unsaturated. Thus, the term $C_{5-10}$ carbocyclic ring includes the sub-classes $C_{5-10}$ cycloalkyl ring, $C_{5-10}$ cycloalkyenyl ring and $C_{5-10}$ cycloalkynyl ring. When a $C_{5-10}$ carbocyclic ring is substituted it typically bears one or more substituents selected from those listed above for $C_{1-20}$ alkyl groups. Examples of $C_{5-10}$ carbocyclic rings include, but are not limited to:

cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$), cyclopentene ($C_5$), cyclopentadiene ($C_5$), cyclohexene ($C_6$), cyclohexadiene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$).

A $C_{5-10}$ heterocyclic ring is an unsubstituted or substituted closed ring of from 5 to 10 covalently linked atoms, which ring is saturated or unsaturated, wherein at least one of the ring atoms is a multivalent ring heteroatom, for example, nitrogen, phosphorus, silicon, oxygen, or sulfur (though more commonly nitrogen, oxygen, or sulfur). Typically, the $C_{5-10}$ heterocyclic ring is not an aromatic ring. Typically, the $C_{5-10}$ heterocyclic ring has from 1 to 4 heteroatoms, the remainder of the ring atoms are carbon. Typically, the $C_{5-10}$ heterocyclic ring is a $C_{5-6}$ heterocyclic ring in which from 1 to 4 of the ring atoms are ring heteroatoms, and the remainder of the ring atoms are carbon atoms. In this context, the prefixes $C_{5-10}$ and $C_{5-6}$ denote the number of ring atoms, or range of number of ring atoms. When a $C_{5-10}$ heterocyclic ring is substituted it typically bears one or more substituents selected from those listed above for $C_{1-20}$ alkyl groups.

Examples of monocyclic $C_{5-10}$ heterocyclic rings include, but are not limited to:

$N_1$: pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

A $C_{3-20}$ carbocyclyl group is an unsubstituted or substituted monovalent moiety obtained by removing a hydrogen atom from an alicyclic ring atom of a carbocyclic ring of a carbocyclic compound, which moiety has from 3 to 20 carbon atoms (unless otherwise specified), including from 3 to 20 ring atoms. The carbocyclyl ring may be saturated or unsaturated. Thus, the term "carbocyclyl" includes the sub-classes cycloalkyl, cycloalkyenyl and cycloalkynyl. Preferably, each ring has from 5 to 7 ring atoms. Examples of groups of $C_{3-20}$ carbocyclyl groups include $C_{3-10}$ carbocyclyl, $C_{5-7}$ carbocyclyl and $C_{5-6}$ carbocyclyl. When a $C_{3-20}$ carbocyclyl group is substituted it typically bears one or more substituents (typically one, two, three or four substituents) selected from those listed above for $C_{1-20}$ alkyl groups.

Examples of $C_{3-20}$ carbocyclyl groups include, but are not limited to, those derived from saturated monocyclic hydrocarbon compounds:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:

cyclopropene ($C_3$), cyclobutene ($C_4$), cyclopentene ($C_5$), cyclopentadiene ($C_5$), cyclohexene ($C_6$), cyclohexadiene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:

thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$); unsaturated polycyclic hydrocarbon compounds: camphene ($C_{10}$), limonene ($C_{10}$), pinene ($C_{10}$);

polycyclic hydrocarbon compounds having an aromatic ring:

indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), 5,5,8,8-tetramethyl tetraline ($C_{14}$), acephenanthrene ($C_{15}$), aceanthrene ($C_{16}$), cholanthrene ($C_{20}$).

Further examples of $C_{3-20}$ carbocyclyl groups include $C_{3-20}$ halocarbocyclyl groups, $C_{3-20}$ fluorocarbocyclyl groups, $C_{3-20}$ perfluorocarbocyclyl groups and $C_{3-10}$ cycloalkyl groups.

A $C_{3-20}$ halocarbocyclyl group is a $C_{3-20}$ carbocyclyl group in which at least one hydrogen atom has been replaced with a halogen atom, typically F, Cl or Br. The halogen atoms may be the same or different. $C_{3-20}$ halocarbocyclyl groups include $C_{3-20}$ fluorocarbocyclyl groups and $C_{3-20}$ perfluorocarbocyclyl groups, as defined below. A $C_{3-20}$ halocarbocyclyl group may have at least two halogen atoms or, for instance, at least three or at least four, at least five or at least six halogen atoms.

A $C_{3-20}$ fluorocarbocyclyl group is a $C_{3-20}$ carbocyclyl group in which at least one hydrogen atom has been replaced with a fluorine atom. $C_{3-20}$ fluorocarbocyclyl groups include $C_{3-20}$ perfluorocarbocyclyl groups, as defined below. A $C_{3-20}$ fluorocarbocyclyl group may have at least two fluorine atoms or, for instance, at least three or at least four, at least five or at least six fluorine atoms.

A $C_{3-20}$ perfluorocarbocyclyl group a perfluorinated $C_{3-20}$ carbocyclyl group. "Perfluorinated" in this context means completely fluorinated such that there are no carbon-bonded hydrogen atoms replaceable with fluorine.

A $C_{3-10}$ cycloalkyl group or moiety is a 3- to 10-membered unsubstituted or substituted group or moiety, typically a 3- to 6-membered group or moiety, which may be a monocyclic ring or which may consist of two or more fused rings. Examples of $C_{3-10}$ cycloalkyl groups or moieties include cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$), thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$) and decalin (decahydronaphthalene) ($C_{10}$).

A $C_{3-20}$ heterocyclyl group is an unsubstituted or substituted monovalent, monocyclic, bicyclic or tricyclic moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms. When a $C_{3-20}$ heterocyclyl group is substituted it typically bears one or more substituents selected from those listed above for $C_{1-20}$ alkyl groups. Typically a substituted $C_{3-20}$ heterocyclyl group carries 1, 2 or 3 substituents, for instance 1 or 2.

Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic $C_{3-20}$ heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of $C_{3-20}$ heterocyclyl groups which are also aryl groups are described below as heteroaryl groups.

An aryl group is a substituted or unsubstituted, monocyclic or bicyclic aromatic group which typically contains from 6 to 14 carbon atoms, preferably from 6 to 10 carbon atoms in the ring portion. Examples include phenyl, naphthyl, indenyl and indanyl groups. An aryl group is unsubstituted or substituted. When an aryl group as defined above is substituted it typically bears one or more substituents (for instance, one, two, three, four or five substituents) selected from those listed above for $C_{1-20}$ alkyl groups. A substituted aryl group may be substituted in two positions with a single unsubstituted or substituted $C_{1-6}$ alkylene group, or with a bidentate group represented by the formula —X—$C_{1-6}$ alkylene, or —X—$C_{1-6}$ alkylene-X—, wherein X is selected from O, S and NR, and wherein R is H, aryl or $C_{1-6}$ alkyl. Thus a substituted aryl group may be an aryl group fused with a cycloalkyl group or with a heterocyclyl group. A further example of a substituted aryl group is a $C_{6-10}$ perfluoroaryl group.

A $C_{6-10}$ perfluoroaryl group is a perfluorinated aryl group which contains from 6 to 10 carbon atoms in the ring portion. "Perfluorinated" in this context means completely fluorinated such that there are no carbon-bonded hydrogen atoms replaceable with fluorine. Typically it is pentafluorophenyl.

The term aralkyl as used herein, pertains to an aryl group in which at least one hydrogen atom (e.g., 1, 2, 3) has been substituted with a $C_{1-20}$ alkyl group. Examples of such groups include, but are not limited to, tolyl (from toluene), xylyl (from xylene), mesityl (from mesitylene), and cumenyl (or cumyl, from cumene), and duryl (from durene).

The ring atoms of an aryl group may include one or more heteroatoms, as in a heteroaryl group. Such an aryl group (a heteroaryl group) is a substituted or unsubstituted mono- or bicyclic heteroaromatic group which typically contains from 6 to 10 atoms in the ring portion including one or more heteroatoms. It is generally a 5- or 6-membered ring, or two fused rings each of which is the same or different and typically independently selected from a 5-membered ring and a 6-membered ring, containing at least one heteroatom selected from O, S, N, P, Se and Si. It may contain, for example, 1, 2 or 3 heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl. A heteroaryl group may be unsubstituted or substituted, for instance, as specified above for aryl. Typically it carries 0, 1, 2 or 3 substituents.

A $C_{1-20}$ alkylene group is an unsubstituted or substituted bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene ($C_{1-20}$ alkenylene), alkynylene ($C_{1-20}$ alkynylene), cycloalkylene, etc. Typically it is $C_{1-10}$ alkylene, or $C_{1-6}$ alkylene. Typically it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be unsubstituted or substituted, for instance, as specified above for alkyl. Typically a substituted alkylene group carries 1, 2 or 3 substituents, for instance 1 or 2.

In this context, the prefixes (e.g., $C_{1-4}$, $C_{1-7}$, $C_{1-10}$, $C_{2-7}$, $C_{3-7}$, etc.) denote the number of carbon atoms, or range of number of carbon atoms. For example, the term "$C_{1-4}$ alkylene," as used herein, pertains to an alkylene group having from 1 to 4 carbon atoms. Examples of groups of alkylene groups include $C_{1-4}$ alkylene ("lower alkylene"), $C_{1-7}$ alkylene and $C_{1-10}$ alkylene.

Examples of linear saturated $C_{1-7}$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but is not limited to, —CH=CH— (vinylene), —CH=CH—$CH_2$—, —$CH_2$—CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—$CH_2$—CH=CH—, and —CH=CH—$CH_2$—$CH_2$—CH=CH—.

Examples of branched partially unsaturated $C_{1-7}$ alkylene groups include, but is not limited to, —$C(CH_3)$=CH—, —$C(CH_3)$=CH—$CH_2$—, and —CH=CH—$CH(CH_3)$—.

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene). These are examples of $C_{5-6}$ cycloalkylene groups.

An example of a substituted $C_{1-20}$ alkylene group is a $C_{1-20}$ perfluoroalkylene group. A $C_{1-20}$ perfluoroalkylene group is a perfluorinated $C_{1-20}$ alkylene group. "Perfluorinated" in this context means completely fluorinated such that there are no carbon-bonded hydrogen atoms replaceable with fluorine.

$C_{1-20}$ alkylene, $C_{1-20}$ perfluoroalkylene, $C_{1-20}$ alkyl, $C_{1-20}$ haloalkyl, $C_{1-20}$ fluoroalkyl and $C_{1-20}$ perfluoroalkyl groups as defined herein are either uninterrupted or interrupted by one or more heteroatoms or heterogroups, such as S, O or N(R") wherein R" is H, $C_{1-6}$ alkyl or aryl (typically phenyl), or by one or more arylene groups. The arylene groups are typically phenylene, but may be perfluoroarylene groups, for instance tetrafluorophenylene. The phrase "optionally interrupted" as used herein thus refers to a $C_{1-20}$ alkylene, $C_{1-20}$ perfluoroalkylene, $C_{1-20}$ alkyl, $C_{1-20}$ haloalkyl, $C_{1-20}$ fluoroalkyl or $C_{1-20}$ perfluoroalkyl group, as defined above, which is uninterrupted or which is interrupted between adjacent carbon atoms by a heteroatom such as oxygen or sulfur, by a heterogroup such as N(R") wherein R" is H, aryl or $C_{1-6}$ alkyl, or by an arylene group. For instance, a $C_{1-20}$ alkyl group such as n-butyl may be interrupted by the heterogroup N(R") as follows: —$CH_2N(R")CH_2CH_2CH_3$, —$CH_2CH_2N(R")CH_2CH_3$, or —$CH_2CH_2CH_2N(R")CH_3$. Similarly, an alkylene group such as n-butylene may be interrupted by the heterogroup N(R") as follows: —$CH_2N(R")CH_2CH_2CH_2$—, —$CH_2CH_2N(R")CH_2CH_2$—, or —$CH_2CH_2CH_2N(R")$ $CH_2$—. Typically an interrupted group, for instance an interrupted $C_{1-10}$ alkylene or $C_{1-20}$ alkyl group, is interrupted by 1, 2 or 3 heteroatoms or heterogroups, or by 1, 2 or 3 arylene (typically phenylene) groups. More typically, an interrupted group, for instance an interrupted $C_{1-10}$ alkylene or $C_{1-20}$ alkyl group, is interrupted by 1 or 2 heteroatoms or heterogroups, or by 1 or 2 arylene (typically phenylene) groups. For instance, a $C_{1-20}$ alkyl group such as n-butyl may be interrupted by 2 heterogroups N(R") as follows: —$CH_2N(R")$ $CH_2N(R")CH_2CH_3$.

An arylene group is an unsubstituted or substituted bidentate moiety obtained by removing two hydrogen atoms, one from each of two different aromatic ring atoms of an aromatic compound, which moiety has from 5 to 14 ring atoms (unless otherwise specified). Typically, each ring has from 5 to 7 or from 5 to 6 ring atoms. An arylene group may be unsubstituted or substituted, for instance, as specified above for aryl. Typically a substituted heteroarylene group carries 1, 2 or 3 substituents, for instance 1 or 2.

In this context, the prefixes (e.g., $C_{5-20}$, $C_{6-20}$, $C_{5-14}$, $C_{5-7}$, $C_{5-6}$, etc.) denote the number of ring atoms, or range of number of ring atoms, whether carbon atoms or heteroatoms. For example, the term "$C_{5-6}$ arylene," as used herein, pertains to an arylene group having 5 or 6 ring atoms. Examples of groups of arylene groups include $C_{5-20}$ arylene, $C_{6-20}$ arylene, $C_{5-14}$ arylene, $C_{6-14}$ arylene, $C_{6-10}$ arylene, $C_{5-12}$ arylene, $C_{5-10}$ arylene, $C_{5-7}$ arylene, $C_{5-6}$ arylene, $C_5$ arylene, and $C_6$ arylene.

The ring atoms may be all carbon atoms, as in "carboarylene groups" (e.g., $C_{6-20}$ carboarylene, $C_{6-14}$ carboarylene or $C_{6-10}$ carboarylene).

Examples of $C_{6-20}$ arylene groups which do not have ring heteroatoms (i.e., $C_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_{5-10}$ heteroarylene). A heteroarylene group may be unsubstituted or substituted, for instance, as specified above for aryl. Typically a substituted heteroarylene group carries 1, 2 or 3 substituents, for instance 1 or 2.

Examples of heteroarylene groups include, but are not limited to, those derived from the compounds discussed above in regard to heteroaryl groups. Examples of heteroarylene groups include bidentate groups derived from pyridine, pyrazine, pyrimidine, pyridazine, furan, thiofuran, pyrazole, pyrrole, oxazole, oxadiazole, isoxazole, thiadiazole, thiazole, isothiazole, imidazole and pyrazole.

A perfluoroarylene group is a perfluorinated arylene group. "Perfluorinated" in this context means completely fluorinated such that there are no carbon-bonded hydrogen atoms replaceable with fluorine. Typically it is tetrafluorophenylene.

As used herein the term halo is a group selected from —F, —Cl, —Br, and —I.

As used herein the term keto represents a group of formula: =O

As used herein the term nitro represents a group of formula: —$NO_2$

As used herein the term cyano represents a group of formula: —CN

As used herein the term hydroxyl represents a group of formula: —OH

As used herein the term thiol represents a group of formula: —SH

As used herein the term sulfonyl represents a group of formula: —S(O)$_2$R' wherein R' is a C$_{1-10}$ alkyl group, preferably a C$_{1-6}$ alkyl group, as defined previously.

As used herein the term acyl represents a group of formula: —C(=O)R, wherein R is an acyl substituent, for example, a substituted or unsubstituted C$_{1-20}$ alkyl group, a substituted or unsubstituted C$_{3-20}$ heterocyclyl group, or a substituted or unsubstituted aryl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

As used herein the term acyloxy (or reverse ester) represents a group of formula: —OC(=O)R, wherein R is an acyloxy substituent, for example, substituted or unsubstituted C$_{1-20}$ alkyl group, a substituted or unsubstituted C$_{3-20}$ heterocyclyl group, or a substituted or unsubstituted aryl group, typically a C$_{1-6}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

As used herein the term ester (or carboxylate, carboxylic acid ester or oxycarbonyl) represents a group of formula: —C(=O)OR, wherein R is an ester substituent, for example, a substituted or unsubstituted C$_{1-20}$ alkyl group, a substituted or unsubstituted C$_{3-20}$ heterocyclyl group, or a substituted or unsubstituted aryl group (typically a phenyl group). Examples of ester groups include, but are not limited to, —C(=O)OCH$_3$, —C(=O)OCH$_2$CH$_3$, —C(=O)OC(CH$_3$)$_3$, and —C(=O)OPh.

As used herein the term amino represents a group of formula —NH$_2$. The term C$_1$-C$_{10}$ alkylamino represents a group of formula —NHR' wherein R' is a C$_{1-10}$ alkyl group, preferably a C$_{1-6}$ alkyl group, as defined previously. The term di(C$_{1-10}$)alkylamino represents a group of formula —NR'R'' wherein R' and R'' are the same or different and represent C$_{1-10}$ alkyl groups, preferably C$_{1-6}$ alkyl groups, as defined previously. The term arylamino represents a group of formula —NHR' wherein R' is an aryl group, preferably a phenyl group, as defined previously. The term diarylamino represents a group of formula —NR'R'' wherein R' and R'' are the same or different and represent aryl groups, preferably phenyl groups, as defined previously. The term arylalkylamino represents a group of formula —NR'R'' wherein R' is a C$_{1-10}$ alkyl group, preferably a C$_{1-6}$ alkyl group, and R'' is an aryl group, preferably a phenyl group.

As used herein the term amido represents a group of formula: —C(=O)NR'R'', wherein R' and R'' are independently H or amino substituents, as defined for di(C$_{1-10}$)alkylamino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R' and R'', together with the nitrogen atom to which they are attached, form a heterocyclic structure as in, for example, piperidinocarbonyl, morpholinocarbonyl, thiomorpholinocarbonyl, and piperazinocarbonyl.

As used herein, the terms "carboxy", "carboxyl" and "carboxylic acid" each represent a group of the formula: —C(=O)OH, or —COOH. As would be understood by the skilled person, a carboxylic acid group (for instance, when employed in the present invention) can exist in protonated and deprotonated forms (for example, —C(=O)OH and —C(=O)(O$^-$), and in salt forms (for example, —C(=O)O$^-$X$^+$, wherein X$^+$ is a monovalent cation).

As used herein the term acylamido represents a group of formula: —NR$^x$C(=O)R$^y$, wherein R$^x$ is an amide substituent, for example, hydrogen, a C$_{1-20}$ alkyl group, a C$_{3-20}$ heterocyclyl group, an aryl group, preferably hydrogen or a C$_{1-20}$ alkyl group, and R$^y$ is an acyl substituent, for example, a C$_{1-20}$ alkyl group, a C$_{3-20}$ heterocyclyl group, or an aryl group, preferably hydrogen or a C$_{1-20}$ alkyl group. Examples of acylamide groups include, but are not limited to, —NHC(=O)CH$_3$, —NHC(=O)CH$_2$CH$_3$, —NHC(=O)Ph, —NHC(=O)C$_{15}$H$_{31}$ and —NHC(=O)C$_9$H$_{19}$. Thus, a substituted C$_{1-20}$ alkyl group may comprise an acylamido substituent defined by the formula —NHC(=O)—C$_{1-20}$ alkyl, such as —NHC(=O)C$_{15}$H$_{31}$ or —NHC(=O)C$_9$H$_{19}$. R$^x$ and R$^y$ may together form a cyclic structure, as in, for example, succinimidyl, maleimidyl, and phthalimidyl:

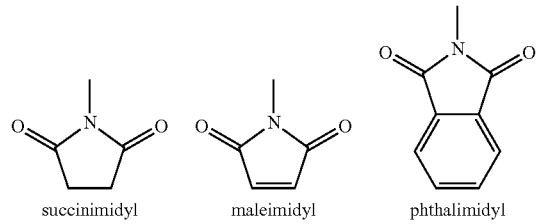

succinimidyl     maleimidyl     phthalimidyl

A C$_{1-10}$ alkylthio group is a said C$_{1-10}$ alkyl group, preferably a C$_{1-6}$ alkyl group, attached to a thio group. An arylthio group is an aryl group, preferably a phenyl group, attached to a thio group.

A C$_{1-20}$ alkoxy group is a said substituted or unsubstituted C$_{1-20}$ alkyl group attached to an oxygen atom. A C$_{1-10}$ alkoxy group is a said substituted or unsubstituted C$_{1-10}$ alkyl group attached to an oxygen atom. A C$_{1-6}$ alkoxy group is a said substituted or unsubstituted C$_{1-6}$ alkyl group attached to an oxygen atom. A C$_{1-4}$ alkoxy group is a substituted or unsubstituted C$_{1-4}$ alkyl group attached to an oxygen atom. Said C$_{1-20}$, C$_{1-10}$, C$_{1-6}$ and C$_{1-4}$ alkyl groups are optionally interrupted as defined herein. Examples of C$_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of C$_{1-20}$ alkoxy groups are —O(Adamantyl), —O—CH$_2$-Adamantyl and —O—CH$_2$—CH$_2$-Adamantyl. An aryloxy group is a substituted or unsubstituted aryl group, as defined herein, attached to an oxygen atom. An example of an aryloxy group is —OPh (phenoxy).

As used herein, the term "sulfonic acid" represents a group of the formula: —S(=O)$_2$OH. As would be understood by the skilled person, a sulfonic acid group can exist in protonated and deprotonated forms (for example, —S(=O)$_2$OH and —S(=O)$_2$O$^-$), and in salt forms (for example, —S(=O)$_2$O$^-$X$^+$, wherein X$^+$ is a monovalent cation).

As used herein, the term "sulfonamide" represents a group of formula: —S(O)$_2$NH$_2$.

The invention provides a functionalised compound of formula (II), as defined above, which comprises n carbene precursor groups of the following formula:

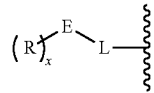

which are the same or different, wherein n is an integer equal to or greater than 3, E is a group which is capable of being converted into a carbene reactive intermediate group, x is 1, and R and L are as defined above.

The term "carbene precursor group", as used herein, means a latent reactive group which is capable of being converted into a carbene reactive intermediate by a chemical process or by the application of energy, wherein the carbene reactive intermediate is capable of further reaction. The "application of energy" may for instance involve the application of thermal energy (i.e. heating) or irradiation, although any suitable source of energy can be used.

An example of a carbene precursor group, E, which is capable of being converted into a carbene reactive intermediate, is a diazo group, as follows:

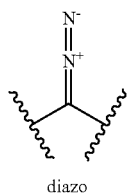 [SMILES: *C(*)=[N+]=[N-]]

diazo

Thus, E may be a diazo group.

A further example of a carbene precursor group, E, which is capable of being converted into a carbene reactive intermediate, is a hydrazone group of formula (1e″):

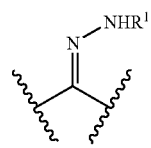

(1e″)

wherein $R^1$ is H or $-S(O)_2R^2$, wherein $R^2$ is an unsubstituted or substituted $C_{1-6}$ alkyl group or an unsubstituted or substituted aryl group.

Typically, $R^2$ is $C_{1-6}$ alkyl, phenyl or naphthyl, which phenyl or naphthyl is unsubstituted or substituted with $C_{1-6}$ alkyl, di($C_{1-6}$ alkyl)amino, hydroxyl, nitro, cyano or methoxy.

More typically, $R^2$ is $C_{1-6}$ alkyl, phenyl or naphthyl, which phenyl or naphthyl is unsubstituted or substituted with $C_{1-6}$ alkyl or di($C_{1-6}$ alkylamino.

Typically, $R^1$ is $-S(O)_2R^2$ wherein $R^2$ is phenyl substituted with $C_{1-6}$ alkyl. More typically, $R^1$ is $-S(O)_2R^2$ wherein $R^2$ is phenyl substituted with methyl (i.e. tolyl). Thus, in one embodiment, $R^1$ is a tosyl group. In another embodiment, $R^1$ is H.

Such hydrazone groups are "carbene precursor groups", because they are capable of conversion into carbene reactive intermediates. When $R^1$ is H this conversion may be achieved by oxidation of the hydrazone to a diazomethane followed by the application of energy, typically by heating or by irradiation. When $R^1$ is $-S(O)_2R^2$ conversion of the N sulfonylhydrazone group into the carbene reactive intermediate is achieved by treatment with a base followed by the application of energy, typically by heating or by irradiation. Any suitable base may be used, for instance an organic base such as a trialkyl amine (e.g. triethylamine) or 1,8-diazabicyclo[5.4.0]undec-7-ene (DBU). Alternatively an inorganic base may be used, such as an alkali metal hydroxide, e.g. sodium, lithium or potassium hydroxide. The decomposition of the sulfonyl hydrazone to the carbene is thought to occur by elimination of $R^1$, to form a diazo intermediate group, and subsequent elimination of dinitrogen to form the reactive carbene intermediate. Accordingly, E may be a hydrazone group of formula (1e″) as defined above.

Although each of the n carbene precursor groups in the functionalised compound of the invention falls within the formula

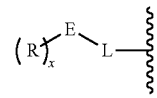

the groups E which are capable of being converted into carbene reactive intermediate groups, the linker groups (or single bonds) L, and/or the terminal groups R, may differ from one $[R]_x$-E-L- group to the next in the functionalised compound. For instance, the functionalised compound may comprise a first carbene precursor group of formula $[R]_x$-E-L- and a second carbene precursor group of formula $[R]_x$-E-L-, wherein the groups E which are capable of being converted into carbene reactive intermediate groups, the linker groups (or single bonds) L, and/or the terminal groups R are different in the first and second carbene precursor groups $[R]_x$-E-L-.

Accordingly, the n carbene precursor groups of the formula:

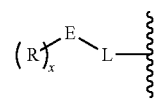

in the compound of formula (II) are the same or different and are independently selected from groups of the following formulae (Ia) and (Ie):

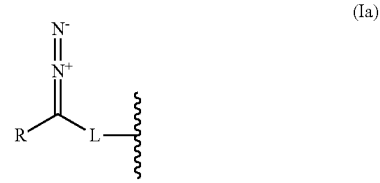

(Ia)

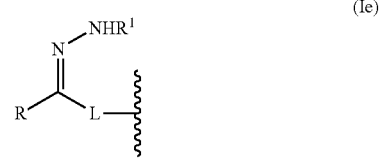

(Ie)

wherein R and L are as defined above and, in the group of formula (Ie), $R^1$ is as defined above.

Typically, however, E is the same group in all of the precursor groups in the functionalised compound. Similarly, L is typically the same in all of the precursor groups in the functionalised compound. Similarly, R is typically the same terminal group in all of the precursor groups in the compound.

The number of reactive intermediate precursor groups in the functionalised compound, n, is an integer equal to or greater than 3. In another embodiment, n is greater than or equal to 4.

In one embodiment, n is an integer of from 3 to 50 or, for instance, from 4 to 50. More typically n is an integer of from 3 to 20, from 3 to 10, from 4 to 20, or from 4 to 10, or an integer of 3, 4 or 5.

In another embodiment, however, n is an integer of from 3 to 500, or for instance from 4 to 500, and is more typically an integer of from 3 to 200, or for instance from 4 to 200, from 3 to 100, from 4 to 100, or from 10 to 100, for instance from 10 to 50.

In yet another embodiment, n is an integer equal to or greater than 50, for instance equal to or greater than 100. Thus, n may be an integer of from 50 to 1,000,000, from 50 to 100,000, from 50 to 10,000, from 50 to 5,000, or from 50 to 1,000. More typically, in this embodiment, n is an integer of from 50 to 1,000.

The functionalised compound of the invention is a compound of formula (II)

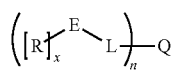
(II)

wherein n, x, L, R, E and Q are as defined herein.

The carbene precursor groups, E, which are capable of being converted into carbene reactive intermediate groups, the linker groups (or single bonds) L, and the terminal groups R, may differ from one $[R]_x$-E-L- group to the next in the functionalised compound, but are typically the same.

Thus, each of the $[R]_x$-E-L- groups in the functionalised compound of the invention of formula (II), which are the same or different, is independently selected from a group of formula (Ie) and a group of formula (Ia):

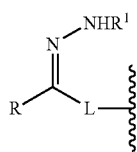
(Ie)

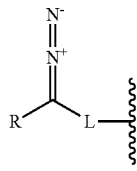
(Ia)

wherein R, L and $R^1$ are as defined above.

In one embodiment, the $[R]_x$-E-L- groups in the functionalised compound of the invention of formula (II) are hydrazone groups of formula (Ie).

Accordingly, in one embodiment, the invention provides a functionalised compound which is a hydrazone compound of formula (XXX)

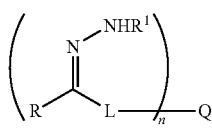
(XXX)

wherein:
n is an integer equal to or greater than 3;
R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)allylamino, arylamino, diarylamino, arylalkylamino, amido, acyl, acyloxy, acylamido, ester, $C_{1-10}$ alkoxy, aryloxy, haloalkyl, thiol, $C_{1-10}$ allylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;
each L, which is the same or different, is a single bond or a group of formula (XII)

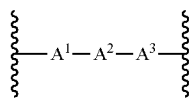
(XII)

wherein:
$A^1$ is bonded to the carbon atom bonded to R, wherein $A^1$ is an unsubstituted or substituted group selected from arylene and heteroarylene;
$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and
$A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$;
$R^1$ is H or —S(O)$_2R^2$, wherein $R^2$ is an unsubstituted or substituted $C_{1-6}$ alkyl group or an unsubstituted or substituted aryl group; and
Q is a core moiety, a polymer or a dendrimer;
with the proviso that when $R^1$ is H, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

The linker groups L, and the terminal groups R, may differ from one carbene precursor group to the next in the hydrazone compound, but are typically the same.

Typically, $R^2$ is an unsubstituted or substituted $C_{1-6}$ alkyl group, an unsubstituted or substituted phenyl group, or an unsubstituted or substituted naphthyl group. More typically, $R^2$ is $C_{1-6}$ alkyl, phenyl or naphthyl, which phenyl or naphthyl is unsubstituted or substituted with $C_{1-6}$ alkyl, di($C_{1-6}$ alkyl) amino, hydroxyl, nitro, cyano or methoxy. $R^2$ may for instance be $C_{1-6}$ alkyl, phenyl or naphthyl, which phenyl or naphthyl is unsubstituted or substituted with $C_{1-6}$ alkyl or di($C_{1-6}$ alkylamino.

In a preferred embodiment, the $[R]_x$-E-L- groups in the functionalised compound of the invention of formula (II) are sulfonylhydrazone groups, i.e. groups of formula (Ie) in which $R^1$ is $-S(O)_2R^2$, wherein $R^2$ is as defined above.

The ability to generate a carbene from a sulfonylhydrazone group without isolating the diazo group intermediate provides numerous advantages. Such sulfonylhydrazone groups are particularly advantageous because they are capable of being converted into a carbene reactive intermediate group, yet they are more stable than the diazo groups of formula (Ia). In particular, they act as a protected precursor to the carbene reactive intermediate and thereby allow a greater level of control over unwanted degradation of the functionalized compound of the invention, such as in transport or storage. Of particular significance is the decreased toxicity of a sulfonylhydrazone group over a diazo group. Sulfonylhydrazone groups also offer a greater flexibility with regards to formulation as they are not degraded by carboxylic acids unlike diazo groups such as diazo esters, diazo ketones and alkyl or aryl diazos.

Accordingly, in another embodiment the functionalised compound of the invention is a sulfonylhydrazone compound of formula (XXXa)

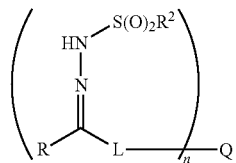

(XXXa)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ diaryl($C_{1-20}$ alkyl)silyl and triarylsilyl;

each L, which is the same or different, is a single bond or a group of formula (XII)

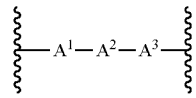

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$;

$R^2$ is an unsubstituted or substituted $C_{1-6}$ alkyl group or an unsubstituted or substituted aryl group; and Q is a core moiety, a polymer or a dendrimer.

The linker groups L, and the terminal groups R, may differ from one carbene precursor group to the next in the sulfonylhydrazone compound, but are typically the same.

Typically, in the functionalised compounds of the invention, $R^2$ is an unsubstituted or substituted $C_{1-6}$ alkyl group, an unsubstituted or substituted phenyl group, or an unsubstituted or substituted naphthyl group. More typically, $R^2$ is $C_{1-6}$ alkyl, phenyl or naphthyl, which phenyl or naphthyl is unsubstituted or substituted with $C_{1-6}$ alkyl, di($C_{1-6}$ alkyl)amino, hydroxyl, nitro, cyano or methoxy. $R^2$ may for instance be $C_{1-6}$ alkyl, phenyl or naphthyl, which phenyl or naphthyl is unsubstituted or substituted with $C_{1-6}$ alkyl or di($C_{1-6}$ alkylamino.

In one embodiment, $R^2$ is tolyl. Usually, $R^2$ is para-tolyl (in which case the —S(O)$_2R^2$ groups are tosyl groups).

In one embodiment, the $[R]_x$-E-L- groups in the functionalised compound of the invention of formula (II) are diazo groups of formula (Ia).

Accordingly, in another embodiment, the functionalised compound of the invention is a diazo-functionalised compound of formula (IIa)

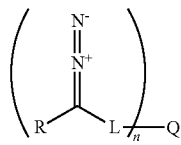

(IIa)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which may be the same or different, is a group of formula (XII)

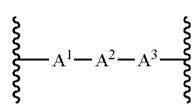

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a dendrimer or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

The linker groups L, and the terminal groups R, may differ from one carbene precursor group to the next in the diazo-functionalised compound, but are typically the same.

In another embodiment, the [R]$_x$-E-L- groups in the functionalised compound of the invention of formula (II) are hydrazone groups of formula (Ie) in which $R^1$ is H.

Accordingly, in another embodiment, the functionalised compound of the invention is a hydrazone compound of formula (XXXb)

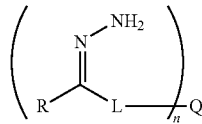

(XXXb)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which may be the same or different, is a group of formula (XII)

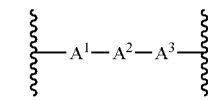

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a dendrimer or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

The linker groups L, and the terminal groups R, may differ from one carbene precursor group to the next in the hydrazone compound, but are typically the same.

The reactivity of the functionalised compound of the invention and its derived carbene reactive intermediate can be modified by including electron releasing or electron withdrawing groups on the aromatic aryl or heteroaryl ring of the terminal group R. In addition, the solubility of the functionalised compound and its derived carbene reactive intermediate can be modified by including groups of a given hydrophilicity or lipophilicity on the aromatic ring. Thus, in the functionalised compounds of the invention, each R group is selected from aryl and heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$)alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl.

More typically, R is phenyl which is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl.

In the functionalised compounds of the invention, each L, which is the same or different, is a single bond or a group of formula (XII)

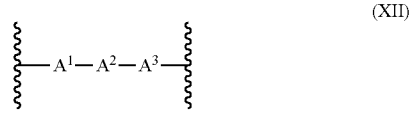

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$— $C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$.

Typically, $A^1$ is an unsubstituted or substituted arylene group. More typically, $A^1$ is an unsubstituted or substituted phenylene group, even more typically an unsubstituted phenylene group.

Usually, $A^2$ is an unsubstituted or substituted group selected from $C_{1-20}$ alkylene, $C_{1-20}$ perfluoroalkylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl. More typically, $A^2$ is $C_{1-10}$ alkylene or *—$C_{1-6}$ alkylene-(O— $C_{2-4}$ alkylene-)$_m$ wherein m is 1 to 20 and wherein * is the point of attachment of $A^2$ to $A^1$.

In one embodiment, $A^1$ is a phenylene group, typically an unsubstituted phenylene group, and $A^2$ is $C_{1-10}$ alkylene or *—$C_{1-6}$ alkylene-(O—$C_{2-4}$ alkylene-)$_m$ wherein m is 1 to 20 and wherein * is the point of attachment of $A^2$ to $A^1$.

Typically, $A^3$ is a single bond, O, C(O), *—OC(O) or an unsubstituted or substituted group selected from *—$Z^2$-arylene, *—$Z^2$-heteroarylene, arylene, heteroarylene, *—$Z^2$-arylene-O, *—$Z^2$-heteroarylene-O, *-arylene-O and *-heteroarylene-O, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$.

More typically, $A^3$ is a single bond, O, C(O), *—OC(O) or an unsubstituted or substituted group selected from *—O-arylene, *—O-heteroarylene, *—O-arylene-O and *—O-heteroarylene-O wherein * is the point of attachment of $A^3$ to $A^2$. Even more typically, $A^3$ is a single bond, O, or an unsubstituted or substituted group selected from *—O-arylene, *—O-heteroarylene, *—O-arylene-O and *—O-heteroarylene-O wherein * is the point of attachment of $A^3$ to $A^2$. Even more typically, $A^3$ is a single bond, O, or an unsubstituted or substituted group selected from *—O-heteroarylene and *—O-heteroarylene-O wherein * is the point of attachment of $A^3$ to $A^2$.

In one embodiment, each L within the functionalised compound of the invention is independently selected from the following groups:

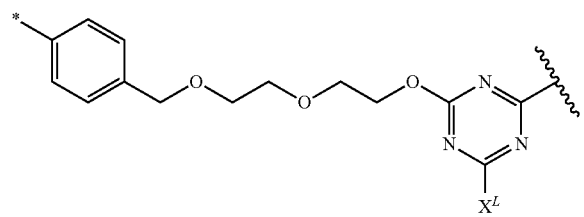

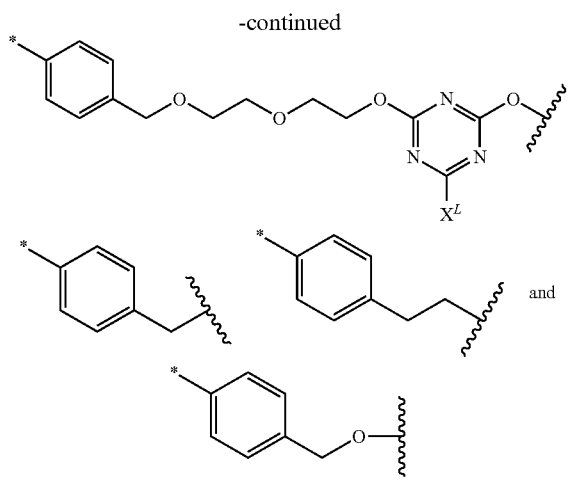

wherein * is the point of attachment of L to the carbon atom bonded to R, and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio.

Typically, $X^L$ is halo or hydroxyl. More typically, $X^L$ is halo, for instance chloro.

In some embodiments, wherein the functionalised compound of the invention comprises hydrazone groups of formula (Ie) in which $R^1$ is —S(O)$_2R^2$ (i.e. sulfonylhydrazone groups), L may be a single bond. In such embodiments, the carbon atoms of the carbene precursor groups (which carbon atoms are bonded to R) are bonded directly to Q.

Q is a core moiety, a polymer or a dendrimer. The core moiety, polymer or dendrimer is functionalised with said n carbene precursor groups [R]$_x$-E-L- in said compound of formula (II). As is shown in formula (II), each of the n reactive carbene precursor groups is bonded to the core moiety, polymer or dendrimer, Q, via the group L of the carbene precursor group, which may be a linking group or a single bond. When L is a group of formula (XII) as defined above, each of the n reactive intermediate precursor groups is typically bonded to the core moiety, polymer or dendrimer, Q, via group $A^3$ of said group of formula (XII).

As is described in further detail below, the functionalised compounds of formula (II) may be synthesised by coupling the carbene precursor groups (or carbonyl precursors thereto) to a core moiety, polymer or dendrimer Q' by reaction between a functional group on the linker moiety of the carbene precursor group (or on the carbonyl precursor) with functional groups, -$A^4$-$X^2$ on Q'. Thus, the core moiety, polymer or dendrimer Q of the compound of formula (II) is typically attached to the groups L of the n carbene precursor groups via n linker groups of formula $A^4$.

Accordingly, Q in the functionalised compounds of the invention is typically a core moiety, a polymer or a dendrimer which comprises n linker groups of formula $A^4$, each of which is attached to a group L, wherein n is an integer equal to or greater than 3. Each individual $A^4$ is the same as or different from the others and is independently selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —$Z^3$-arylene-O—*, —$Z^3$-heteroarylene-O—*, —$Z^3$—$C_{1-20}$ alkylene-O—*, arylene-O—*, heteroarylene-O—*, $C_{1-20}$ alkylene-O—*, —C(O)—*, S(O)$_2$, —OC(O)—*, —N(R'')C(O)—*, O, S, N(R''), —C(O)O—*, —C(O)N(R'')—*, —S(O)$_2$O—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R''), C(O), S(O), S(O)$_2$, C(O)O, OC(O), C(O)N(R'') and N(R'')C(O), wherein each R'' is independently selected from H, $C_{1-6}$ alkyl and aryl, and wherein * is the point of attachment of $A^4$ to L.

In one embodiment, each $A^4$ is independently selected from O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ alkylene-O—*, wherein $Z^3$ is selected from O, S, N(R''), C(O), S(O), S(O)$_2$, C(O)O, OC(O), C(O)N(R'') and N(R'')C(O), wherein each R'' is independently selected from H, $C_{1-6}$ alkyl and aryl, wherein * is the point of attachment of $A^4$ to L. More typically, in this embodiment, $A^4$ is O.

In another embodiment, each $A^4$ is independently selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —C(O)—, S(O)$_2$, —OC(O)—*, —N(R'')C(O)—*, $C_{1-20}$ alkenylene, $C_{1-20}$ alkynylene, —$Z^3$—$C_{1-20}$ alkenylene-* and —$Z^3$—$C_{1-20}$ allynylene-*, wherein $Z^3$ is selected from O, S, N(R''), C(O), S(O), S(O)$_2$, C(O)O, OC(O), C(O)N(R'') and N(R'')C(O), wherein each R'' is independently selected from H, $C_{1-6}$ alkyl and aryl, and wherein * is the point of attachment of $A^4$ to L.

In a further embodiment, $A^4$ is —C(O)—.

In another embodiment, $A^4$ is —$Z^3$-heteroarylene-* wherein * is the point of attachment of $A^4$ to L. Typically, $Z^3$ is O. Typically, in this embodiment, $A^4$ is a group of formula (XIX)

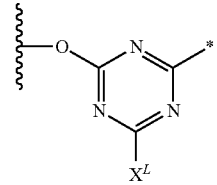

(XIX)

wherein * is the point of attachment to L and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio.

Typically, $X^L$ is halo or hydroxyl. More typically, $X^L$ is halo, for instance chloro.

In one embodiment, Q is a dendrimer, which dendrimer comprises n surface groups which are linker groups of formula $A^4$ as defined above. The n linker groups $A^4$ are the same as or different from one another and bonded to the n L groups of the n carbene precursor groups [R]$_x$-E-L- in said compound of formula (II). Any suitable dendrimer structure may be employed. When Q is a dendrimer, n is typically an integer of from 3 to 500, or from 4 to 500, and is more typically an integer of from 3 to 200, or from 4 to 200, from 3 to 100, or from 4 to 100, or from 10 to 100, for instance from 10 to 50.

Any suitable dendrimer may be used. PAMAM dendrimers are suitable, for instance.

When Q comprises a polymer, the polymer may be a linear polymer, a branched polymer or a hyperbranched polymer. The polymer may for instance be a homopolymer or a copolymer. The co-polymer may be a ter-polymer or any other multiple combination polymer. Suitable copolymers include polymethylmethacrylate-co-poly-2-dimethylamino ethyl methacrylate, for instance.

Also covered are different polymer architectures, including but not limited to branched polymers; block copolymers, for instance, SBS rubber (Kraton), or EO-PO-EO (Pluronic); star polymers (Tetronic); or hyperbranched polymers (PEI).

Polymers of different molecular weight ranges are also covered, from small macromers with a repeat unit length of a dimer, to polymers with a molecular weight of millions. The degree of polymerisation, Dp, of the polymer (i.e. the polymer molecular weight divided by the molecular weight of the repeat unit) may be from 2 to 100,000,000.

Typically, the polymer employed is either soluble or dispersable.

When Q comprises a polymer, the polymer may be a homopolymer or a copolymer.

In one embodiment, when Q comprises a polymer, the polymer is selected from any of the polymers listed in the following paragraph and their copolymers. Thus, the polymer may be a homopolymer comprising any of the following polymers, or a copolymer which comprises the monomeric units of any one or more of the following polymers:

Condensation polymers and Addition polymers. Polysaccharides, including but not limited to chitin, guar gums, gum arabic, galactomannans, for instance locust bean gum (LBG). Proteins, including but not limited to Keratin. Polyesters, including but not limited to Nylon, polyethylene terephthalate (PET) and polyoxyethylene terephthalate (POET). Polyethers, including but not limited to polypropylene glycol (PPG), polyethylene gloycol (PEG), Polyethylene oxide (PEO). Polyolefins, including but not limited to polyethylene (PE), polypropylene (PP), and co-polymers thereof. Polyolefin co-polymers. Polyacrylates and polymethacrylates, including but not limited to polyacric acid (PAA) polymethacrylic acid (PMAA), Poly2-dimethylamino methacrylate (PDMAEMA), Poly-2-hydroxyethyl methacylate (PHEMA), acrylonitrile. Polystyrene. Thermoplatic elastomers, including but not limited to, Polybutadiene, Polyisoprene, SBS rubber and SIS rubber. Polycarbonates. Polyetheretherketone (PEEK). Polyetherimides. Polyimides. Polysulfones. Poly vinyl chloride (PVC). Polysilanes. Polysiloxanes. Polyureas. Polyurethanes. Polylactic acid. Polyvinylidene chloride. Polyethylene imines.

When Q comprises a polymer, the polymer may be a salt of any of the polymers described herein.

In some embodiments, when Q comprises a polymer, the polymer comprises a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

Typically, the polymer is one that has a functionality -$A^4$-$X^2$ as defined herein, for instance an OH, NH, SH or aryl (typically phenyl) functionality that allows single step transformation to introduce the reactive intermediate precursor groups of formula (I) onto the polymer.

Alternatively, however, any polymer can be modified to include the reactive intermediate precursor group using a two-step process. In such a process, an -$A^4$-$X^2$ functionality, for instance an —OH, NH, SH or aryl (typically phenyl) functionality is first reacted onto the desired polymer. Subsequently, that -$A^4$-$X^2$ functionality, which has been newly-introduced on the polymer, is coupled with a further compound, which comprises the reactive intermediate precursor group of formula (I), to introduce that reactive intermediate precursor group onto the polymer.

Thus, when Q comprises a polymer, for instance any of the polymers defined above, the polymer typically comprises n linker groups of formula $A^4$ which are the same or different and are as defined above, each of which is attached to a group L of a reactive intermediate precursor group of formula (I), wherein n is an integer equal to or greater than 2.

In one embodiment, $A^4$ is O or —$Z^3$-heteroarylene-* wherein * is the point of attachment of $A^4$ to L. Typically, $Z^3$ is O. More typically, in this embodiment, $A^4$ is O or a group of formula (XIX) as defined above.

In one embodiment, Q comprises a polysaccharide, a polyester or polystyrene.

In one embodiment, when Q comprises a polysaccharide, the polysaccharide is a chitin, guar gum, gum arabic, or a galactomannan, for instance locust bean gum (LBG).

In one embodiment, when Q comprises a polyester, the polyester is Nylon, polyethylene terephthalate (PET) or polyoxyethylene terephthalate (POET).

As mentioned above, in some embodiments of the functionalised compound of the invention, L may be a single bond.

Typically, when L is a single bond, Q comprises at least n aryl or heteroaryl rings, wherein each L which is single bond is attached directly to a said aryl or heteroaryl ring of Q. The single bond, L, thereby bonds the aryl or heteroaryl ring directly to the carbon atom of the carbene precursor group (i.e. the carbon atom that is also bonded to R in the functionalised compound of the invention). In this embodiment Q is a core moiety, polymer or dendrimer that comprises said n aryl or heteroaryl rings. Typically, said aryl or heteroaryl rings are aryl rings. Usually, said aryl rings are phenyl rings. Examples of polymers that comprise aryl rings include, for instance, polystyrene, a copolymer comprising polystyrene, a thermoplastic elastomer, polyisoprene, a copolymer comprising polyisoprene, SBS rubber, SIS rubber or poly(styrene)-poly (ethylene/butylene)-poly(styrene) (SEBS).

More typically, when L is a single bond, Q is a polymer which comprises at least n aryl or heteroaryl rings, wherein each L which is single bond is attached directly to a said aryl or heteroaryl ring, thereby bonding the aryl or heteroaryl ring directly to the carbon atom which is bonded to R. Typically, said aryl or heteroaryl rings are aryl rings. Typically, said aryl rings are phenyl rings.

Thus, in some embodiments of the functionalised compound of the invention, L is a single bond and Q is a polymer which comprises at least n aryl or heteroaryl rings, wherein each L which is single bond is attached directly to a said aryl or heteroaryl ring, thereby bonding the aryl or heteroaryl ring directly to the carbon atom which is bonded to R. Typically, said aryl or heteroaryl rings are aryl rings. Typically, said aryl rings are phenyl rings. Usually, in such embodiments, Q comprises polystyrene, a copolymer comprising polystyrene, a thermoplastic elastomer, polyisoprene, a copolymer comprising polyisoprene, SBS rubber, SIS rubber or poly(styrene)-poly(ethylene/butylene)-poly(styrene) (SEBS).

Typically, when Q comprises a polymer, n is an integer equal to or greater than 50, for instance equal to or greater than 100. Thus, n may be an integer of from 50 to 1,000,000, from 50 to 100,000, from 50 to 10,000, from 50 to 5,000, or from 50 to 1,000. More typically, in this embodiment, n is an integer of from 50 to 1,000.

In one embodiment, Q is a core moiety which is a straight-chained or branched, saturated or unsaturated $C_{1-20}$ hydrocarbon moiety; an aryl ring; a heteroaryl ring; a $C_{5-10}$ carbocyclic ring; a $C_{5-10}$ heterocyclic ring; or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring;

wherein said hydrocarbon moiety, aryl ring, heteroaryl ring, carbocyclic ring, heterocyclic ring or fused bi-, tri- or tetracyclic ring system is substituted with said n linker groups, $A^4$, and is otherwise unsubstituted or substituted, wherein each $A^4$ is the same or different and is as defined hereinbefore and wherein each $A^4$ is attached to a group L.

Typically, when Q is a core moiety, n is an integer of from 3 to 50, or from 4 to 50, more typically an integer of from 3 to 20, or from 4 to 20, or from 3 to 10, or from 4 to 10, or an integer of 3, 4 or 5.

Typically, n is an integer of from 3 to 10 and Q is a core moiety of formula (XIV):

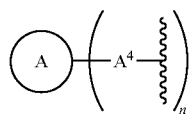

(XIV)

wherein each $A^4$ is the same or different and is as defined above, and wherein A is an aryl ring, a heteroaryl ring, a $C_{5-10}$ carbocyclic ring, a $C_{5-10}$ heterocyclic ring, or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring.

Typically, in this embodiment, A is an aryl ring or a heteroaryl ring. Typically, n is an integer of from 3 to 6.

In another embodiment, n is an integer of from 3 to 10 and Q is a core moiety of formula (XVI):

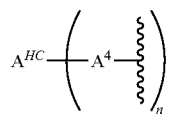

(XVI)

wherein each $A^4$ is the same or different and is as defined above, and wherein $A^{HC}$ is straight-chained or branched, saturated or unsaturated $C_{1-20}$ hydrocarbon moiety which is otherwise unsubstituted or substituted.

Typically, in this embodiment, n is an integer of from 3 to 6.

Typically, the $C_{1-20}$ hydrocarbon moiety is a straight-chained or branched $C_{1-10}$ hydrocarbon moiety which is substituted with said n $A^4$ linkers and is otherwise unsubstituted or substituted. For instance, it may be a methane, ethane, propane, butane, pentane, hexane, heptane, octane, nonane or decane moiety which is substituted with said n $A^4$ linkers and otherwise unsubstituted or substituted. The hydrocarbon may be straight-chained or branched. Thus, for instance, a propane hydrocarbon moiety may be i-propane or n-propane and a butane moiety may be t-butane, s-butane, i-butane or n-butane.

In one embodiment, n is 3.

In one embodiment, n is 3 and Q is a core moiety of formula (XIVa)

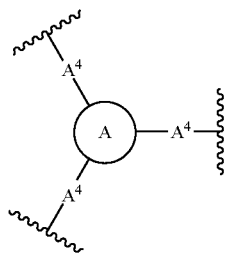

(XIVa)

wherein each $A^4$ is the same or different and is as defined hereinbefore and wherein A is an aryl or heteroaryl ring. Typically, in this embodiment, each $A^4$ is independently selected from C(O), O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ alkylene-O—*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, wherein * is the point of attachment of $A^4$ to L. More typically, in this embodiment, each $A^4$ is independently selected from C(O) and O. Even more typically, in this embodiment, $A^4$ is C(O).

In another embodiment, n is 3 and Q is a core moiety of formula (XVIa)

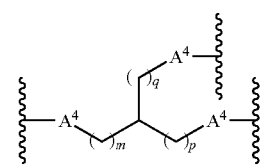

(XVIa)

wherein $A^4$ is the same or different and is as defined hereinbefore and wherein q, m and p are the same or different and are independently selected from 0 and an integer of 1 to 20. Typically, in this embodiment, each $A^4$ is independently selected from C(O), O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ alkylene-O—*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, wherein * is the point of attachment of $A^4$ to L. More typically, in this embodiment, each $A^4$ is independently selected from C(O) and O. Even more typically, in this embodiment, $A^4$ is O.

In another embodiment, n is 3 and Q is any one of the following core moieties:

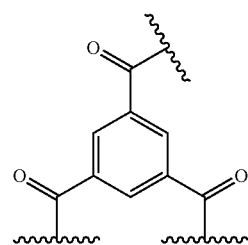

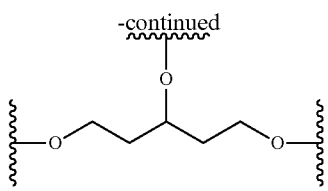

In one embodiment of the functionalised compound of the invention, L is a group of formula (XII) as defined above, in which $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, C(O), S(O)$_2$, *—OC(O) and *—N(R")C(O), wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$.

Typically, in this embodiment, $A^3$ is a single bond.

Alternatively, $A^3$ may be an unsubstituted or substituted group selected from *—O-arylene and *—O-heteroarylene wherein * is the point of attachment of $A^3$ to $A^2$. For instance, $A^3$ may be a group of formula (XVII)

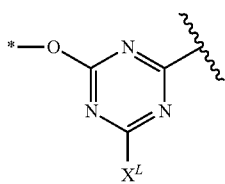

(XVII)

wherein * is the point of attachment of $A^3$ to $A^2$, and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio.

Typically, $X^L$ is halo or hydroxyl. More typically, $X^L$ is halo, for instance chloro.

Typically, when $A^3$ is an unsubstituted or substituted group selected from *—O-arylene and *—O-heteroarylene, $A^1$ is unsubstituted or substituted phenylene and $A^2$ is an unsubstituted or substituted group selected from $C_{1-20}$ alkylene, $C_{1-20}$ perfluoroalkylene, *—$C_{1-20}$ alkylene-(O—$C_{1-20}$ alkylene-)$_m$, wherein m is 1 to 20, *—$Z^1$—$C_{1-20}$ alkylene, *—$Z^1$—$C_{1-20}$ perfluoroalkylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl. More typically, in this embodiment, $A^1$ is unsubstituted or substituted phenylene and $A^2$ is $C_{1-10}$ alkylene or *—$C_{1-20}$ alkylene-(O—$C_{1-20}$ alkylene-)$_m$ wherein m is 1 to 20 and wherein * is the point of attachment of $A^2$ to $A^1$. Even more typically $A^2$ is *—$C_{1-6}$ alkylene-(O—$C_{2-4}$ alkylene-)$_m$ wherein m is 1 to 20 and wherein * is the point of attachment of $A^2$ to $A^1$. Usually, in these embodiments, $A^3$ is a group of formula (XVII)

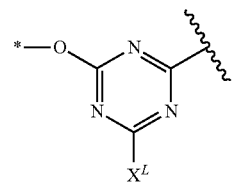

wherein * is the point of attachment of $A^3$ to $A^2$ and wherein $X^L$ is as defined above. Thus, L may for instance be the following group:

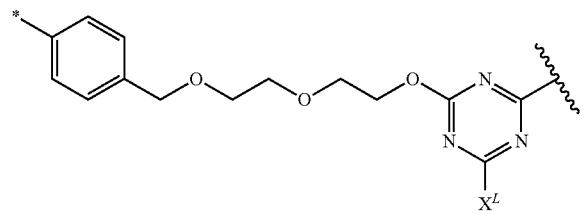

wherein * is the point of attachment of L to the carbon atom bonded to R and wherein $X^L$ is as defined above.

When $A^3$ is a single bond, $A^1$ is typically unsubstituted or substituted phenylene and $A^2$ is typically unsubstituted or substituted $C_{1-20}$ alkylene, for instance unsubstituted or substituted $C_{1-10}$ alkylene, unsubstituted or substituted $C_{1-4}$ alkylene or CH$_2$. Thus, L may for instance be the following group:

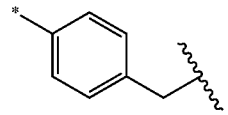

wherein * is the point of attachment of L to the carbon atom bonded to R.

In another embodiment, when $A^3$ is a single bond, $A^1$ and $A^2$ are also single bonds and therefore L itself is a single bond. Typically, in this embodiment, each L is attached to a phenyl group of Q. Typically, in this embodiment, Q is a core moiety, polymer or dendrimer bearing phenyl groups, more typically a polymer bearing phenyl groups, for instance polystyrene.

Typically, when L is a group of formula (XII) as defined above, in which $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, C(O), S(O)$_2$, *—OC(O) and *—N(R")C(O), as defined above, or in which $A^3$ is as further defined in the preceding paragraphs, Q is a core moiety, polymer or dendrimer comprising n linker atoms which are oxygen atoms, wherein each of said oxygen atoms is attached to a group L.

Typically, in this embodiment, Q is a polysaccharide. For instance Q may be chitin, a guar gum, gum arabic or a galactomannan, for instance locust bean gum (LBG). Such polysaccharides bear terminal OH groups which can be converted into said n linker atoms which are oxygen atoms.

Alternatively Q may be a core moiety of formula (XIV) or formula (XVI):

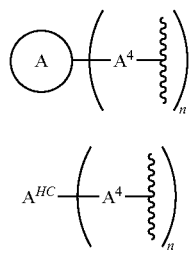

(XIV)

(XVI)

wherein n is an integer of 3 to 10, wherein A and $A^{HC}$ are as defined above, and wherein each $A^4$, which is the same or different, is independently selected from O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ alkylene-O—*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, wherein * is the point of attachment of $A^4$ to L.

Alternatively Q may be a core moiety of formula (XIVa) or formula (XVIa)

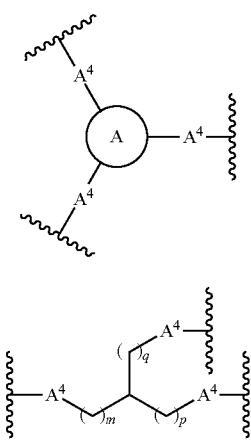

(XIVa)

(XVIa)

wherein

A is an aryl or heteroaryl ring;

q, m and p are the same or different and are independently selected from 0 and an integer of 1 to 20; and each $A^4$, which is the same or different, is independently selected from O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ allylene-O—*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, wherein * is the point of attachment of $A^4$ to L.

Q may for instance be any one of the following core moieties:

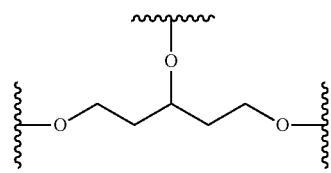

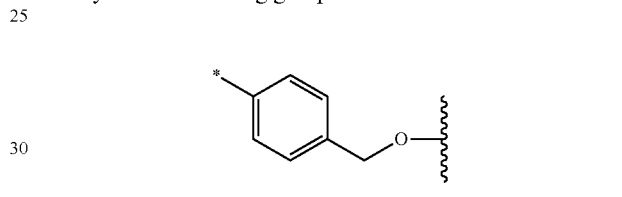

In another embodiment of the functionalised compound of the invention, L is a group of formula (XII) as defined above, in which $A^3$ is O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene or *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$. Typically, in this embodiment, $A^3$ is O. Typically, in this embodiment, $A^1$ is unsubstituted or substituted phenylene. $A^2$ is typically any $A^2$ group as defined hereinbefore. However, $A^2$ is more typically $C_{1-20}$ alkylene. Typically, therefore $A^1$ is unsubstituted or substituted phenylene, $A^2$ is $C_{1-20}$ alkylene and $A^3$ is O. Thus, L may be the following group

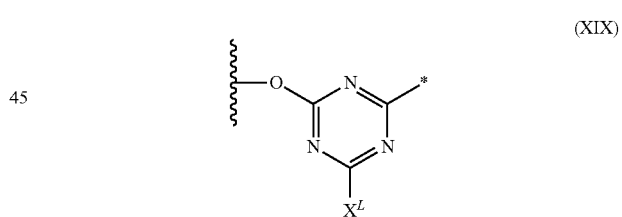

wherein * is the point of attachment of L to the carbon atom bonded to R.

Typically, in the embodiments defined in the preceding paragraph, Q is a core moiety, polymer or dendrimer which bears n linker groups, each of which is attached to a group L, which linker groups are of formula (XIX)

(XIX)

wherein * is the point of attachment to L, and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio. Typically, $X^L$ is halo or hydroxyl. More typically, $X^L$ is halo, for instance chloro. Thus, Q may be a polysaccharide or a polyester which bears said n linker groups of formula (XIX). Typically, Q is a polyester which bears said n linker groups. The polyester may for instance be Nylon, polyethylene terephthalate (PET) or polyoxyethylene terephthalate (POET).

Alternatively Q may be a core moiety of formula (XIV) or formula (XVI):

(XIV)

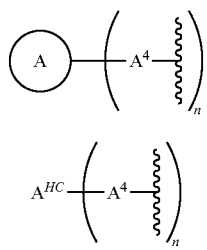

(XVI)

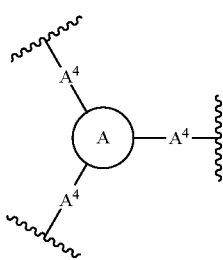

wherein n is an integer of 3 to 10, wherein A and $A^{HC}$ are as defined above, and wherein each $A^4$, which is the same or different, is selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —C(O)—*, S(O)$_2$, —OC(O)—*, —N(R")C(O)—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^4$ to L.

Alternatively, Q may be a core moiety of formula (XIV) or formula (XVI)

(XIV)

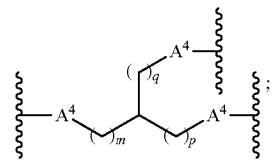

-continued (XVI)

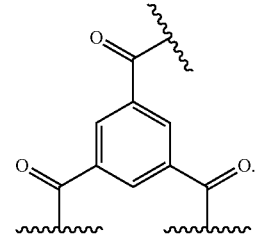

wherein
A is an aryl or heteroaryl ring;
q, m and p are the same or different and are independently selected from 0 and an integer of 1 to 20; and
each $A^4$, which is the same or different, is selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —C(O)—*, S(O)$_2$, —OC(O)—*, —N(R")C(O)—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^4$ to L.

In one embodiment, $A^4$ is C(O). Thus, Q may be the following core moiety:

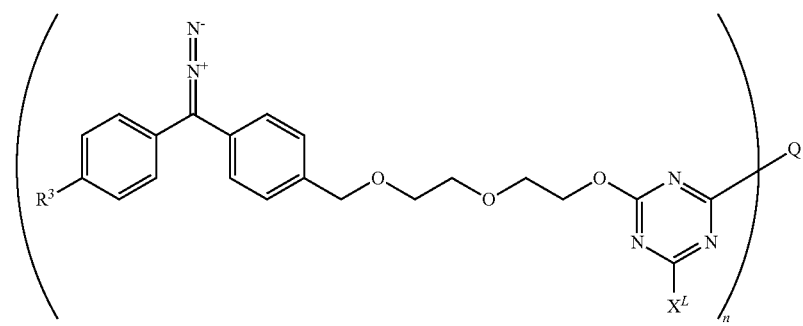

In one embodiment, the functionalised compound is of formula (XX), formula (XXa), or formula (XXb)

(XX)

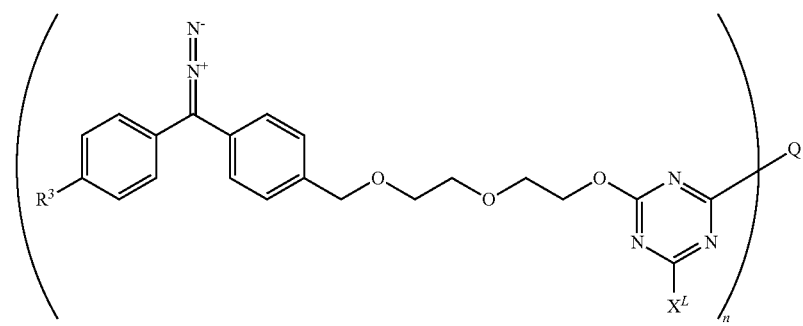

(XXa)

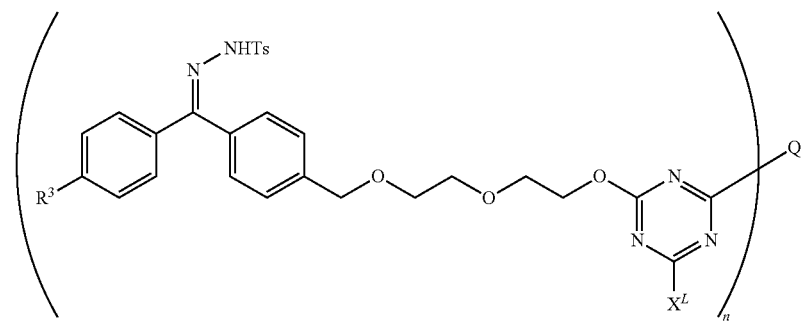

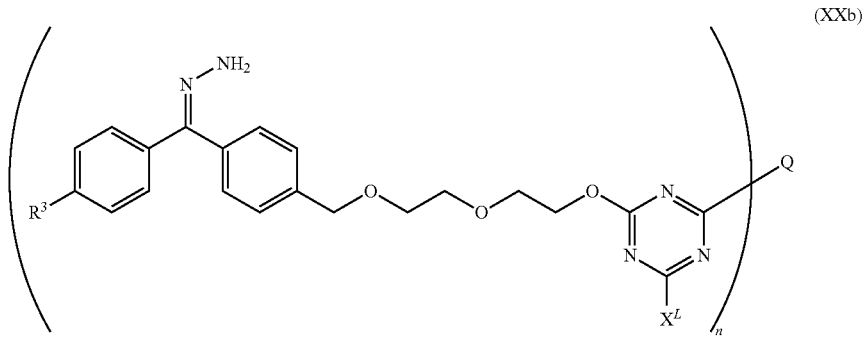

(XXb)

wherein n, Q and $X^L$ are as defined hereinbefore and $R^3$ is $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$) alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl or triarylsilyl. More typically, $R^3$ is H or $NO_2$. Even more typically, $R^3$ is $NO_2$. Typically, $X^L$ is halo or hydroxyl. More typically, $X^L$ is halo, for instance chloro. Typically, Q comprises a polymer and n is an integer equal to or greater than 50. Typically, the polymer is a polysaccharide, for instance a galactomannan, e.g. locust bean gum. Alternatively, the polymer may be a polyester, for instance nylon, polyethylene terephthalate (PET) or polyoxyethylene terephthalate (POET).

Typically, the functionalised compound is of formula (XXa).

In another embodiment, the functionalised compound is of formula (XXI), formula (XXIa), or formula (XXIb)

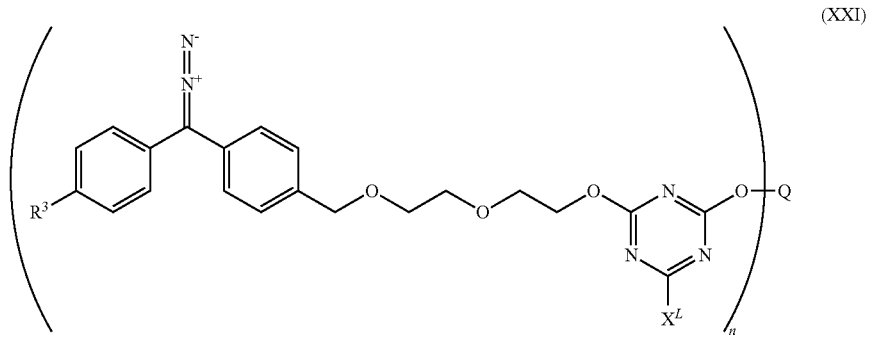

(XXI)

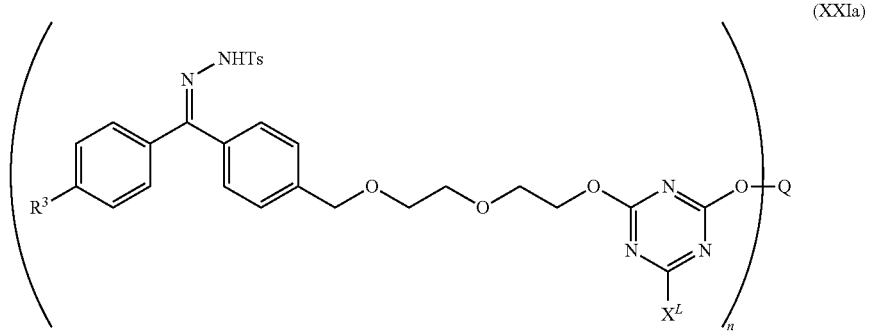

(XXIa)

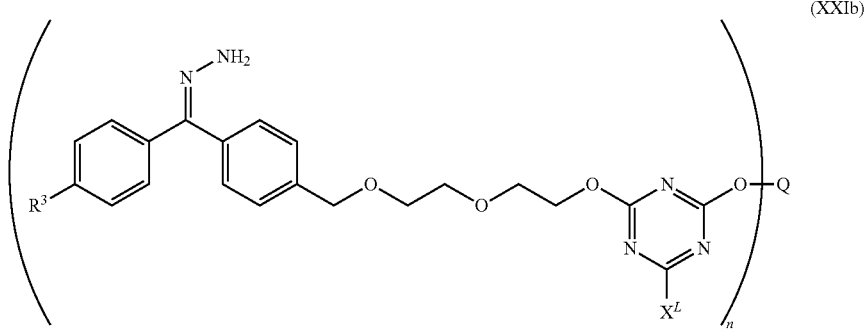

(XXIb)

wherein n, Q, $R^3$ and $X^L$ are as defined hereinbefore. Typically, $R^3$ is H or $NO_2$. Even more typically, $R^3$ is $NO_2$. Typically, $X^L$ is halo or hydroxyl. More typically, $X^L$ is halo, for instance chloro. Typically, Q comprises a polymer and n is an integer equal to or greater than 50. Typically, the polymer is a polysaccharide, for instance a galactomannan, e.g. locust bean gum. Alternatively, the polymer may be a polyester, for instance nylon, polyethylene terephthalate (PET) or polyoxyethylene terephthalate (POET).

Typically, the functionalised compound is of formula (XXIa).

In another embodiment, the functionalised compound is of formula (XXII), (XXIIa) or (XXIIb)

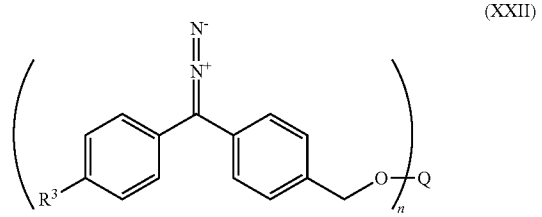

(XXII)

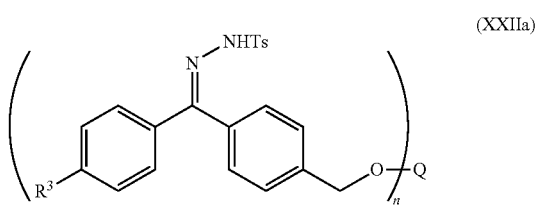

(XXIIa)

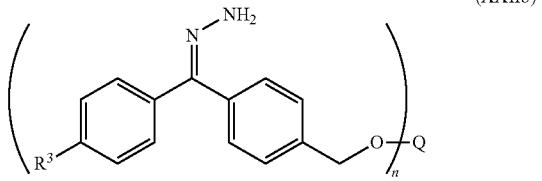

(XXIIb)

wherein n, Q and $R^3$ are as defined hereinbefore. Typically, $R^3$ is H or $NO_2$. In one embodiment Q comprises a polymer and n is an integer equal to or greater than 50. The polymer may for instance be a polysaccharide, for instance a galactomannan, e.g. locust bean gum. Alternatively Q may be a polyester which bears n linker groups of formula (XIX) as defined hereinbefore. In another embodiment, Q is a core moiety as defined hereinbefore. Typically, when Q is a core moiety n is an integer of from 3 to 50, or from 3 to 10. More typically, when Q is a core moiety n is 3. Q may for instance be the following core moiety, wherein n is 3:

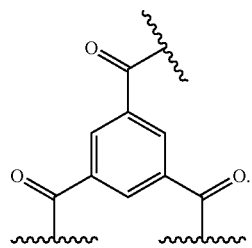 [SMILES: *C(=O)c1cc(C(*)=O)cc(C(*)=O)c1]

In another embodiment, the functionalised compound is of formula (XXIII), (XXIIIy) or (XXIIIz)

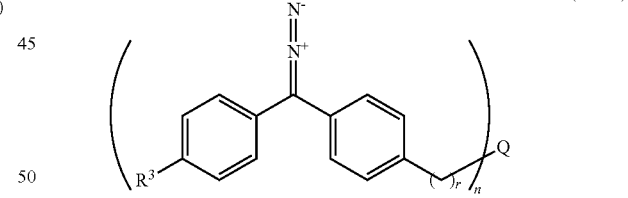

(XXIII)

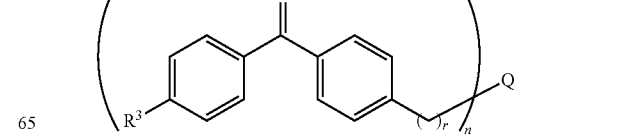

(XXIIIy)

(XXIIIz)

wherein r is an integer of from 1 to 4 and each r is the same or different, and n, Q and $R^3$ are as defined hereinbefore. Typically, $R^3$ is H or $NO_2$. In one embodiment Q comprises a polymer and n is an integer equal to or greater than 50. The polymer may for instance be a polysaccharide, for instance a galactomannan, e.g. locust bean gum. In another embodiment, Q is a core moiety as defined hereinbefore. Typically, when Q is a core moiety n is an integer of from 3 to 50. More typically, when Q is a core moiety n is an integer of from 3 to 10. More typically, when Q is a core moiety n is 3. Q may for instance be any one of the following core moieties, wherein n is 3:

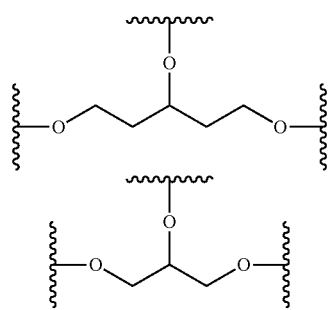

In another embodiment, the functionalised compound is a compound of formula (XXIV) or (XXV)

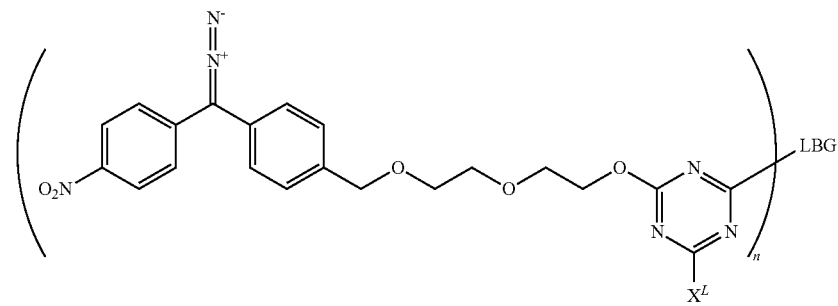

(XXIV)

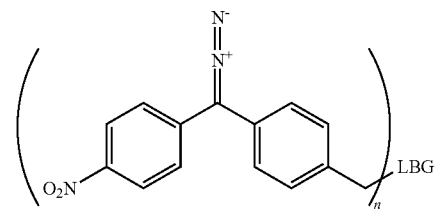

(XXV)

wherein n is an integer equal to or greater than 50 and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, aryalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ allylthio or arylthio. Typically, $X^L$ is halo or hydroxyl. More typically, $X^L$ is halo, for instance chloro.

In another embodiment, the functionalised compound is a compound of formula (XXIVa) or (XXVa)

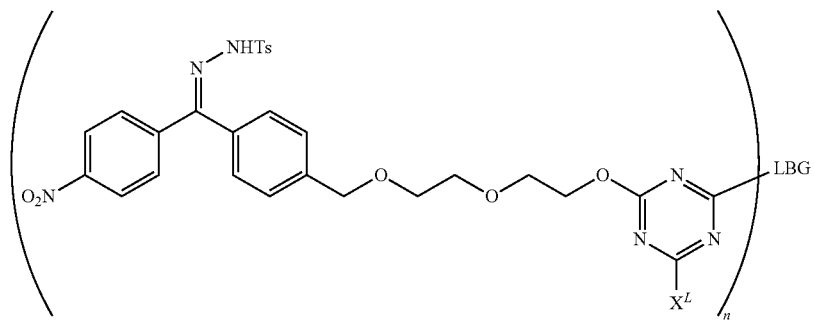

(XXIVa)

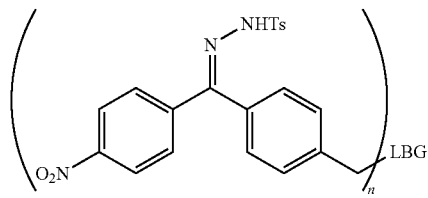

(XXVa)

wherein n is an integer equal to or greater than 50 and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio. Typically, $X^L$ is halo or hydroxyl. More typically, $X^L$ is halo, for instance chloro.

In another embodiment, the functionalised compound is a compound of formula (XXVII), (XXVIIa) or (XXVIII)

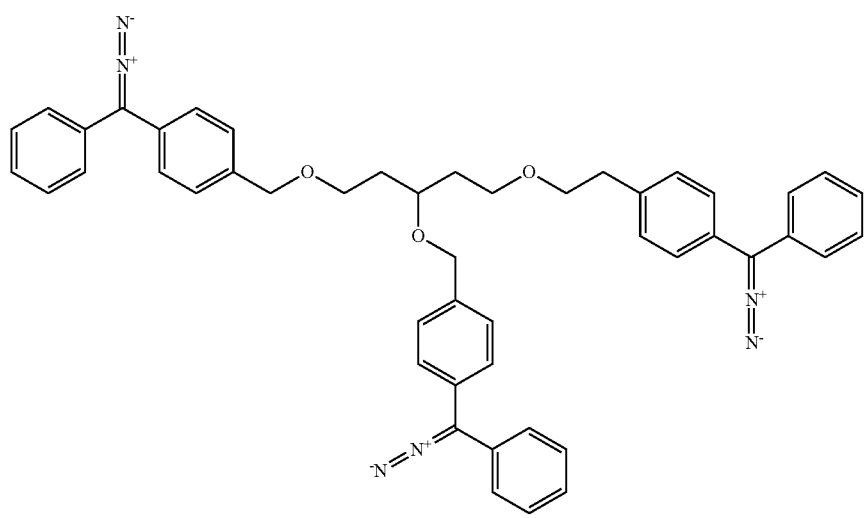

(XXVII)

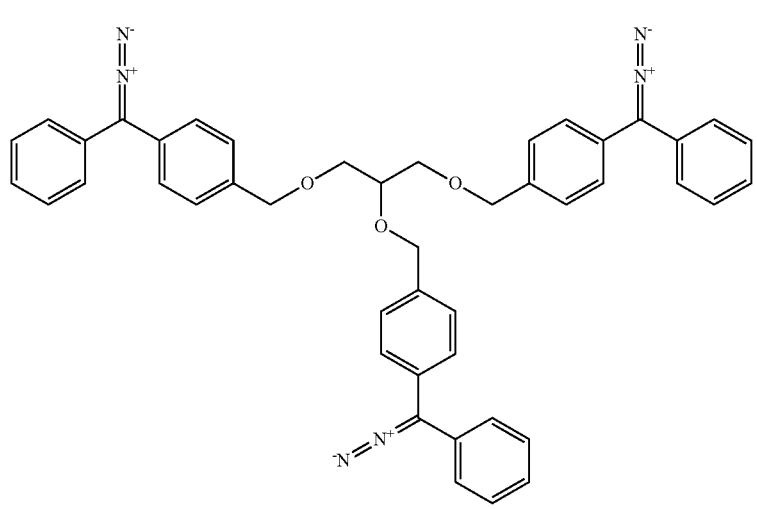

(XXVIIa)

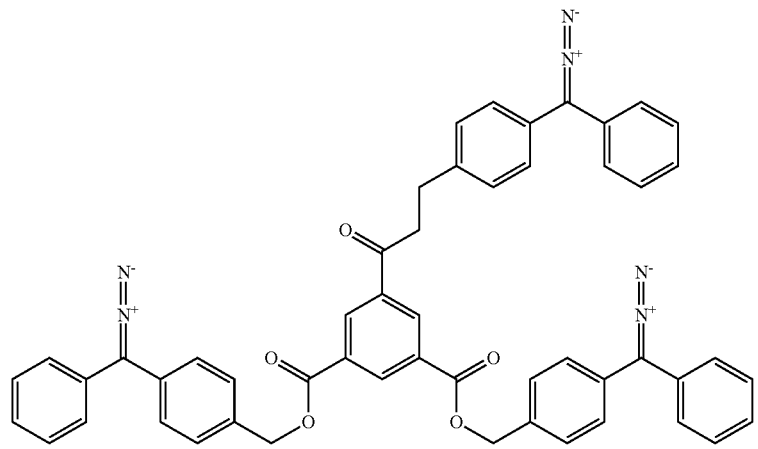
(XXVIII)
In another embodiment, the functionalised compound is a compound of formula (XXVIIb) or (XXVIIc)
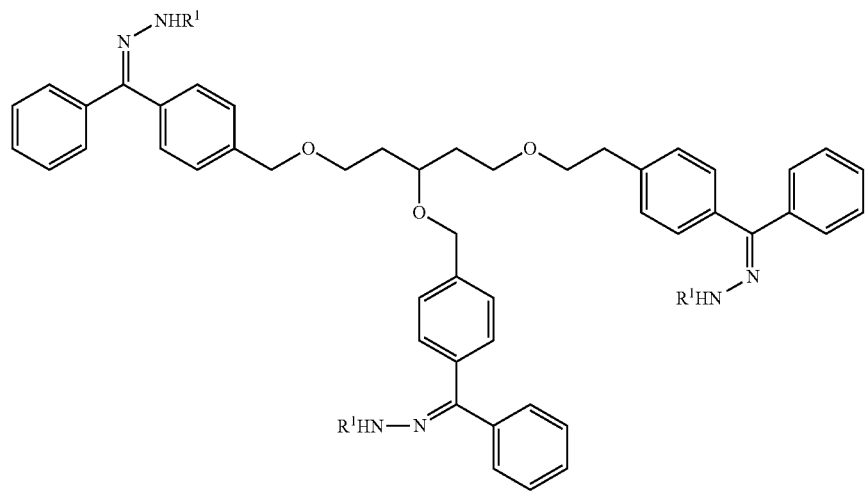
(XXVIIb)
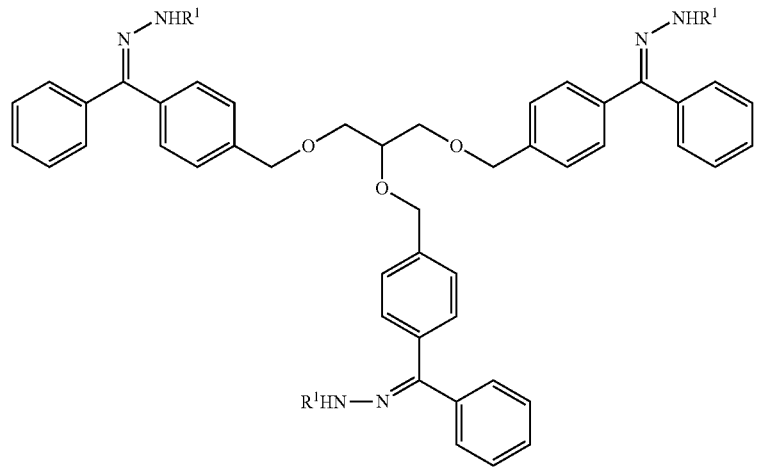
(XXVIIc)
wherein $R^1$ is H or tosyl.

In another embodiment, the functionalised compound is a compound of formula (XXVIb)

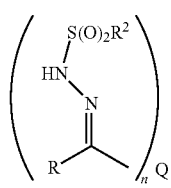

(XXVIb)

wherein n is an integer equal to or greater than 50, R is as defined hereinbefore, R² is as defined hereinbefore, and Q is polystyrene or a copolymer comprising styrene monomer units (a styrene copolymer). Each sulfonylhydrazone group in the compound of formula (XXVIb) is typically bonded to a phenyl group of said polystyrene or said copolymer comprising polystyrene.

Typically, the compound is of formula (XXVIc)

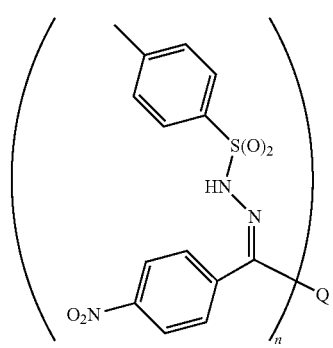

(XXVIc)

wherein n is an integer equal to or greater than 50 and Q is polystyrene or a copolymer comprising styrene monomer units (a styrene copolymer). Each sulfonylhydrazone group in the compound of formula (XXVIc) is typically bonded to a phenyl group of said polystyrene or said copolymer comprising polystyrene. The copolymer comprising styrene monomer units may for instance be poly(styrene)-poly(ethylene/butylene)-poly(styrene) (SEBS).

The multiple reactive intermediate precursor groups of the functionalised compounds of the invention can be readily converted into carbene reactive intermediate groups, which can in turn react with and bond to a wide variety of substrates, including individual molecules and bulk materials.

The carbene reactive intermediate groups are typically generated by a thermal process, but can be generated chemically or by irradiation. Typically, the carbene reactive intermediate groups are generated by heating. The functionalised compounds of the invention are usually heated to a temperature of from about 100° C. to about 180° C., more typically from about 110° C. to 160° C., in order to generate said carbene reactive intermediate groups. The heat might be applied to the functionalised compound externally, but may also be as a result of another process, for example, extrusion.

Accordingly, the functionalised compound of the invention, as defined herein, can be used as an agent to form 3-dimensional networks. Since the functionalised compounds of the invention bear at least 3 reactive intermediate precursor groups which can be converted into reactive intermediate groups, one molecule of the functionalised compound can react with three or more sites in three dimensions. Therefore, a molecule of the compound can form a network within a single compound, or between two or more different compounds, e.g. compounds A and B. The functionalised compound can also react with itself intermolecularly, i.e. with other molecules of the functionalised compound. Thus, a bulk sample of the functionalised compound can react both with itself and with any other material or materials with which it is brought into contact, to form a covalent network that bonds the materials together.

For instance, the chemical agent could be formulated with a coating comprising one or more materials and the reactive intermediate precursor groups of the functionalised compound may then be converted into reactive intermediate groups, thereby causing the functionalised compound to react with itself intermolecularly and to react with the components of the formulation. Such coatings can contain materials, monomers or polymers in any suitable physical form, for instance in the form of a solution (water on solvent based), a hot melt or a suspension of materials.

For instance, a bulk layer of a functionalised compound of the invention may be applied between two substrates, C and D, and the reactive intermediate precursor groups of the functionalised compound may then be converted into reactive intermediate groups, thereby causing the functionalised compound to react with itself intermolecularly and to react with the surfaces of the two substrates, thereby forming a network between E and F, bonding the two substrates together. Such substrates may be in any suitable physical form, for instance in the form of a solution or suspension of the substrate, or in the form of a solid film, layer, sheet or board. Alternatively, the substrates may be in powder form, or in the form of pellets, beads, particles, nanoparticles or microparticles. The pellets, beads or particles may be macroscopic particles, i.e. visible to the naked eye, or microscopic particles. Thus, the particles could be microparticles or nanoparticles.

Accordingly, the invention provides the use of a functionalised compound of the invention, as defined herein, as an agent for producing a chemically-bound three-dimensional network on or within a substrate.

Further provided is the use of a functionalised compound of the invention, as defined herein, as a cross linking agent.

Substrate particles, for instance, beads, microparticles, nanoparticles, encapsulates and fluorescent particles, can be cross linked onto, or incorporated on or within a three-dimensional network formed by, the functionalised compounds of the invention. The compounds of the invention can thereby act as carriers or delivery vehicles for the substrate particles, to facilitate delivery of the particles to a desired location. Such carrier compounds can be produced by converting the reactive intermediate precursor functionalities of a functionalised compound of the invention into carbene reactive intermediates in the presence of such substrate particles. The carbene reactive intermediate groups then react with the particles to couple the microparticles to the compound.

Accordingly, the invention provides a process for producing a treated particle, which process comprises:
(a) contacting a functionalised compound of the invention as defined herein with a substrate particle; and
(b) generating carbene reactive intermediate groups from said carbene precursor groups, so that a carbene reactive intermediate group reacts with the substrate particle to attach the particle to the compound, thereby yielding said treated particle.

The resulting treated particle may act as a carrier or a delivery vehicle. Accordingly, the invention provides a process for producing a particle-delivery compound, which process comprises:

(a) contacting a functionalised compound of the invention as defined herein with a substrate particle; and (b) generating carbene reactive intermediate groups from said carbene precursor groups, so that a carbene reactive intermediate group reacts with the substrate particle to attach the particle to the compound, thereby yielding said particle-delivery compound.

The functionalised compound may be any functionalised compound of the invention as defined herein.

Step (a) of the process typically comprises contacting the functionalised compound with a substrate particle, more typically mixing the substrate particle with the cross linking compound, optionally in the presence of a solvent. Any suitable solvent may be used. Typically, the solvent is water. Mixing can be facilitated by sonication. When the functionalised compound used is a diazo compound, step (b) usually comprises heating the reaction mixture. Typically, the reaction mixture is heated at the reflux temperature of the solvent employed. When the functionalised compound used is a hydrazone compound in which $R^1$ is H, this conversion may be achieved by oxidation of the hydrazone to a diazomethane followed by the application of energy, typically by heating or by irradiation. In some embodiments, the functionalised compounds of the invention are heated to a temperature of from about 100° C. to about 180° C., more typically from about 110° C. to 160° C., in order to generate said carbene reactive intermediate groups. When the functionalised compound used is a sulfonylhydrazone compound, step (b) usually comprises heating the reaction mixture in the presence of a base. Any suitable base may be used, for instance an organic base such as a trialkyl amine (e.g. triethylamine) or 1,8-diazabicyclo[5.4.0]undec-7-ene (DBU). Alternatively an inorganic base may be used, such as an alkali metal hydroxide, e.g. sodium, lithium or potassium hydroxide. Typically, the reaction mixture is heated at the reflux temperature of the solvent employed, and in some embodiments, it is heated to a temperature of from about 100° C. to about 180° C., more typically from about 110° C. to 160° C., in order to generate said carbene reactive intermediate groups.

The invention also provides a treated particle, which treated particle comprises a substrate particle attached to a cross linking moiety of formula (XXVIVa):

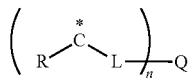

(XXVIVa)

wherein
C is a carbon atom;
* is a point of attachment of the carbon atom to the substrate particle or to another moiety or molecule; and
n, R, L and Q are as defined herein for the functionalised compound of the invention.

The treated particle may be a particle-delivery compound.

Typically, each * is a point of attachment of the cross linking moiety to a substrate particle or to another cross linking moiety of formula (XXVIVa).

In the treated particle or particle-delivery compound of the invention as defined above, n, R, L and Q may be as further defined hereinbefore.

In one embodiment, the particle-delivery compound comprises a plurality of substrate particles attached to a cross linking moiety of formula (XXVIVa).

Typically, the substrate particle used in the process of the invention for producing a treated particle or a particle-delivery compound, and the substrate particle of the treated particle of the invention or the particle-delivery compound of the invention, is a microparticle. The substrate particle may alternatively be a nanoparticle.

As used herein, the term "microparticle" means a microscopic particle whose size is measured in micrometers (μm). Typically, the microparticle has an average diameter of from 1 μm to 1000 μm. More typically, the microparticle has an average diameter of from 1 μm to 500 μm, for instance from 1 μm to 250 μm. Most typically, the microparticle has an average diameter of from 1 μm to 100 μm.

As used herein, the term "nanoparticle" means a microscopic particle whose size is measured in nanometers (nm). Typically, the nanoparticle has an average diameter of from 1 nm to 1000 nm. More typically, the nanoparticle has an average diameter of from 5 nm to 500 μm, for instance from 5 μm to 250 μm. Most typically, the nanoparticle has an average diameter of from 5 μm to 100 μm.

In one embodiment, the substrate particle is an encapsulate, i.e. a particle which encapsulates one or more functional molecules, for instance one or more perfume molecules. The encapsulate may itself be a microparticle or a nanoparticle. Alternatively, the encapsulate may be a macroscopic beads. Typically, however, the encapsulate is a microscopic particle, for instance a microparticle or a nanoparticle.

Typically, in this embodiment, the encapsulate is a perfume encapsulate, i.e. an encapsulate which comprises one or more perfume molecules. Such perfume encapsulates are known and commercially available. Any suitable perfume encapsulate may be used. Suitable encapsulates are described in WO/2002/074430 (Quest International B.V.), which relates to perfume encapsulates in which the capsule shell comprises a urea-formaldehyde or melamine-formaldehyde polymer and a second polymer comprising a polymer or copolymer of one or more anhydrides, preferably ethylene/maleic anhydride copolymer. Further suitable encapsulates are described in U.S. Pat. No. 7,125,835 (International Flavors & Fragrances Inc.); EP1533364 (International Flavours and Fragrances, Inc.); and U.S. Pat. No. 7,294,612 (International Flavours and Fragrances, Inc.). U.S. Pat. No. 7,294,612 describes a polymeric encapsulated fragrance which is suitable for use in personal care and cleaning products. In another embodiment, the encapsulate is, or comprises, a fluorescent particle.

In another embodiment, the substrate particle is a fluorescent particle.

Typically, Q is a polymer. Typically, n is an integer equal to or greater than 50, for instance equal to or greater than 100.

The polymer is typically one which provides the particle-delivery compound with an affinity for a particular target material, thus facilitating delivery of the particles to that target material.

In one embodiment, the target material is a fabric. The fabric may be cotton or polyester, for instance. The inventors have shown that the attachment of perfume encapsulates and fluorescent encapsulates to functionalised cross linking compounds of formula (II), in which Q comprises the polysaccharide locust bean gum, increases the deposition of the encapsulates onto cotton under wash cycle conditions.

Accordingly, in one embodiment Q comprises a polyester or a polysaccharide and the substrate particles are perfume encapsulates. The polyester may be Nylon, PET or POET, for instance. The polysaccharide may be a galactomannan, for instance locust bean gum.

The point of attachment of the cross linking moiety of formula (XXVIVa) to the substrate particle or to another cross linking moiety of formula (XXVIVa), is depicted "*". Thus, in the treated particles and in particle-delivery compounds of the invention as defined above, the carbon atom marked "*" is bonded to the substrate particle or to another cross linking moiety of formula (XXVIVa). As the skilled person would understand, various different modes of binding of the cross linking moiety of formula (XXVIVa) to the substrate particle or to another cross linking moiety of formula (XXVIVa) are possible via that carbon atom. For instance, the bond between the carbon atom marked "*" and an atom "Z" of the substrate particle (or an atom "Z" of another cross linking moiety of formula XXVIVa) may be a single covalent bond, in which case that carbon atom is also bonded to another atom or group (for example a hydrogen atom), as follows:

Alternatively, the bond between the carbon atom marked "*" and an atom "Z" of the substrate particle (or an atom "Z" of another cross linking moiety of formula XXVIVa) may be a double bond, as follows:

Alternatively, the bond between the carbon atom marked "*" and an atom "Z" of the substrate particle (or an atom "Z" of another cross linking moiety of formula XXVIVa) may be a dative bond (also known as a coordinate bond), in which both electrons are provided by the carbon atom, as follows:

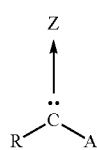

Alternatively, the carbon atom marked "*" may be bonded to two atoms, "Z" and "T", of the substrate particle (or to two atoms, "Z" and "T", of another cross linking moiety of formula (XXVIVa); or to one atom, "Z", of the substrate particle and to another atom, "T", of another cross linking moiety of formula (XXVIVa)) wherein the bonds between the carbon atom marked "*" and the atoms Z and Z' are both single bonds, as follows:

The diazo-functionalised compounds of the invention can be used to cross link two or more substrates, which two or more substrates may be the same or different.

Accordingly, the invention provides a process for cross linking a first substrate to a second substrate, which first and second substrates are the same or different, which process comprises (a) contacting the first and second substrates with a functionalised compound, wherein the functionalised compound is a functionalised compound of the invention as defined herein; and (b) generating carbene reactive intermediate groups from said carbene precursor groups, so that at least one carbene reactive intermediate group reacts with the first substrate and at least one other reactive intermediate group reacts with the second substrate, thereby cross linking the first and second substrates.

The functionalised cross linking compound may be any functionalised compound of the invention as defined herein.

In one embodiment, the reactive intermediate precursor groups are carbene precursor groups of formula (Ia), and the process for cross linking a first substrate to a second substrate comprises (a) contacting the first and second substrates with a diazo-functionalised cross linking compound, wherein the diazo-functionalised cross linking compound comprises n carbene precursor groups of formula (Ia), which are the same or different, wherein n is an integer equal to or greater than 2

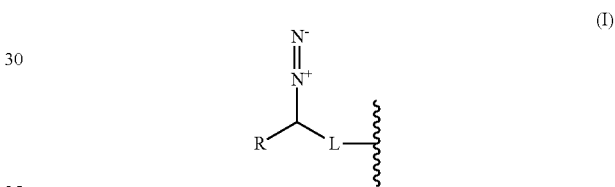

wherein L is a single bond or a linker group and R is a terminal group; and (b) generating carbene reactive intermediate groups from said carbene precursor groups, so that at least one carbene reactive intermediate group reacts with the first substrate and at least one other carbene reactive intermediate group reacts with the second substrate, thereby cross linking the first and second substrates.

In another embodiment, the reactive intermediate precursor groups are hydrazone precursor groups of formula (Ie). More typically, they are precursor groups of formula (Ie) in which $R^1$ is $—S(O)_2R^2$, wherein $R^2$ is as defined herein, i.e. sulfonylhydrazone groups.

As the skilled person will appreciate, typically some of the carbene reactive intermediate groups react with the first and second substrates and others react with other molecules of the cross linking compound itself.

In step (a), the first and second substrates may be contacted with the functionalised compound of the invention by any suitable method, depending on the physical forms of the first and second substrates. For instance, when the first and second substrates are both in particulate form, the particles may for instance be mixed with the functionalised compound of the invention to form a substantially homogeneous mixture. Alternatively, when the first and second substrates are both layers or sheets, the first and second substrates may be contacted with the functionalised compound of the invention by (i) applying a layer of the functionalised compound of the invention onto the first substrate, and (ii) subsequently applying a layer of the second substrate onto the functionalised compound of the invention. In another embodiment, the first and second substrates may be contacted with the functionalised compound of the invention by applying a mixture of the second substrate and the functionalised cross linking compound to the first substrate.

The functionalised compound of the invention may be applied as the neat compound or in solution. Any suitable solvent may be used for the functionalised compound of the invention. Such suitable solvents include but are not limited to alcohols, for instance methanol, methyl ethyl ketone and anisole.

The first or second substrate may for instance be contacted with the functionalised cross linking compound by dip coating, spray coating, rolling, printing or co-extrusion. The dip coating, spray coating, rolling, printing or co-extrusion may be performed in solution or otherwise. Thus, the dip coating, spray coating, rolling, printing or co-extrusion may be performed using a solution of the functionalised cross linking compound or using the neat functionalised cross linking compound. Similarly, the dip coating, spray coating, rolling, printing or co-extrusion may be carried out using the neat first or second substrate or using a suitable solution of the first or second substrate.

In step (b) of the process of the present invention for cross linking a first substrate to a second substrate, the generated carbene reactive intermediate groups may react with the surfaces of both the first and second substrates. In this context, the term "surface" means either the whole of the surface of the substrate in question or only a portion of the surface of the substrate.

The carbene reactive intermediate groups are typically generated by a thermal process, but may be generated chemically or by irradiation. Typically, the carbene reactive intermediate groups are generated by heating. This heat might be applied externally, but may also be as a result of another process, for example, extrusion. Thus, step (b) usually comprises heating the reaction mixture. Typically, the reaction mixture is heated at the reflux temperature of the solvent employed. In some embodiments, the mixture is heated to a temperature of from about 100° C. to about 180° C., more typically from about 110° C. to 160° C.

When the functionalised compound used is a sulfonylhydrazone compound, step (b) usually comprises heating the reaction mixture in the presence of a base. Any suitable base may be used, for instance an organic base such as a trialkyl amine (e.g. triethylamine) or 1,8-diazabicyclo[5.4.0]undec-7-ene (DBU). Alternatively an inorganic base may be used, such as an alkali metal hydroxide, e.g. sodium, lithium or potassium hydroxide. Typically, the reaction mixture is heated at the reflux temperature of the solvent employed or, for instance, to a temperature of from about 100° C. to about 180° C., more typically from about 110° C. to 160° C. When the functionalised compound used is a hydrazone compound in which $R^1$ is H, this conversion may be achieved by oxidation of the hydrazone to a diazomethane followed by the application of energy, typically by heating to said temperature.

Less typically, the reactive intermediate may be generated by electromagnetic radiation, for instance by UV, microwave or laser irradiation, or by ultrasonic irradiation. Some of these techniques, including laser and UV irradiation, are suitable for generation of the reactive intermediate selectively, i.e. on only a portion of the surface of the first or second substrate.

In one embodiment, only a portion of the surface of the first substrate is cross linked to a second substrate. For example, the surface of the first substrate may be modified in certain areas only, to form specific a "pattern" of cross linking. In this way, the two-dimensional shape of the resulting cross linked product may be controlled. This may be useful in the design of printed circuit boards, for example, where the cross linking of metal to substrate is only desired in certain specific places.

In one embodiment, the reactive intermediate groups are generated selectively, i.e. only on certain portions of the surface of the first substrate. In this way, only the particular regions of the surface on which the reactive intermediate has been generated become cross linked to the second substrate. This is known as "selective activation", and can be used to form specific a "pattern" of cross linking.

Q in the functionalised cross linking compound used in the process of the invention for cross linking a first substrate to a second substrate may be a core moiety as defined hereinbefore; typically, n is an integer of from 3 to 20, or from 4 to 20, or from 3 to 10, or 4 to 10, or an integer of 3, 4 or 5.

The invention also provides a cross-linked product comprising:
(a) a first substrate;
(b) a second substrate; and
(c) a cross linking moiety of formula (XXVIVa):

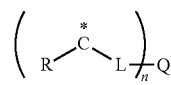

(XXVIVa)

wherein
C is a carbon atom;
\* is a point of attachment of the carbon atom to the first substrate, the second substrate, or to another moiety or molecule; and
n, R, L and Q are as defined herein for the functionalised compound of the invention.

Typically, each \* is a point of attachment of the cross linking moiety to the first substrate, the second substrate or to another cross linking moiety of formula (XXVIVa). However, as the skilled person will appreciate, some of the carbon or nitrogen atoms, E'\*, may be bonded to molecules of other compounds too, if such other compounds were present in the reaction mixture when the crosslinked product was formed.

As described above in relation to the treated particle and particle-delivery compound of the invention, various different modes of binding of the cross linking moiety of formula (XXVIV) to the first and second substrates or to another cross linking moiety of formula (XXVIV) are possible via the carbene or nitrogen atom E' marked "\*". Possible bonding modes include those described above.

In the cross-linked product of the invention as defined above, R, L and Q may be as further defined hereinbefore. Usually, Q is a core moiety as defined hereinbefore; typically, n is an integer of from 3 to 20, from 4 to 20, or from 3 to 10, or from 4 to 10, or an integer of 3, 4 or 5.

The first and second substrates which are crosslinked in accordance with the present invention may be the same material or two different materials. Each substrate may be any natural or synthetic substrate which is capable of reaction with a carbene reactive intermediate group generated from a diazo-functionalised cross linking compound as defined above, for instance from a diazo-functionalised compound of formula (II). Thus, a huge variety of first and second substrates may cross linked in accordance with the present invention.

The first and second substrates, which are the same or different, may for instance be independently selected from any of the following materials:

natural or synthetic polymers including but not limited to cellulose, polyglycosides, polypeptides, polyacrylates, polyacrylics, polyamides, polyimides, polycarbonates, polyesters, epoxy resins, polyethers, polyketones, polyolefins, rubbers, polystyrenics, polysulfones, polyurethanes, polyvinyls and their co-polymers;

polyesters, polyacrylates, polyolefins, polyamides, polyimides, polysulfones and epoxy resins, homopolymers and copolymers of ethylene, propylene, styrene, PET (polyethylene terephthalate) or EPDM (ethylene propylene diene monomer);

homopolymers and copolymers, for instance a block copolymers;

thermoplastic resins and thermosetting resins;

inorganic materials including but not limited to metals, metal alloys, metal salts, silica, glasses, alumina, titania, and allotropes of carbon such as diamond, diamond-like carbon, graphite, fullerenes and nanotubes;

nanoparticles and microparticles;

$C_{60}$ and nanotubes, for instance carbon nanotubes;

textiles and paper.

The first substrate, or the second substrate, may comprise any two or more of the above-listed materials.

The first and second substrates may be in any suitable physical form, and may be in the same form as one another or in different forms from one another. Suitable forms include film, layer, sheet or board, powder form, pellet form or in the form of beads, particles, nanoparticles or microparticles. The pellets, beads or particles may be macroscopic particles, i.e. visible to the naked eye, or microscopic particles. Thus, the particles could be microparticles or nanoparticles.

In one embodiment of the process of the invention for cross linking a first substrate to a second substrate, or of the cross-linked product of the invention, the first substrate is a first polymer and the second substrate is a second polymer. The first and second polymers, which may be the same or different, may be independently selected from any of those listed above.

In one embodiment the first polymer is a hydrophilic polymer, for instance poly(ethyleneimine). In another embodiment the first polymer is a hydrophobic polymer, for instance poly(tetrafluoroethylene). The second polymer may be a polyester or a poly(alkylene) (for instance polyethylene or polypropylene). In one embodiment, the second polymer is selected from poly(ethylene terephthalate) and polypropylene.

In another embodiment, the invention provides a process for producing a chemically-bound three-dimensional network on or within a substrate, which process comprises:

(a) contacting a substrate with a functionalised compound of the invention as defined herein; and (b) generating carbene reactive intermediate groups from said carbene precursor groups, so that said carbene reactive intermediate groups react with the substrate to produce said chemically-bound three-dimensional network on or within the substrate.

The substrate may for instance be independently selected from any of the following materials:

natural or synthetic polymers including but not limited to cellulose, polyglycosides, polypeptides, polyacrylates, polyacrylics, polyamides, polyimides, polycarbonates, polyesters, epoxy resins, polyethers, polyketones, polyolefins, rubbers, polystyrenics, polysulfones, polyurethanes, polyvinyls and their co-polymers;

polyesters, polyacrylates, polyolefins, polyamides, polyimides, polysulfones and epoxy resins, homopolymers and copolymers of ethylene, propylene, styrene, PET (polyethylene terephthalate) or EPDM (ethylene propylene diene monomer);

homopolymers and copolymers, for instance a block copolymers;

thermoplastic resins and thermosetting resins;

inorganic materials including but not limited to metals, metal alloys, metal salts, silica, glasses, alumina, titania, and allotropes of carbon such as diamond, diamond-like carbon, graphite, fullerenes and nanotubes;

nanoparticles and microparticles;

$C_{60}$ and nanotubes, for instance carbon nanotubes;

textiles and paper.

In step (a), the substrate may be contacted with the functionalised compound of the invention by any suitable method, depending on the physical form of the substrate. For instance, when the substrate is in particulate form, the substrate may be mixed with the functionalised compound of the invention to form a substantially homogeneous mixture. Alternatively, when the substrate is a layer or sheet, the substrate may be contacted with the functionalised compound of the invention by applying a layer of the functionalised compound of the invention onto the first substrate. In another embodiment, the substrate may be in the form of a melt, and the functionalised compound of the invention may be contacted with said melt.

The functionalised compound of the invention may be applied as the neat compound or in solution. Any suitable solvent may be used for the functionalised compound of the invention.

In step (b) of the process of the present invention for producing a chemically-bound three-dimensional network on or within a substrate, the generated carbene reactive intermediate groups react with the substrate to produce said chemically-bound three-dimensional network on or within the substrate. Thus, the generated carbene reactive intermediate groups may react with the bulk of the substrate, for instance in the case where the substrate is a melt or in solution, or just with the surface the substrate, for instance when the substrate is a solid material. In this context, the term "surface" means either the whole of the surface of the substrate in question or only a portion of the surface of the substrate. The carbene reactive intermediate groups are typically generated by a thermal process, but may be generated chemically or by irradiation. Typically, the carbene reactive intermediate groups are generated by heating. This heat might be applied externally, but may also be as a result of another process, for example, extrusion. Thus, step (b) usually comprises heating the reaction mixture. Typically, the reaction mixture is heated at the reflux temperature of the solvent employed. In some embodiments, the mixture is heated to a temperature of from about 100° C. to about 180° C., more typically from about 110° C. to 160° C. When the functionalised compound used is a sulfonylhydrazone compound, step (b) usually comprises heating the reaction mixture in the presence of a base. Any suitable base may be used, for instance an organic base such as a trialkyl amine (e.g. triethylamine) or 1,8-diazabicyclo[5.4.0]undec-7-ene (DBU). Alternatively an inorganic base may be used, such as an alkali metal hydroxide, e.g. sodium, lithium or potassium hydroxide. Typically, the reaction mixture is heated at the reflux temperature of the solvent employed or to a temperature of from about 100° C. to about 180° C., more typically from about 110° C. to 160° C. When the functionalised compound used is a hydrazone compound in which $R^1$ is H, the conversion may be achieved by oxidation of the hydrazone to a diazomethane followed by the application of energy, typically by heating or by irradiation.

In one embodiment of the process, the composition comprises:
(i) a substrate; and
(ii) a chemically-bound three-dimensional network on or within the substrate, which chemically-bound three-dimensional network is of formula (XXVIVa)

(XXVIVa)

wherein:
C is a carbon atom;
* is a point of attachment of the carbon atom to the substrate or to another molecule or moiety in the composition; and
n, R, L and Q are as defined in any one of claims 1 to 33, and the process comprises:
(a) contacting a substrate with a functionalised compound as defined herein; and
(b) generating carbene reactive intermediate groups from said carbene precursor groups, so that said carbene reactive intermediate groups react with the substrate to produce said composition.

The invention further provides a composition which comprises a chemically-bound three-dimensional network on or within a substrate, the composition comprising:
a substrate; and
a chemically-bound three-dimensional network on or within the substrate, which chemically-bound three-dimensional network is of formula (XXVIVa)

(XXVIVa)

wherein
C is a carbon atom;
* is a point of attachment of the carbon atom to the substrate or to another molecule or moiety in the composition; and
n, R, L and Q are as defined herein.

The substrate may for instance be as defined above for the process of the invention for producing a chemically-bound three-dimensional network on or within a substrate.

In another embodiment, the invention provides a process for producing a chemically-bound three-dimensional network between a first substrate and a second substrate, which process comprises:
(a) contacting a first substrate and a second substrate with a functionalised compound of the invention as defined herein; and
(b) generating carbene reactive intermediate groups from said carbene precursor groups, so that said carbene reactive intermediate groups react with the first substrate and the second substrate to produce said chemically-bound three-dimensional network between said first and second substrates.

The first and second substrates may be any suitable substrates and may be the same or different. They may for instance be independently selected from any of the materials listed above for the first and second substrates of the cross linked product of the invention.

In step (a), the first and second substrates may be contacted with the functionalised compound of the invention by any suitable method, depending on the physical forms of the first and second substrates. For instance, when the first and second substrates are both in particulate form, the particles may for instance be mixed with the functionalised compound of the invention to form a substantially homogeneous mixture. Alternatively, when the first and second substrates are both layers or sheets, the first and second substrates may be contacted with the functionalised compound of the invention by (i) applying a layer of the functionalised compound of the invention onto the first substrate, and (ii) subsequently applying a layer of the second substrate onto the functionalised compound of the invention. In another embodiment, the first and second substrates may be contacted with the functionalised compound of the invention by applying a mixture of the second substrate and the functionalised cross linking compound to the first substrate. The functionalised compound of the invention may be applied as the neat compound or in solution. Any suitable solvent may be used for the functionalised compound of the invention.

In one embodiment, the process for producing a chemically-bound three-dimensional network between a first substrate and a second substrate is a hot melt process, wherein step (a) comprises contacting a molten liquid comprising the first substrate and the second substrate with a functionalised compound of the invention as defined herein. Such hot melt processes are exemplified herein.

Step (b) can be performed as described above for the process of the invention for producing a chemically-bound three-dimensional network on or within a substrate.

In one embodiment of the process, the composition comprises:
a first substrate;
a second substrate; and
a three-dimensional network of formula (XXVIVa):

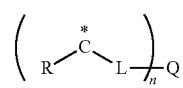
(XXVIVa)

wherein
C is a carbon atom;
* is a point of attachment of the carbon atom to the first or second substrate or to another molecule or moiety in said composition; and
n, R, L and Q are as defined herein for the functionalised compounds of the invention;
and the process comprises:
(a) contacting a first substrate and a second substrate with a functionalised compound as defined herein; and
(b) generating carbene reactive intermediate groups from said carbene precursor groups, so that said carbene reactive intermediate groups react with the first substrate and the second substrate to produce said composition.

The invention further provides a composition which comprises:
a first substrate;
a second substrate; and
a three-dimensional network of formula (XXVIVa), which is bound to said first and second substrates:

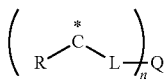

(XXVIVa)

wherein
C is a carbon atom;
* is a point of attachment of the carbon atom to the first or second substrate or to another molecule or moiety in said composition; and
n, R, L and Q are as defined herein for the functionalised compounds of the invention.

The invention further provides a process for producing a film or a coating, which process comprises:

(a) disposing a film formulation or a coating formulation onto the surface of a substrate, which film or coating formulation comprises a functionalised compound as defined herein; and (b) generating carbene reactive intermediate groups from said carbene precursor groups, thereby forming a film or a coating on said substrate.

In one embodiment, the process is for producing a film, and the process further comprises (c) removing said film from said substrate.

In another embodiment, the process is for producing a coated substrate which comprises:
a substrate; and
a coating on a surface of the substrate, which coating comprises a three-dimensional network of formula (XXVIVa):

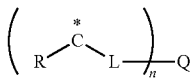

(XXVIVa)

wherein
C is a carbon atom;
* is a point of attachment of the carbon atom to the substrate or to another molecule or moiety in the coating; and
n, R, L and Q are as defined herein for the functionalised compounds of the invention;
which process comprises:

(a) disposing a coating formulation onto the surface of a substrate, which coating formulation comprises a functionalised compound of the invention as defined herein; and (b) generating carbene reactive intermediate groups from said carbene precursor groups, thereby forming a coating on said substrate.

Any suitable substrate can be used. The substrate may for instance be any of the materials listed above for the process of the invention for cross linking a first substrate to a second substrate.

The coating formulation used in step (a) typically comprises a further material, such as a second substrate, which may be the same as or different from the (first) substrate. Typically, the second substrate is a polymer, but it may for instance be any of the substrate materials listed above for the process of the invention for cross linking a first substrate to a second substrate.

Typically, the coating formulation is a solution which comprises said further material (second substrate) and said functionalised compound of the invention as defined herein, and a solvent.

In other embodiments, however, the coating formulation is a solution which comprises said functionalised compound of the invention and a solvent, and step (a) comprises a first step of disposing said coating formulation onto the surface of a substrate, and a second step of disposing a second solution onto the surface of a substrate, which second solution comprises said further material (second substrate) and a solvent. More typically, in this embodiment, step (a) comprises a first step of disposing said coating formulation onto the surface of a substrate, to form a layer of said coating formulation thereon, a second step of allowing the resulting layer to dry, and a third step of disposing a second solution onto the surface of a substrate, which second solution comprises said further material (second substrate) and a solvent.

Both of these alternatives are exemplified herein.

Step (b) can be carried out as described above for the processes of the invention for producing a chemically-bound three-dimensional network on or within a substrate, for producing a chemically-bound three-dimensional network between a first substrate and a second substrate, and for cross linking a first substrate to a second substrate.

The invention further provides a coated substrate which comprises:
a substrate; and
a coating on a surface of the substrate, which coating comprises a three-dimensional network of formula (XXVIVa):

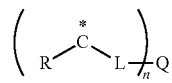

(XXVIVa)

wherein
C is a carbon atom;
* is a point of attachment of the carbon atom to the substrate or to another molecule or moiety in the coating; and
n, R, L and Q are as defined herein for the functionalised compounds of the invention.

The invention further provides a process for producing a product which comprises:
a first substrate;
a second substrate; and
a composition at an interface of the first and second substrates, which composition comprises (i) a third material and (ii) a three-dimensional network of formula (XXVIVa):

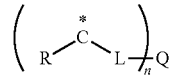

(XXVIVa)

wherein
C is a carbon atom;
* is a point of attachment of the carbon atom to the first substrate, the second substrate, the third material, or to another molecule or moiety in said composition; and
n, R, L and Q are as defined herein for the functionalised compounds of the invention;
which process comprises:

(a) providing a composition at an interface of a first substrate and a second substrate, which composition comprises (i) a third material and (ii) a functionalised compound as defined herein; and (b) generating carbene reactive intermediate groups from said carbene precursor groups, so that said carbene reactive intermediate groups react with the first substrate, the second substrate, and the third material, to produce said product.

Any suitable first and second substrates can be used. The first and second substrates may be the same or different and may for instance be any of the materials listed above for the process of the invention for cross linking a first substrate to a second substrate.

The third material is typically a polymer or resin. It may for instance be independently selected from any of the following materials:
- natural or synthetic polymers including but not limited to cellulose, polyglycosides, polypeptides, polyacrylates, polyacrylics, polyamides, polyimides, polycarbonates, polyesters, epoxy resins, polyethers, polyketones, polyolefins, rubbers, polystyrenics, polysulfones, polyurethanes, polyvinyls and their co-polymers;
- polyesters, polyacrylates, polyolefins, polyamides, polyimides, polysulfones and epoxy resins, homopolymers and copolymers of ethylene, propylene, styrene, PET (polyethylene terephthalate) or EPDM (ethylene propylene diene monomer);
- homopolymers and copolymers, for instance a block copolymers;
- thermoplastic resins and thermosetting resins.

The composition at the interface of the first and second substrate may be a solution which comprises (i) said third material and (ii) said functionalised compound as defined herein. Alternatively, however, the composition at the interface may be a dry film which comprises (i) said third material and (ii) said functionalised compound as defined herein.

Step (b) can be carried out as described above for the processes of the invention for producing a chemically-bound three-dimensional network on or within a substrate, for producing a chemically-bound three-dimensional network between a first substrate and a second substrate, and for cross linking a first substrate to a second substrate.

Further provided is a product which comprises:
- a first substrate;
- a second substrate; and
- a composition at an interface of the first and second substrates, which composition comprises (i) a third material and (ii) a three-dimensional network of formula (XXVIVa):

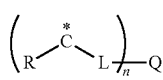

(XXVIVa)

wherein
C is a carbon atom;
* is a point of attachment of the carbon atom to the first substrate, the second substrate, the third material, or to another molecule or moiety in said composition at said interface of the first and second substrates; and
n, R, L and Q are as defined herein for the functionalised compounds of the invention.

Functionalised compounds of the invention of formula (II) may be produced by the process of the invention as defined hereinbefore for producing a functionalised compound of formula (II). Step (a) of the process comprises: (a) treating a first compound, Q', which is a core moiety, a polymer or a dendrimer and which bears n functional groups, with at least one second compound of formula (VIa)

wherein:

L' is a leaving group or a reactive precursor to said group of formula (XII), wherein L' is reactable with a said functional group to couple the second compound to the first compound, R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl, and Y is N=N, O or N—NHR$^1$, wherein R$^1$ is H or —S(O)$_2$R$^2$ and wherein R$^2$ is an unsubstituted or substituted $C_{1-6}$ alkyl group or an unsubstituted or substituted aryl group, provided that when none of the [R]$_x$E-L- groups in the functionalised compound of formula (II) to be produced is a group of formula (Ie) in which R$^1$ is —S(O)$_2$R$^2$, then each L' is a reactive precursor to said group of formula (XII) and Q' is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

Typically, the first compound Q' which bears n functional groups is treated with at least n equivalents of the at least one second compound of formula (VIa). As the skilled person will appreciate, however, functionalised compounds which comprise n carbene precursor groups of formula [R]$_x$-E-L-, all of which are the same, can be synthesised by treating said first compound Q' with at least n equivalents of a single second compound of formula (VIa). In contrast, functionalised compounds which comprise n carbene precursor groups of formula [R]$_x$-E-L- not all of which are the same can be synthesised by treating said first compound Q' with more than one type of second compound of formula (VIa). For instance, the first compound Q' which bears n functional groups can be treated with less than n equivalents of one compound of formula (VIa) and with less than n equivalents of another compound of formula (VIa), provided that the total number of equivalents of the compounds of formula (VIa) is at least n, to produce a functionalised compound of the invention comprising two different types of reactive intermediate precursor groups of formula [R]$_x$-E-L-.

The functionalised compound produced by the process of the invention is a compound of formula (II) which functionalised compound comprises n carbene precursor groups which are the same or different, wherein n is an integer equal to or greater than 3

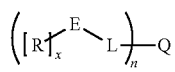
(II)

wherein x is 1, E is a group which is capable of being converted into a carbene reactive intermediate group, Q is a core moiety, a polymer or a dendrimer, and each of the [R]$_x$-E-L- groups, which are the same or different, is independently selected from a group of formula (Ie) and a group of formula (Ia):

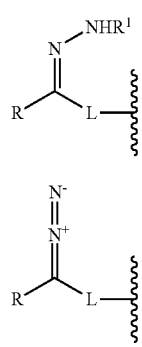

wherein

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

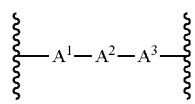
(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and $R^1$ is —S(O)$_2R^2$ or H, wherein $R^2$ is an unsubstituted or substituted $C_{1-6}$ alkyl group or an unsubstituted or substituted aryl group;

with the proviso that when none of the [R]$_x$-E-L- groups is a group of formula (Ie) in which $R^1$ is —S(O)$_2R^2$, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

and the process comprises:
(a) treating a first compound, Q', which is a core moiety, a polymer or a dendrimer and which bears n functional groups, with at least one second compound of formula (VIa)

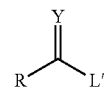
(VIa)

wherein:

L' is a leaving group or a reactive precursor to said group of formula (XII), wherein L' is reactable with a said functional group to couple the second compound to the first compound, R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ aryldi($C_{1-20}$ alkyl)silyl, diaryl($C_{1-20}$ alkyl)silyl and triarylsilyl, and Y is N=N, O or N—NHR$^1$, wherein R$^1$ is H or —S(O)$_2R^2$ and wherein $R^2$ is an unsubstituted or substituted $C_{1-6}$ alkyl group or an unsubstituted or substituted aryl group, provided that when none of the [R]$_x$-E-L- groups in the functionalised compound of formula (II) to be produced is a group of formula (Ie) in which $R^1$ is —S(O)$_2R^2$, then each L' is a reactive precursor to said group of formula (XII) and Q' is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

thereby producing a third compound of formula (IXa):

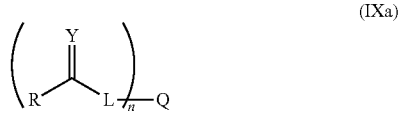

(IXa)

wherein Q, L, R, Y and n are as defined above;
provided that:
when Y is O, the process further comprises:
(b) treating the third compound with $H_2N-NHR^1$ in the presence of heat, wherein $R^1$ is as defined above, thereby producing a fourth compound of formula (X):

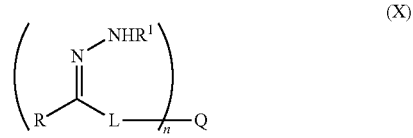

(X)

wherein Q, L, R, $R^1$ and n are as defined above; and, optionally,
(c) converting some or all of the $N-NHR^1$ groups of said fourth compound into diazo groups, $N{=}N$;
and provided that:
when Y is $N-NHR^1$, the process optionally further comprises:
(b) converting some or all of the Y groups of said third compound into diazo groups;
thereby producing said functionalised compound of formula (II).

The reaction conditions employed for step (a) depend on the particular standard coupling chemistry which is used to couple or react Q' with the leaving group or reactive precursor to L, denoted L', in the compound of formula (VIa). The coupling chemistry employed will of course depend on the particular terminal functional groups of Q' and L' that are reacted together (which include functional groups of formulae $-A^4-X^2$ and $-A^3-X$ respectively, as defined hereinbefore) but standard coupling chemistry can be used. For instance, the coupling of the Q' functional groups to the L' group in the compound of formula (VIa) can be achieved by reaction between a triazine moiety derived from cyanuric chloride and a hydroxyl group; such a reaction is used in the synthesis of the triazine-linked locust bean gum compound (6) in Example 1 hereinbelow. Alternatively, a reaction between an alkyl halide moiety and a hydroxyl group may be employed, as is used in the synthesis of the ether-linked diazomethane locust bean gum compound (9) in Example 1 hereinbelow. Alternatively, an esterification-type reaction may be employed, such as a standard esterification reaction between an —OH group and a carboxylic acid group, or a reaction between an —OH group and an activated carboxylic acid moiety such as an acyl halide or an acid anyhydride moiety. A coupling reaction between an acyl halide and a hydroxyl group is employed in the synthesis of the tris(4-methyl diaryldiazomethane) 1,3,5-benzene triester (19) in Example 1 hereinbelow. Alternatively, an aryl or heteroaryl group, such as a phenyl group, within Q' can readily be reacted with compounds of formula (VIa) in which L' is a leaving group, for instance a chloro group. In particular, acyl chloride compounds of formula (VIa) may react with aryl functional groups within a core moiety, polymer or dendrimer Q' by Fridel-Crafts Acylation. Such a reaction is well known in the art is described, for instance, in "Advanced Organic Chemistry; Reactions, Mechanisms, and Structure", Jerry March, Fourth Edition, 1992, Wiley Interscience. A synthesis Example (synthesis of benzophenone modified polymer 25) is outlined hereinbelow in Example 1. Typically, the Fridel-Crafts Acylation is carried out in solution in the presence of aluminium trichloride. Many other types of standard coupling reactions can however be employed in the present invention, such as for instance the coupling of an amino group or a thiol group to a carboxylic acid or acyl halide group, or the reaction of a functional group with an alkene or an alkyne group. Such standard coupling reactions are also well known in the art and are described, for instance, in "Advanced Organic Chemistry; Reactions, Mechanisms, and Structure", Jerry March, Fourth Edition, 1992, Wiley Interscience.

As explained hereinbefore, typically, Q' has a functionality $-A^4-X^2$ as defined herein, for instance an OH, NH, SH or aryl (typically phenyl) functionality that allows single step transformation to introduce the carbene precursor functionalities $[R]_x$-E-L- (or precursors thereof, $[R]_x$—C(O)-L-) onto Q.

Thus, in one embodiment, Q' is a core moiety, polymer or dendrimer which already possesses at least n $-A^4-X^2$ functionalities. The core moiety, polymer or dendrimer is therefore ready to react with the second compound of formula (VIa), in order to couple the second compound of formula (VIa) onto Q, in a single step.

Alternatively, however, a compound which does not bear any, or does not bear a sufficient number, n, of $-A^4-X^2$ functionalities can be synthetically modified to attach $-A^4-X^2$ functionalities, in order to synthesise a core moiety, polymer or dendrimer, Q', which has at least n $-A^4-X^2$ functionalities.

An example of this second strategy is the modification of a polymer, core moiety or dendrimer which bears OH groups (for instance a polysaccharide, such as locust bean gum, or a polyester polymer) by treating that polymer, core moiety or dendrimer with n equivalents of cyanuric chloride in order to generate a modified polymer, core moiety or dendrimer, Q', which bears n $-A^4-X^2$ functionalities of the following formula:

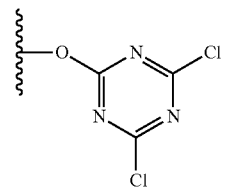 [SMILES: *Oc1nc(Cl)nc(Cl)n1]

Accordingly, the process of the invention for producing a functionalised compound may further comprise the step of:
preparing said first compound, Q', which bears n functional groups, by attaching said n functional groups to a precursor core moiety, a precursor polymer or a precursor dendrimer.

Typically, the functional groups are groups of formula $-A^4-X^2$ as defined herein.

Depending on the nature of Y in the compounds of formulae (VIa) and (IXa), the process of the invention for producing a functionalised compound may further comprise the steps of converting the ketone compound, when Y is O, into a hydrazone compound, and optionally converting a hydrazone compound, when Y is $N-NHR^1$ into the corresponding diazo compound.

Conversion of the ketone compound, when Y is O, into the corresponding hydrazone compound, where Y is N—NHR$^1$ is achieved by treating the ketone compound with H$_2$N—NHR$^1$ in the presence of heat, wherein R$^1$ is as defined above. Typically, the compound of formula (IXa) is treated with H$_2$N—NHR$^1$ in the presence of heat and a solvent. Any suitable solvent may be employed, for instance a polar protic solvent such as an alcohol. Typically, the solvent is methanol or ethanol. The reaction is carried out with heating, typically at the reflux temperature of the solvent used. For example, when the solvent is ethanol the reaction is suitably carried out at a temperature of 78° C. or higher, e.g. at a temperature of 80° C.

Conversion of the hydrazone compound, in which Y is N—NHR$^1$, into the corresponding diazomethane compound, in which Y is N=N, is achieved by oxidation or elimination. Accordingly, in one embodiment the N—NHR$^1$ groups of said third or fourth compound are converted into diazo groups, N=N, by oxidation or elimination. In the cases where R$^1$ is —S(O)$_2$R$^2$, wherein R$^2$ is as defined above, an elimination reaction is performed. The elimination is typically achieved by treating the hydrazone compound with a basic compound such as an inorganic salt or a trialkylamine compound or, for instance the organic base 1,8-diazabicyclo[5.4.0]undec-7-ene (DBU). Usually, the inorganic salt is lithium hydroxide, sodium hydroxide or potassium hydroxide. Usually, the trialkylamine compound is triethylamine. DBU can be advantageous in certain applications as it is non-volatile. Typically, the treatment of the tosyl hydrazone compound with the base (for instance a trialkylamine compound) is carried out in the presence of a solvent. The solvent used is suitably a polar protic solvent such as an alcohol, for instance methanol or water. The treatment can be carried out with the tosyl hydrazone compound either in phase with the base, as a biphasic mixture, or as a suspension of tosyl hydrazone compound in a basic solution.

In the case where R$^1$ is H, an oxidation reaction is performed. Any suitable oxidant can be used to convert the hydrazone compound, in which Y is N—NH$_2$, into the corresponding diazomethane compound. Suitable oxidants include metal oxides, such as mercuric oxide, nickel peroxide, or hydrogen peroxide or chlorine (bleach). Typically, the oxidant is manganese oxide. More typically, this oxidation is conducted in the presence of a base, for instance a metal hydroxide and sodium sulphate. The metal hydroxide is typically an alkali metal hydroxide, for instance potassium hydroxide. A saturated solution of the metal hydroxide is generally used. The solvent used for the metal hydroxide is suitably a polar protic solvent such as an alcohol, for instance ethanol. The solvent used for the solution of the compound of formula (III) is suitably a polar aprotic solvent, for instance tetrahydrofuran (THF) or an ether.

In one embodiment, the functionalised compound is a hydrazone compound of formula (XXX)

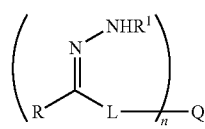

(XXX)

wherein:
n is an integer equal to or greater than 3;
R is aryl or heteroaryl, which aryl or heteroaryl is unsubstituted or substituted by one, two, three, four or five groups, which groups are the same or different and are independently selected from C$_{1-20}$ alkyl, C$_{2-20}$ alkenyl, C$_{2-20}$ alkynyl, C$_{1-20}$ haloalkyl, C$_{1-20}$ fluoroalkyl, C$_{1-20}$ perfluoroalkyl, aryl, cyano, nitro, hydroxy, halo, carboxy, amino, C$_{1-10}$ alkylamino, di(C$_{1-10}$)alkylamino, arylamino, diarylamino, arylalkylamino, amido, acyl, acyloxy, acylamido, ester, C$_{1-10}$ alkoxy, aryloxy, haloalkyl, thiol, C$_{1-10}$ alkylthio, arylthio, sulfonic acid, sulfonyl, sulfonamide, tri(C$_{1-20}$ alkyl)silyl, aryldi(C$_{1-20}$ alkyl)silyl, diaryl(C$_{1-20}$ alkyl)silyl and triarylsilyl;

each L, which is the same or different, is a single bond or a group of formula (XII)

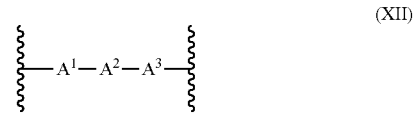

(XII)

wherein:
A$^1$ is bonded to the carbon atom bonded to R, wherein A$^1$ is an unsubstituted or substituted group selected from arylene and heteroarylene;

A$^2$ is a single bond or an unsubstituted or substituted group selected from C$_{1-20}$ alkylene, C$_{1-20}$ perfluoroalkylene, arylene, heteroarylene, *—C$_{1-20}$ alkylene-(O—C$_{1-20}$ alkylene-)$_m$ wherein m is 1 to 20, *—Z$^1$—C$_{1-20}$ alkylene, *—Z$^1$—C$_{1-20}$ perfluoroalkylene, *—Z$^1$-arylene, *—Z$^1$-heteroarylene and *—Z$^1$—C$_{1-20}$ alkylene-(O—C$_{1-20}$ alkylene-)$_m$ wherein m is 1 to 20, wherein Z$^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said C$_{1-20}$ alkylene and C$_{1-20}$ perfluoroalkylene groups is optionally interrupted by N(R"), O, S or arylene, and wherein each R" is independently selected from H, C$_{1-6}$ alkyl and aryl; and A$^3$ is a single bond or an unsubstituted or substituted group selected from *—Z$^2$-arylene, *—Z$^2$-heteroarylene, *—Z$^2$—C$_{1-20}$ alkylene, arylene, heteroarylene, C$_{1-20}$ alkylene, *—Z$^2$-arylene-O, *—Z$^2$-heteroarylene-O, *—Z$^2$—C$_{1-20}$ alkylene-O, *-arylene-O, *-heteroarylene-O, *—C$_{1-20}$ alkylene-O, C(O), S(O)$_2$, *—OC(O), *—N(R")C(O), O, S, N(R"), *—C(O)O, *—C(O)N(R"), *—S(O)$_2$O, C$_{1-20}$ alkenylene, C$_{1-20}$ alkynylene, *—Z$^2$—C$_{1-20}$ alkenylene and *—Z$^2$—C$_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$;

R$^1$ is H or —S(O)$_2$R$^2$, wherein R$^2$ is an unsubstituted or substituted C$_{1-6}$ alkyl group or an unsubstituted or substituted aryl group; and Q is a core moiety, a polymer or a dendrimer;
with the proviso that when R$^1$ is H, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

and the process comprises:
(a) treating a first compound, Q', which is a core moiety, a polymer or a dendrimer and which bears at least n functional groups, with at least one second compound of formula (VIa)

(VIa)

wherein:

L' is a leaving group or a reactive precursor to said group of formula (XII), wherein L' is reactable with a said functional group to couple the second compound to the first compound, R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ aryldi($C_{1-20}$ alkyl)silyl, diaryl($C_{1-20}$ alkyl)silyl and triarylsilyl, and Y is O or N—NHR$^1$, wherein R$^1$ is as defined above, provided that when R$^1$ is H, each L' is a reactive precursor to said group of formula (XII) and Q' is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

thereby producing a third compound of formula (IXa):

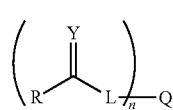

(IXa)

wherein Q, L, R, Y and n are as defined above, wherein when Y is N—NHR$^1$ said third compound is said hydrazone compound of formula (XXX);

provided that:

when Y is O, the process further comprises:

(b) treating the third compound with $H_2N$—NHR$^1$ in the presence of heat, wherein R$^1$ is as defined above, provided that when R$^1$ is H, each L' is a reactive precursor to said group of formula (XII) and Q' is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

thereby producing said hydrazone compound of formula (XXX).

Typically, R$^1$ is —S(O)$_2$R$^2$, wherein R$^2$ is as defined herein. In another embodiment, R$^1$ is H.

Typically, the functionalised compound is a sulfonylhydrazone compound of formula (XXXa)

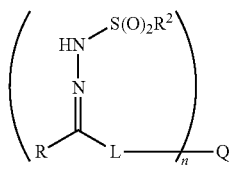

(XXXa)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)allylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ diaryl($C_{1-20}$ alkyl)silyl and triarylsilyl;

each L, which is the same or different, is a single bond or a group of formula (XII)

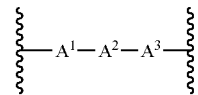

(XII)

wherein:

A$^1$ is bonded to the carbon atom bonded to R, wherein A$^1$ is an unsubstituted or substituted group selected from arylene and heteroarylene;

A$^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_R$, wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and A$^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of A$^3$ to A$^2$;

R$^2$ is an unsubstituted or substituted $C_{1-6}$ alkyl group or an unsubstituted or substituted aryl group; and Q is a core moiety, a polymer or a dendrimer;

and the process comprises:

(a) treating a first compound, Q', which is a core moiety, a polymer or a dendrimer and which bears at least n functional groups, with at least one second compound of formula (VIb)

(VIb)

wherein:

L' is a leaving group or a reactive precursor to said group of formula (XII), wherein L' is reactable with a said functional group to couple the second compound to the first compound, and R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-40}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

thereby producing a third compound of formula (IXb):

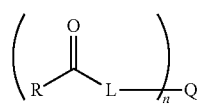
(IXb)

wherein Q, L, R and n are as defined above; and (b) treating the third compound with $H_2N$—$N(H)S(O)_2R^2$ in the presence of heat, wherein $R^2$ is an unsubstituted or substituted $C_{1-6}$ alkyl group or an unsubstituted or substituted aryl group, thereby producing said sulfonylhydrazone compound of formula (XXXa).

In another embodiment, the functionalised compound is a diazo-functionalised compound of formula (IIa)

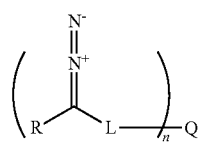
(IIa)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ diaryl($C_{1-20}$ alkyl)silyl and triarylsilyl;

each L, which may be the same or different, is a group of formula (XII)

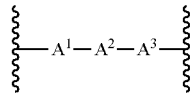
(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and Q is a core moiety, a dendrimer or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

and the process comprises:

(a) treating a first compound, Q', which bears n functional groups and which is a core moiety, a dendrimer or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof, with at least one second compound of formula (VIa)

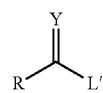
(VIa)

wherein:

L' is a reactive precursor to said group of formula (XII), wherein L' is reactable with a said functional group of the first compound, Q', to couple the second compound to the first compound, R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl, and Y is N=N, O or N—NHR$^1$, wherein R$^1$ is H or —S(O)$_2$R$^2$ and wherein R$^2$ is an unsubstituted or substituted $C_{1-6}$ alkyl group or an unsubstituted or substituted aryl group;

thereby producing a third compound of formula (IXa):

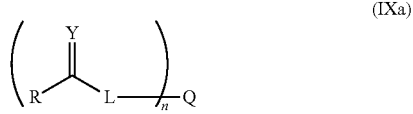

(IXa)

wherein Q, L, R, Y and n are as defined above, wherein when Y is N=N said third compound is said diazo-functionalised compound of formula (IIa);

provided that:

when Y is N—NHR$^1$, the process further comprises:
(b) converting the Y groups of said third compound into diazo groups, thereby producing said diazo-functionalised compound of formula (IIa);

and provided that:

when Y is O, the process further comprises:
(b) treating the third compound with H$_2$N—NHR$^1$ in the presence of heat, wherein R$^1$ is as defined above, thereby producing a fourth compound of formula (X):

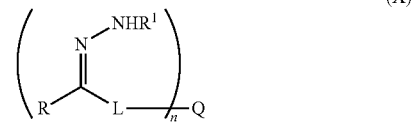

(X)

wherein Q, L, R, R$^1$ and n are as defined above; and
(c) converting the N—NHR$^1$ groups of said fourth compound into diazo groups, thereby producing said diazo-functionalised compound of formula (IIa).

The N—NHR$^1$ groups of said third or said fourth compound may be converted into diazo groups, N=N, by oxidation or elimination, as described hereinbefore.

Typically, in the processes of the invention for producing a functionalised compound, R$^2$ is an unsubstituted or substituted $C_{1-6}$ alkyl group, an unsubstituted or substituted phenyl group, or an unsubstituted or substituted naphthyl group. Typically, R$^2$ is $C_{1-6}$ alkyl, phenyl or naphthyl, which phenyl or naphthyl is unsubstituted or substituted with $C_{1-6}$ alkyl, di($C_{1-6}$ alkyl)amino, hydroxyl, nitro, cyano or methoxy. More typically, R$^2$ is $C_{1-6}$ alkyl, phenyl or naphthyl, which phenyl or naphthyl is unsubstituted or substituted with $C_{1-6}$ alkyl or di($C_{1-6}$ alkyl)amino.

In another embodiment, the functionalised compound is a hydrazone compound of formula (XXXb)

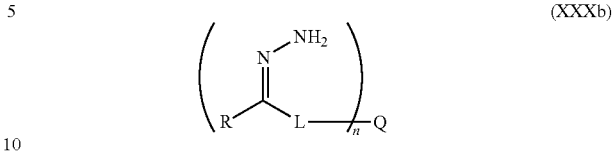

(XXXb)

wherein:

n is an integer equal to or greater than 3;

R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a group of formula (XII)

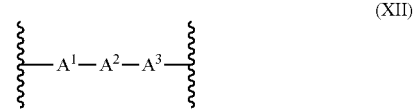

(XII)

wherein:

A$^1$ is bonded to the carbon atom bonded to R, wherein A$^1$ is an unsubstituted or substituted group selected from arylene and heteroarylene;

A$^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—Z$^1$—$C_{1-20}$ alkylene, *—Z$^1$—$C_{1-20}$ perfluoroalkylene, *—Z$^1$-arylene, *—Z$^1$-heteroarylene and *—Z$^1$—$C_{1-20}$ alkylene-(O—$C_{1-20}$ alkylene-)$_m$ wherein m is 1 to 20, wherein Z$^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and A$^3$ is a single bond or an unsubstituted or substituted group selected from *—Z$^2$-arylene, *—Z$^2$-heteroarylene, *—Z$^2$—$C_{1-20}$ alkylene, arylene, heteroarylene, $C_{1-20}$ alkylene, *—Z$^2$-arylene-O, *—Z$^2$-heteroarylene-O, *—Z$^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—Z$^2$—$C_{1-20}$ alkenylene and *—Z$^2$—$C_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of A$^3$ to A$^2$; and Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

and the process comprises:

(a) treating a first compound, Q', which bears n functional groups and which is a core moiety, a dendrimer or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof, with at least one second compound of formula (VIb)

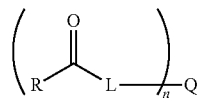

(VIb)

wherein:

L' is a reactive precursor to said group of formula (XII), wherein L' is reactable with a said functional group of the first compound, Q', to couple the second compound to the first compound, and R is aryl or heteroaryl, which aryl or heteroaryl is unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)allylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

thereby producing a third compound of formula (IXb):

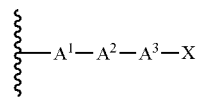

(IXb)

wherein Q, L, R and n are as defined above; and (b) treating the third compound with $H_2N$—$NH_2$ in the presence of heat, thereby producing said hydrazone compound of formula (XXXb).

Typically, in the process of the invention for producing a functionalised compound, L' is a group of formula (XI)

(XI)

and L is a group of formula (XII)

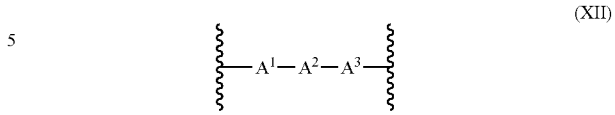

(XII)

wherein:

$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl;

$A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$;

and, in the group of formula (XI):

X is H, a halo group or a leaving group, provided that when $A^3$ is a single bond, *—$Z^2$-arylene, *—$Z^2$-heteroarylene, *—$Z^2$—$C_{1-20}$ alkylene, arylene, heteroarylene, $C_{1-20}$ alkylene or S(O)$_2$, X is other than H and provided that when $A^3$ is O, S, N(R"), —C(O)O—*, —C(O)N(R")—* or —S(O)$_2$O—*, X is other than a halo group.

In other embodiments, however, L is a single bond and L' is a leaving group.

Typically, the n functional groups of the first compound, Q', are groups of formula -$A^4$-$X^2$, wherein:

each $A^4$, which is the same or different, is independently selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —$Z^3$-arylene-O—*, —$Z^3$-heteroarylene-O—*, —$Z^3$—$C_{1-20}$ alkylene-O—*, arylene-O—*, heteroarylene-O—*, $C_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^4$ to $X^2$;

$X^2$ is H, a halo group or a leaving group;

provided that when $A^4$ is a single bond, arylene, heteroarylene, $C_{1-20}$ alkylene, —$Z^2$-arylene-*, —$Z^2$-heteroarylene-*, —$Z^2$—$C_{1-20}$ alkylene-* or S(O)$_2$, $X^2$ is other than H and provided that when $A^4$ is O, S, N(R"), —C(O)O—*, —C(O)N(R")—*, —S(O)$_2$O—*, —$Z^3$-arylene-O—*, —$Z^3$-heteroarylene-O—*, —$Z^3$—$C_{1-20}$ alkylene-O—*, arylene-O—*, heteroarylene-O—* or $C_{1-20}$ alkylene-O—*, $X^2$ is other than a halo group;

and wherein Q comprises n linker groups of formula $A^4$, each of which is attached to a group L, wherein each $A^4$ is independently selected from a single bond, —$Z^3$-arylene-*, —$Z^3$-heteroarylene-*, alkylene-*, arylene, heteroarylene, $C_{1-20}$ alkylene, —$Z^3$-arylene-O—*, —$Z^3$-heteroarylene-O—*, —$Z^3$—$C_{1-20}$ alkylene-O—*, arylene-O—*, heteroarylene-O—*, $C_{1-20}$ alkylene-O—*, —C(O)—*, $S(O)_2$, —OC(O)—*, —N(R")C(O)—*, O, S, N(R"), —C(O)O—*, —C(O)N(R")—*, —$S(O)_2O$—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R"), C(O), S(O), $S(O)_2$, C(O)O, OC(O), C(O)N(R") and N(R")C(O), wherein each R" is independently selected from H, $C_{1-6}$ alkyl and aryl, and wherein * is the point of attachment of $A^4$ to L.

In one embodiment, the n functional groups of said first compound, Q', are the same.

In one embodiment of the process of the invention for producing a functionalised compound, both Q and Q' comprise a polymer or dendrimer, wherein the polymer is a linear polymer, a branched polymer, a hyperbranched polymer, a homopolymer, a copolymer or a block copolymer. The polymer may comprise a polysaccharide or a polyester or polystyrene, for instance.

Typically, in the process of the invention for producing a functionalised compound, Q and Q' comprise a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

As mentioned above, in some embodiments, L is a single bond and L' is a leaving group. The leaving group L' may be a halo group, for instance chloro.

Typically, when L is a single bond and L' is a leaving group, said n functional groups of Q' are n aryl or heteroaryl rings, wherein Q comprises said n aryl or heteroaryl rings, and wherein each L is attached directly to a said aryl or heteroaryl ring of Q, thereby bonding the aryl or heteroaryl ring directly to the carbon atom which is bonded to R. Typically, in this embodiment the leaving group L' in the compound of formula (VIa) is a halo group, for instance chloro. More typically, L' is chloro and Y in the compound of formula (VIa) is O, and the coupling reaction in step (a) of the process of the invention between Q' and the compound of formula (VIa) is a Friedel-Crafts Acylation. Typically, the Friedel-Crafts Acylation is carried out in solution in the presence of aluminium trichloride. Typically, in this embodiment Q' and Q comprise a polymer that comprises said n aryl or heteroaryl rings. Usually said aryl or heteroaryl rings are aryl rings. The aryl rings are typically phenyl rings. Examples of polymers that comprise aryl rings include, for instance, polystyrene, a copolymer comprising polystyrene, a thermoplastic elastomer, polyisoprene, a copolymer comprising polyisoprene, SBS rubber, SIS rubber or poly(styrene)-poly(ethylene/butylene)-poly(styrene) (SEBS).

Accordingly, when L is a single bond and L' is a leaving group, Q' is typically a polymer and said n functional groups of Q' are n aryl or heteroaryl rings, wherein Q is a polymer which comprises said n aryl or heteroaryl rings and wherein each L which is single bond is attached directly to a said aryl or heteroaryl ring of Q, thereby bonding the aryl or heteroaryl ring directly to the carbon atom which is bonded to R. Typically, said aryl or heteroaryl rings are aryl rings. Typically, said aryl rings are phenyl rings.

In one embodiment of the process of the invention, L is a single bond, L' is a leaving group (for instance a halo group, e.g. chloro), Q' is a polymer and said n functional groups of Q' are n aryl or heteroaryl rings, and Q is a polymer which comprises said n aryl or heteroaryl rings, wherein each L which is single bond is attached directly to a said aryl or heteroaryl ring of Q, thereby bonding the aryl or heteroaryl ring directly to the carbon atom which is bonded to R. Typically, said aryl or heteroaryl rings are aryl rings. Typically, said aryl rings are phenyl rings. Typically, Q' and Q comprise polystyrene, a copolymer comprising polystyrene, a thermoplastic elastomer, polyisoprene, a copolymer comprising polyisoprene, SBS rubber, SIS rubber or poly(styrene)-poly(ethylene/butylene)-poly(styrene) (SEBS).

In one embodiment of the process of the invention Q' is a core moiety, a polymer or a dendrimer which bears n aryl or heteroaryl groups, and Q is a core moiety, polymer or dendrimer comprising n linker moieties which are arylene or heteroarylene groups, wherein each of said arylene or heteroarylene groups is attached to L.

Typically, Q' and Q comprise polystyrene, a copolymer comprising polystyrene, a thermoplastic elastomer, polyisoprene, a copolymer comprising polyisoprene, SBS rubber, SIS rubber or poly(styrene)-poly(ethylene/butylene)-poly(styrene) (SEBS).

In another embodiment, Q is a core moiety which is a straight-chained or branched, saturated or unsaturated $C_{1-20}$ hydrocarbon moiety; an aryl ring; a heteroaryl ring; a $C_{5-10}$ carbocyclic ring; a $C_{5-10}$ heterocyclic ring; or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n linker groups, $A^4$, and is otherwise unsubstituted or substituted, wherein each $A^4$ is attached to a group L, wherein $A^4$ is as defined above, and wherein Q' is a straight-chained or branched, saturated or unsaturated $C_{1-20}$ hydrocarbon moiety; an aryl ring; a heteroaryl ring; a $C_{5-10}$ carbocyclic ring; a $C_{5-10}$ heterocyclic ring; or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n functional groups, -$A^4$-$X^2$, and is otherwise unsubstituted or substituted, wherein $A^4$ and $X^2$ are as defined above.

Typically, Q' is a compound of formula (XIII) and Q is a core moiety of formula (XIV)

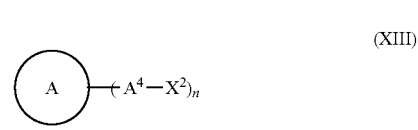

(XIII)

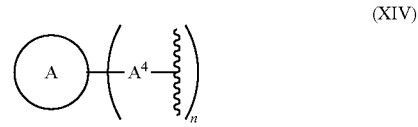

(XIV)

wherein n is an integer of from 3 to 10, each $A^4$ and each $X^2$ are the same or different and are as defined above and wherein A is an aryl ring, a heteroaryl ring, a $C_{5-10}$ carbocyclic ring, a $C_{5-10}$ heterocyclic ring, or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring;

or wherein Q' is a compound of formula (XV) and Q is a core moiety of formula (XVI)

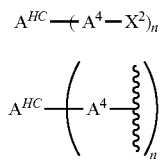

(XV)

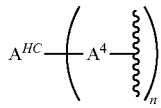

(XVI)

wherein n is an integer of from 3 to 10, each $A^4$ and each $X^2$ are the same or different and are as defined above and wherein $A^{HC}$ is straight-chained or branched, saturated or unsaturated $C_{1-20}$ hydrocarbon moiety which is otherwise unsubstituted or substituted.

Typically, in this embodiment, n is an integer of from 3 to 6.

Typically, in this embodiment, A is an aryl ring or a heteroaryl ring.

Typically, the $C_{1-20}$ hydrocarbon moiety is a straight-chained or branched $C_{1-10}$ hydrocarbon moiety which is substituted with said n $A^4$ linkers and is otherwise unsubstituted or substituted. For instance, it may be a methane, ethane, propane, butane, pentane, hexane, heptane, octane, nonane or decane moiety which is substituted with said n $A^4$ linkers and otherwise unsubstituted or substituted. The hydrocarbon may be straight-chained or branched. Thus, for instance, a propane hydrocarbon moiety may be i-propane or n-propane and a butane moiety may be t-butane, s-butane, i-butane or n-butane.

In one embodiment, n is 3.

Thus, more typically, Q' is a compound of formula (XIIIa) and Q is a core moiety of formula (XIVa)

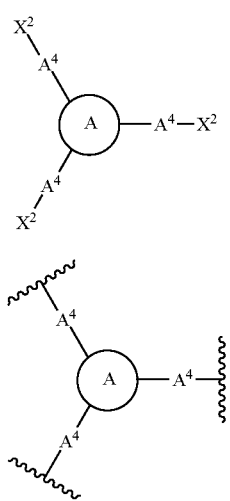

(XIIIa)

(XIVa)

wherein each $A^4$ and each $X^2$ are the same or different and are as defined above and wherein A is an aryl or heteroaryl ring;

or wherein Q' is a compound of formula (XVa) and Q is a core moiety of formula (XVIa)

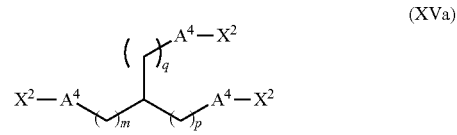

(XVa)

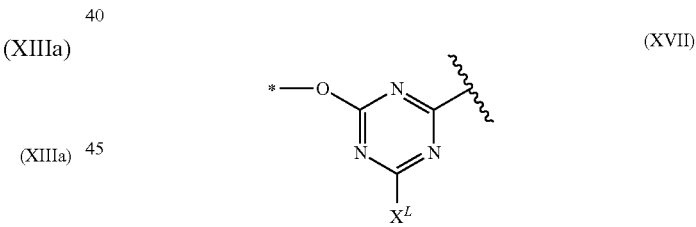

(XVIa)

wherein each $A^4$ and each $X^2$ are the same or different and are as defined above and wherein q, m and p are the same or different and are independently selected from 0 and an integer of 1 to 20.

In one embodiment of the process of the invention for producing a functionalised compound, $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, C(O), S(O)$_2$, *—OC(O) and *—N(R")C(O), wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$; and, in the group of formula (XI), X is halo or a leaving group.

Typically, in this embodiment, $A^3$ is a group of formula (XVII)

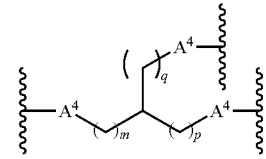

(XVII)

wherein * is the point of attachment of $A^3$ to $A^2$, and wherein $X^L$ is halo, hydroxyl, $C_{1-10}$ alkoxy, $C_{1-20}$ alkyl, $C_{2-20}$ alkenyl, $C_{2-20}$ alkynyl, aryl, aralkyl, cyano, amino, $C_{1-10}$ alkylamino, di($C_{1-10}$)alkylamino, arylamino, diarylamino, arylalkylamino, amido, acylamido, $C_{1-20}$ haloalkyl, ester, acyl, acyloxy, aryloxy, nitro, carboxy, sulfonic acid, sulfonyl, sulphonamide, thiol, $C_{1-10}$ alkylthio or arylthio; and, in the group of formula (XI), X is halo (more typically Cl). Typically, $X^L$ is halo or hydroxyl. More typically, $X^L$ is halo, for instance chloro.

Even more typically, in this embodiment, $A^1$ is phenylene; $A^2$ is *—$C_{1-20}$ alkylene-(O—$C_{1-20}$ alkylene-)$_m$ wherein m is 1 to 5 and wherein * is the point of attachment of $A^2$ to $A^1$; and $A^3$ is a group of formula (XVII)

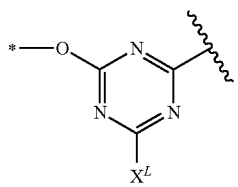
(XVII)

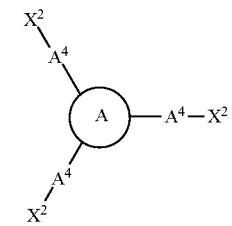
(XIII)

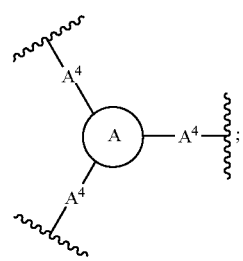
(XIV)

wherein * is the point of attachment of $A^3$ to $A^2$, $X^L$ is as defined above and, in the group of formula (XI), X is halo, for instance chloro. Thus, in a typical embodiment of the process of the invention for producing a functionalised compound, L' is:

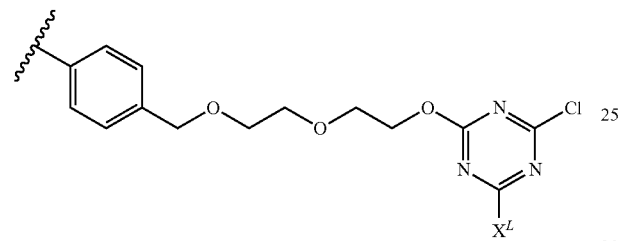

and L is:

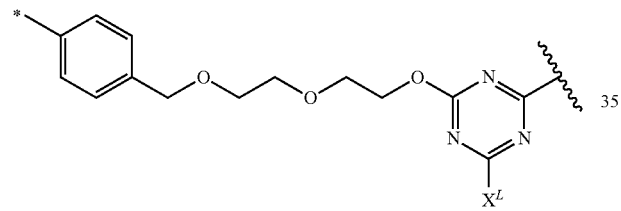

and L is:

wherein * is the point of attachment of L to the carbon atom bonded to R.

Alternatively, in this embodiment, $A^1$ is phenylene; $A^2$ is $C_{1-20}$ alkylene; $A^3$ is a single bond; and, in the group of formula (XI), X is a halo group. Thus, L' may be:

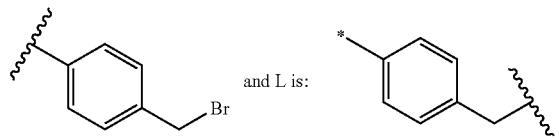

wherein * is the point of attachment of L to the carbon atom bonded to R.

Typically, in this embodiment, said first compound Q' is a core moiety, a polymer or a dendrimer which bears n —OH groups; and wherein Q is a core moiety, polymer or dendrimer comprising n linker atoms which are oxygen atoms, wherein each of said oxygen atoms is attached to a group L. More typically, first compound Q' is a polysaccharide. Alternatively, the first compound Q' may be a compound of formula (XIII) wherein Q is a core moiety of formula (XIV)

or the first compound Q' may be a compound of formula (XV) and Q is a core moiety of formula (XVI)

(XV)

(XVI)

wherein
A is an aryl or heteroaryl ring;
q, m and p are the same or different and are independently selected from 0 and an integer of 1 to 20;
each $A^4$ is the same or different and is independently selected from O, arylene-O—*, heteroarylene-O—*, $C_{1-20}$ alkylene-O—*, —$Z^3$-arylene-O—*, —$Z^3$-heteroarylene-O—*, —$Z^3$—$C_{1-20}$ alkylene-O—*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, wherein * is the point of attachment of $A^4$ to $X^2$ or L; and $X^2$ is H. Alternatively, L is itself a single bond and, in the group of formula (XI), X is a leaving group, which is typically halo. Thus, X may be chloro. Typically, in this embodiment, said first compound Q' is a core moiety, a polymer or a dendrimer which bears n aryl or heteroaryl groups, typically n phenyl groups; and wherein Q is a core moiety, polymer or dendrimer comprising n linker atoms which are arylene or heteroarylene groups, typically phenylene groups, wherein each of said arylene or heteroarylene groups is attached to L. More typically, the first compound Q' is polystyrene. Q' and Q may comprise polystyrene, a copolymer comprising polystyrene, a thermoplastic elastomer, polyisoprene, a copolymer comprising polyisoprene, SBS rubber, SIS rubber or poly(styrene)-poly (ethylene/butylene)-poly(styrene) (SEBS).

In a different embodiment of the process of the invention for producing a functionalised compound, $A^3$ is O, S, N(R"),

*—C(O)O, *—C(O)N(R"), *—S(O)$_2$O, C$_{1-20}$ alkenylene, C$_{1-20}$ alkynylene, *—Z$^2$—C$_{1-20}$ alkenylene or *—Z$^2$—C$_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$; and, in the group of formula (XI), X is H.

Typically, in this embodiment n A$^3$ is O and, in the group of formula (XI), X is H. More typically, A$^1$ is phenylene; A$^2$ is C$_{1-20}$ alkylene; A$^3$ is O; and, in the group of formula (XI), X is H. Thus, usually, L' is:

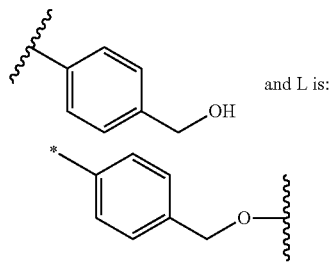

and L is:

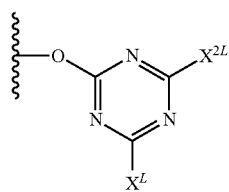

wherein * is the point of attachment of L to the carbon atom bonded to R.

Typically, in this embodiment of the process of the invention for producing a functionalised compound, said first compound Q' is a core moiety, a polymer or a dendrimer which bears n groups of formula (XVIII)

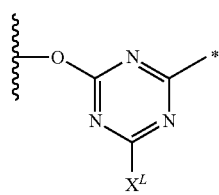
(XVIII)

wherein X$^L$ is as defined above, X$^{2L}$ is a halo group, typically chloro, and Q is a core moiety, polymer or dendrimer which bears n linker groups, each of which is attached to a group L, which linker groups are of formula (XIX)

(XIX)

wherein * is the point of attachment to L and wherein X$^L$ is as defined above. Typically, the process further comprises producing said first compound Q' by treating a core moiety, a polymer or a dendrimer, which core moiety, polymer or dendrimer bears at least n —OH groups, with cyanuric chloride. More typically, the process further comprises producing said first compound Q' by treating a polysaccharide or a polyester, which polysaccharide or polyester bears at least n —OH groups, with cyanuric chloride.

Alternatively, in this embodiment of the process of the invention for producing a functionalised compound, said first compound Q' is a compound of formula (XIII) and Q is a core moiety of formula (XIV)

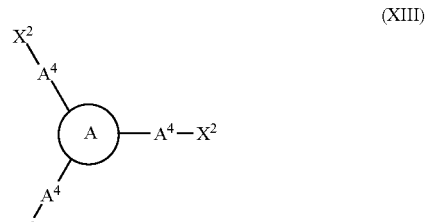
(XIII)

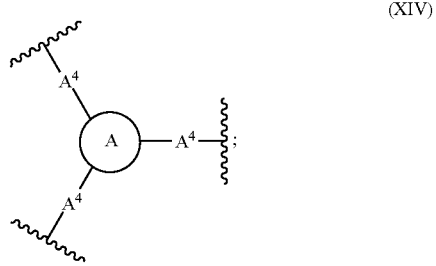
(XIV)

or Q' is a compound of formula (XV) and Q is a core moiety of formula (XVI)

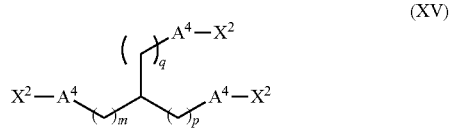
(XV)

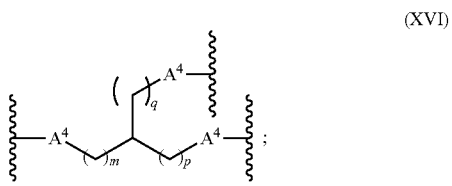
(XVI)

wherein

A is an aryl or heteroaryl ring;

q, m and p are the same or different and are independently selected from 0 and an integer of 1 to 20;

each A$^4$ is independently selected from a single bond, —Z$^3$-arylene-*, —Z$^3$-heteroarylene-*, —Z$^3$—C$_{1-20}$ alkylene-*, arylene, heteroarylene, C$_{1-20}$ alkylene, —C(O)—*, S(O)$_2$, —OC(O)—*, —N(R")C(O)—*, C$_{1-20}$ alkenylene, C$_{1-20}$ alkynylene, —Z$^3$—C$_{1-20}$ alkenylene-* and —Z$^3$—C$_{1-20}$ alkynylene-*, wherein Z$^3$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^4$ to X$^2$ or L; and X$^2$ is a halo group.

97

Thus, the first compound Q' may be:

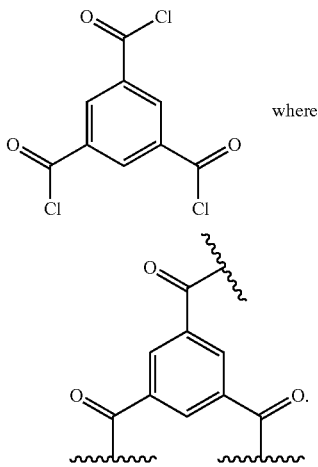

wherein Q is:

In one embodiment of the process for of the invention for producing a functionalised compound, at least one of the n functional groups of the first compound, Q', is protected and the remaining functional group or groups are unprotected, wherein L' of said second compound of formula (VIa) or (VIb) is reactable with said unprotected functional group or groups, to couple the second compound to the first compound, but not with said at least one protected functional group, wherein step (a) of the process comprises:

(i) treating said first compound, Q', with said second compound of formula (VIa) or (VIb), thereby coupling the second compound to the first via the unprotected functional group or groups;

(ii) deprotecting said at least one protected functional group; and (iii) treating the resulting compound with a compound of formula (VIa) as defined herein, or with a compound of formula (VIb) as defined herein, which is the same as or different from the second compound used in step (i), thereby producing said third compound.

Typically, in this embodiment, the unprotected functional groups are hydroxyl groups and the protected functional groups are protected hydroxyl groups. The protected hydroxyl groups may protected by $C_{1-20}$ alkyl groups (to form alkoxy groups) or by $C_{1-20}$ alkylene groups (to form —O—$C_{1-20}$ alkylene-O— groups). In the latter case, two protected hydroxyl groups are protected by one and the same $C_{1-20}$ alkylene group. The $C_{1-20}$ alkylene group may be an isopropylidene group, for example.

Thus, in one embodiment of the process of the invention for producing a functionalised compound, said first compound Q' is a compound of formula (XXXIII) and Q is a core moiety of formula (XXXIV)

(XXXIII)

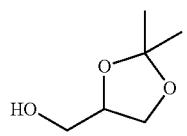

98

-continued (XXXIV)

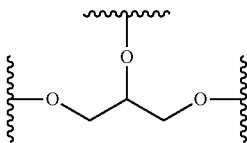

In this embodiment, the first compound Q' bears one unprotected hydroxyl functional group and two hydroxyl functional groups which are protected with an isopropylidene group. After the unprotected hydroxyl group is reacted with a second compound of formula (VIa) or (VIb), the two protected hydroxyl groups may be deprotected by hydrolysis. Typically, the hydrolysis is carried out in the presence of an acid. Typically, the hydrolysis is carried out in the presence of heat. The deprotected hydroxyl groups are then reacted with a compound of formula (VIa) or (VIb), to produce said third compound in the process of the invention.

FURTHER ASPECTS OF THE DISCLOSURE

In a broader aspect, disclosed herein is a functionalised compound, which functionalised compound comprises n reactive intermediate precursor groups of formula (I) which are the same or different, wherein n is an integer equal to or greater than 2

(I)

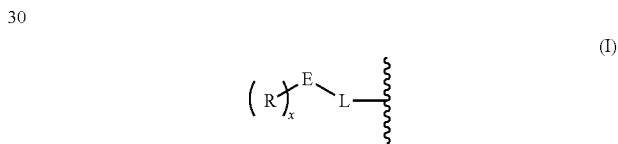

wherein x is 0 or 1, L is a single bond or a linker group, R is a terminal group and E is a reactive intermediate precursor functionality.

The term "reactive intermediate precursor functionality", as used herein, means a latent reactive group which is capable of being converted into a reactive intermediate group by a chemical process or by the application of energy, wherein the reactive intermediate group is capable of further reaction. The "application of energy" may for instance involve the application of thermal energy (i.e. heating) or irradiation, although any suitable source of energy can be used.

Examples of reactive intermediate precursor functionalities, E, include, but are not limited to the following groups:

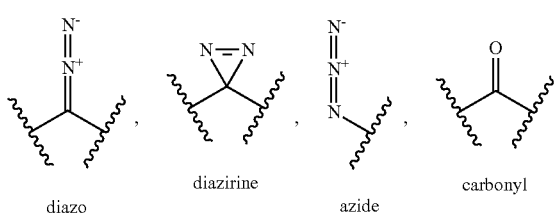

diazo, diazirine, azide, carbonyl

Thus, in one embodiment, E is a diazo, diazirine, azide or carbonyl group.

Diazo and diazirine groups are "carbene precursor groups", i.e. are capable of conversion into carbene reactive intermediates, whereas nitrene groups are "nitrene precursor groups", i.e. are capable of conversion into nitrene reactive intermediates. Carbonyl groups on the other hand are precursors which are capable of being converted into organic radical reactive intermediates, for instance into any of the following reactive intermediates:

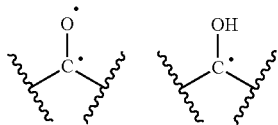

As the skilled person will appreciate, whether the integer x is 1 or 2 depends on the valency of the atom to which L and, when present, R, are attached. When that atom is a carbon atom (as it is in diazo, diazirine and carbonyl groups), x is 1, whereas when that atom is nitrogen (as it is in azide groups), x is 0.

Typically, the reactive intermediate employed is a carbene reactive intermediate, a nitrene reactive intermediate or an organic radical. Thus, typically, each of the reactive intermediate precursor functionalities, E, is selected from: a group which is capable of being converted into a carbene reactive intermediate group; a group which is capable of being converted into a nitrene reactive intermediate group; and a group which is capable of being converted into an organic radical.

Typically, the n reactive intermediate precursor groups of formula (I) are selected from:

carbene precursor groups, wherein x, L and R are as defined above and E is a group which is capable of being converted into a carbene reactive intermediate group;

nitrene precursor groups, wherein x, L and R are as defined above and E is a group which is capable of being converted into a nitrene reactive intermediate group; and organic radical precursor groups, wherein x, L and R are as defined above and E is a group which is capable of being converted into an organic radical.

In one embodiment, the n reactive intermediate precursor groups of formula (I), which are the same or different, are selected from groups of the following formula (Ia), (Ib), (Ic) and (Id):

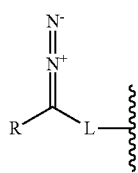 (Ia)

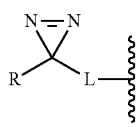 (Ib)

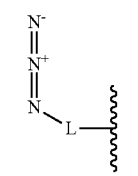 (Ic)

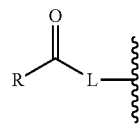 (Id)

wherein R and L are as defined above.

Typically, the n reactive intermediate precursor groups of formula (I) are diazo groups of formula (Ia), diazirine groups of formula (Ib) or azide groups of formula (Ic). More typically, the n reactive intermediate precursor groups of formula (I) are diazo groups of formula (Ia) or diazirine groups of formula (Ib). Even more typically, the n reactive intermediate precursor groups of formula (I) are diazo groups of formula (Ia).

The functionalised compound of the broader aspect as defined above comprises n reactive intermediate precursor groups of formula (I) which are the same or different. Thus, although each of the n reactive intermediate precursor groups falls within the formula (I) definition, the reactive intermediate precursor functionalities, E, the linker groups (or single bonds) L, the integer x and/or the terminal groups R when present, may differ from one reactive intermediate precursor group to the next in the functionalised compound. For instance, the functionalised compound may comprise a first reactive intermediate precursor group of formula (I) and a second reactive intermediate precursor group of formula (I), wherein the reactive intermediate precursor functionalities, E, the linker groups (or single bonds) L, the integer x and/or the terminal groups R are different in the first and second reactive intermediate precursor groups. Typically, however, E is the same reactive intermediate precursor functionality in all of the precursor groups in the functionalised compound. Similarly, L is typically the same in all of the precursor groups in the functionalised compound. Similarly, R is typically the same terminal group in all of the precursor groups in the compound, and/or x is the same integer in all of those groups.

The number of reactive intermediate precursor groups in the functionalised compound, n, is an integer equal to or greater than 2.

Typically, however, n is greater than or equal to 3. In another embodiment, n is greater than or equal to 4.

In one embodiment, n is an integer of from 2 to 50 or from 3 to 50, more typically an integer of from 2 to 20, from 2 to 10, from 3 to 20, or from 3 to 10, or an integer of 2, 3, 4 or 5.

In another embodiment, however, n is an integer of from 2 to 500, or from 3 to 500, and is more typically an integer of from 2 to 200, from 3 to 200, from 2 to 100, from 3 to 100, or from 10 to 100, for instance from 10 to 50.

In yet another embodiment, n is an integer equal to or greater than 50, for instance equal to or greater than 100. Thus, n may be an integer of from 50 to 1,000,000, from 50 to 100,000, from 50 to 10,000, from 50 to 5,000, or from 50 to 1,000. More typically, in this embodiment, n is an integer of from 50 to 1,000.

Typically, the functionalised compound of this broader aspect is a compound of formula (II)

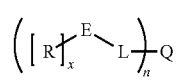 (II)

wherein n is an integer equal to or greater than 2 (but may be as further defined herein); x is 0 or 1; L is a single bond or a linker group; R is a terminal group; E is reactive intermediate precursor functionality; and Q is a core moiety, a polymer or a dendrimer.

Again, the reactive intermediate precursor functionalities, E, the linker groups (or single bonds) L, the terminal groups R, and the integer x may differ from one reactive intermediate precursor group to the next in the functionalised compound, but are typically the same.

Typically, each of the n reactive intermediate precursor functionalities, E, which are the same or different, is independently selected from: a group which is capable of being converted into a carbene reactive intermediate group; a group which is capable of being converted into a nitrene reactive intermediate group; and a group which is capable of being converted into an organic radical.

In one embodiment, each of the $[R]_x$-E-L- groups in the functionalised compound of this broader aspect of formula (II), which are the same or different, are independently selected from groups of the following formula (Ia), (Ib), (Ic) and (Id):

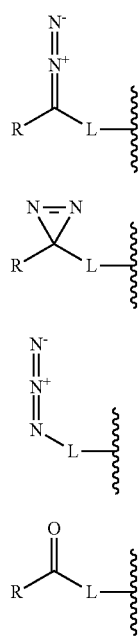

wherein R and L are as defined above.

Typically, the $[R]_x$-E-L- groups in the functionalised compound of this broader aspect of formula (II) are selected from diazo groups of formula (Ia), diazirine groups of formula (Ib) and azide groups of formula (Ic). More typically, the $[R]_x$-E-L- groups in the functionalised compound of this broader aspect of formula (II) are selected from diazo groups of formula (Ia) and diazirine groups of formula (Ib). Even more typically, the $[R]_x$-E-L- groups in the functionalised compound of this broader aspect of formula (II) are diazo groups of formula (Ia).

In one embodiment, the compound is a diazo-functionalised compound, which diazo-functionalised compound comprises n carbene precursor groups of formula (Ia) which are the same or different, wherein n is an integer equal to or greater than 2 (but may be as further defined herein):

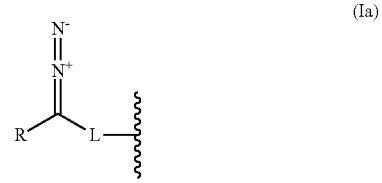

wherein L is a single bond or a linker group and R is a terminal group.

The diazo-functionalised compound of the invention as defined above comprises n carbene precursor groups of formula (I) which are the same or different. Thus, although each of the n carbene precursor groups falls within the formula (I) definition, the linker groups (or single bonds) L, and/or the terminal groups R, may differ from one carbene precursor group to the next in the diazo-functionalised compound. For instance, the diazo-functionalised compound may comprise a first carbene precursor group of formula (I) and a second carbene precursor group of formula (I), wherein the terminal groups R and/or the linker groups (or single bonds) L are different in the first and second carbene precursor groups. Typically, however, L is the same in all of the carbene precursor groups in the diazo-functionalised compound. Similarly, R is typically the same terminal group in all of the carbene precursor groups in the compound.

Typically, the diazo-functionalised compound of the invention is a compound of formula (IIa)

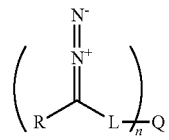

wherein n is an integer equal to or greater than 2 (but may be as further defined herein); L is a single bond or a linker group; R is a terminal group; and Q is a core moiety, a polymer or a dendrimer. Again, the linker groups (or single bonds) L, and the terminal groups R, may differ from one carbene precursor group to the next in the diazo-functionalised compound, but are typically the same.

Each R group is typically selected from hydrogen, aryl, heteroaryl, $C_{1-20}$ perfluoroalkyl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, $C_{1-20}$ haloalkyl, $C_{1-20}$ fluoroalkyl, $C_{1-20}$ perfluoroalkyl, aryl, heteroaryl, $C_{3-20}$ carbocyclyl, $C_{3-20}$ heterocyclyl, tri($C_{1-20}$ alkyl)silyl, aryldi($C_{1-20}$ diaryl($C_{1-20}$ alkyl)silyl, triarylsilyl, $C_{2-20}$ alkenyl, $C_{2-20}$ alkynyl and $C_{1-20}$ alkyl, which $C_{1-20}$ alkyl and $C_{1-20}$ perfluoroalkyl are optionally interrupted by N(R''), O, S or arylene wherein R'' is H, $C_{1-6}$ alkyl or aryl; provided that when R is aryl or heteroaryl said aryl or heteroaryl may be unsubstituted or substituted by one, two, three, four or five groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroallyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl.

Each R group may be as further defined herein.

As to the nature of the groups L in the functionalised compound, any suitable linking group may be employed or L may be a single bond.

Typically, however, each L, which may be the same or different, is a group of formula (XII)

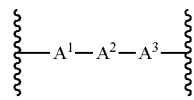

(XII)

wherein:

$A^1$ is bonded to the carbon atom bonded to R, wherein $A^1$ is a single bond or an unsubstituted or substituted group selected from arylene, heteroarylene, $C_{1-20}$ perfluoroalkylene, *—O—$C_{1-20}$ alkylene, *—O—$C_{1-20}$ perfluoroalkylene, *—O-arylene, *—O-heteroarylene, *—N(R")—$C_{1-20}$ alkylene, *—N(R")—$C_{1-20}$ perfluoroalkylene, *—N(R")-arylene, *—N(R")-heteroarylene, *—S—$C_{1-20}$ alkylene, *—S—$C_{1-20}$ perfluoroalkylene, *—S-arylene, *—S-heteroarylene, *—C(R')$_2$—$C_{1-20}$ alkylene, *—C(R')$_2$—$C_{1-20}$ perfluoroalkylene, *—C(R')$_2$-arylene, *—C(R')$_2$-heteroarylene and $C_{1-20}$ alkylene, wherein each R' is independently selected from a halogen atom, $C_{1-10}$ haloalkyl, $C_{1-10}$ fluoroalkyl, $C_{1-10}$ perfluoroalkyl, aryl, heteroaryl, $C_{3-10}$ carbocyclyl, $C_{3-10}$ heterocyclyl, tri($C_{1-10}$ aryldi($C_{1-10}$ alkyl)silyl, diaryl($C_{1-10}$ alkyl)silyl, triarylsilyl, $C_{2-10}$ alkenyl, $C_{2-10}$ alkynyl and $C_{1-10}$ alkyl, wherein * is the point of attachment of $A^1$ to the carbon atom bonded to R, wherein each of said $C_{1-20}$ alkylene and $C_{1-20}$ perfluoroalkylene groups is optionally interrupted by N(R"), O, S or arylene, and wherein R" is H, $C_{1-6}$ alkyl or aryl;

and $A^2$ and $A^3$ are as defined hereinbefore.

$A^1$, $A^2$ and $A^3$ may be as further defined hereinbefore.

In one embodiment $A^1$, $A^2$ and $A^3$ are all single bonds, which means that L is itself a single bond. Thus, in some embodiments, L is a single bond and each of the reactive intermediate precursor functionalities, E, is bonded directly to Q.

In one embodiment of the broader aspect, the functionalised compound is of formula (XXIIIa)

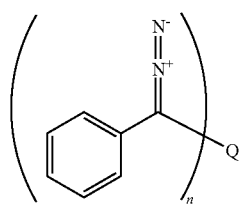

(XXIIIa)

wherein Q and n are as defined hereinbefore. Typically in this embodiment, Q is a core moiety, polymer or dendrimer bearing aryl or heteroaryl groups, more typically phenyl groups, wherein the carbon atom of the diazomethane group is bonded directly to said aryl or heteroaryl groups. More typically, in this embodiment, Q is polystyrene. Typically, the carbon atoms of the diazomethane groups are bonded to phenyl groups of said polystyrene. In one embodiment of the broader aspect, the functionalised compound is of formula (XXVIa)

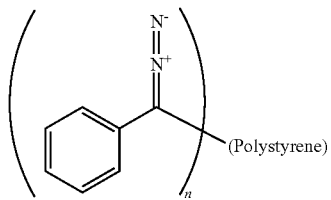

(XXVIa)

wherein n is an integer equal to or greater than 50.

The functionalised compounds of the broader aspects as defined above may be as further defined herein for the functionalised compounds of the invention.

Since the functionalised compounds of the broad aspect disclosed herein bear at least 2 reactive intermediate precursor groups which can be converted into reactive intermediate groups, one molecule of the functionalised compound can react with two or more molecules or particles of a substrate compound, B, to form a cross link between the molecules or particles of B. Similarly, a molecule of the compound can form a cross link between two or more different compounds, e.g. compounds C and D. The functionalised compound can also react with itself intermolecularly, i.e. with other molecules of the functionalised compound. Thus, a bulk sample of the functionalised compound can react both with itself and with any other material or materials with which it is brought into contact, to form a cross-linked network that bonds the materials together. For instance, a bulk layer of a functionalised compound may be applied between two substrates, E and F, and the reactive intermediate precursor groups of the functionalised compound may then be converted into reactive intermediate groups, thereby causing the functionalised compound to react with itself intermolecularly and to react with the surfaces of the two substrates, thereby forming a cross-linked network between E and F, bonding the two substrates together.

Such substrates may be in any suitable physical form, for instance in the form of a solution or suspension of the substrate, or in the form of a solid film, layer, sheet or board. Alternatively, the substrates may be in powder form, or in the form of pellets, beads, particles, nanoparticles or microparticles. The pellets, beads or particles may be macroscopic particles, i.e. visible to the naked eye, or microscopic particles. Thus, the particles could be microparticles or nanoparticles.

Accordingly, provided herein is the use of a functionalised compound as defined herein, as a cross linking agent.

In another broad aspect, disclosed herein is a process for producing a particle-delivery compound, which process comprises:

(a) contacting a functionalised cross linking compound with a substrate particle, wherein the functionalised cross linking compound comprises n reactive intermediate precursor groups of formula (I) which are the same or different, wherein n is an integer equal to or greater than 2

(I)

wherein x is 0 or 1, L is a single bond or a linker group, R is a terminal group and E is a reactive intermediate precursor functionality; and (b) generating reactive intermediate groups from said reactive intermediate precursor groups, so that a reactive intermediate group reacts with the substrate particle to attach the particle to the compound, thereby yielding said particle-delivery compound.

In another broad aspect, disclosed herein is a particle-delivery compound, which particle-delivery compound comprises a substrate particle attached to a cross linking moiety of formula (XXVIV)

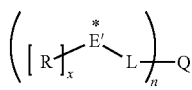
(XXVIV)

wherein
E' is a carbon or nitrogen atom;
* is a point of attachment of the cross linking moiety to the substrate particle or to another moiety or molecule;
n is an integer equal to or greater than 2;
x is 1 when E' is carbon and x is 0 when E' is nitrogen;
each L, which is the same or different, is a single bond or a linker group;
each R, which is the same or different, is a terminal group; and
Q is a core moiety, a polymer or a dendrimer.

In another broad aspect, disclosed herein is a process for cross linking a first substrate to a second substrate, which first and second substrates are the same or different, which process comprises (a) contacting the first and second substrates with a functionalised cross linking compound, wherein the functionalised cross linking compound comprises n reactive intermediate precursor groups of formula (I) which are the same or different, wherein n is an integer equal to or greater than 2

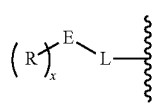
(I)

wherein x is 0 or 1, L is a single bond or a linker group, R is a terminal group and E is a reactive intermediate precursor functionality; and (b) generating reactive intermediate groups from said reactive intermediate precursor groups, so that at least one reactive intermediate group reacts with the first substrate and at least one other reactive intermediate group reacts with the second substrate, thereby cross linking the first and second substrates.

In another broad aspect, disclosed herein is a cross-linked product comprising:

(a) a first substrate;
(b) a second substrate; and
(c) a cross linking moiety of formula (XXVIV)

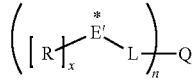
(XXVIV)

wherein
the first and second substrates are the same or different,
E' is a carbon or nitrogen atom;
each * is a point of attachment of the cross linking moiety to the first substrate, the second substrate or to another moiety or molecule;
n is an integer equal to or greater than 2;
x is 1 when E' is carbon and x is 0 when E' is nitrogen;
each L, which is the same or different, is a single bond or a linker group;
each R, which is the same or different, is a terminal group; and
Q is a core moiety, a polymer or a dendrimer.

In another broad aspect, disclosed herein is a process for producing a functionalised compound, which functionalised compound comprises n reactive intermediate precursor groups of formula (I) which are the same or different, wherein n is an integer equal to or greater than 2

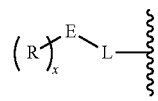
(I)

wherein x is 0 or 1, L is a single bond or a linker group, R is a terminal group and E is a reactive intermediate precursor functionality,
the process comprising:
(a) treating a first compound which bears n functional groups, with at least one second compound of formula (VI)

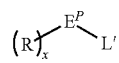
(VI)

wherein:
L' is a leaving group or a reactive precursor to said linker group, wherein L' is reactable with a said functional group to couple the second compound to the first compound,
R is said terminal group and x is 0 or 1, and
$E^P$ is said reactive intermediate precursor functionality E or a precursor thereto,
thereby producing a third compound which comprises n groups of formula (VII):

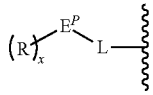
(VII)

wherein L is said single bond or linker group, R is said terminal group, x is 0 or 1, and $E^P$ is as defined above, which third compound is said functionalised compound when $E^P$ is said reactive intermediate precursor functionality E;

provided that:

when $E^P$ is a precursor to said reactive intermediate precursor functionality E, the process further comprises:

(b) converting the groups of formula (VII) of said third compound into reactive intermediate precursor groups of formula (I), thereby producing said functionalised compound.

Typically, the first compound which bears n functional groups is treated with at least n equivalents of the at least one second compound of formula (VI). As the skilled person will appreciate, however, functionalised compounds which comprise n reactive intermediate precursor groups of formula (I) all of which are the same can be synthesised by treating said first compound with at least n equivalents of a single second compound of formula (VI). In contrast, functionalised compounds which comprise n reactive intermediate precursor groups of formula (I) not all of which are the same can be synthesised by treating said first compound with more than one type of second compound of formula (VI). For instance, the first compound which bears n functional groups can be treated with less than n equivalents of one compound of formula (VI) and with less than n equivalents of another compound of formula (VI), provided that the total number of equivalents of the compounds of formula (VI) is at least n, to produce a functionalised compound comprising two different types of reactive intermediate precursor groups of formula (I).

Typically, the functionalised compound produced is a compound of formula (II)

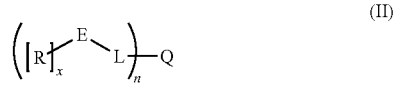
(II)

wherein n is an integer equal to or greater than 2; x is 0 or 1; L is a single bond or a linker group; R is a terminal group; E is reactive intermediate precursor functionality; and Q is a core moiety, a polymer or a dendrimer, and the process comprises:
(a) treating a first compound, Q', which is a core moiety, a polymer or a dendrimer and which bears n functional groups, with at least one second compound of formula (VI)

(VI)

wherein:

L' is a leaving group or a reactive precursor to said linker group, wherein L' is reactable with a said functional group to couple the second compound to the first compound, R is said terminal group and x is 0 or 1, and $E^P$ is said reactive intermediate precursor functionality E or a precursor thereto, thereby producing a third compound which is of formula (IX):

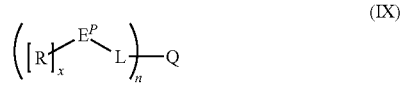
(IX)

wherein L is said single bond or linker group, R is said terminal group, x is 0 or 1, and $E^P$ is as defined above, which third compound is said functionalised compound of formula (II) when $E^P$ is said reactive intermediate precursor functionality E;

provided that:

when $E^P$ is a precursor to said reactive intermediate precursor functionality E, the process further comprises:

(b) converting the $E^P$ groups of said third compound into reactive intermediate precursor groups, E, thereby producing said functionalised compound of formula (II).

Typically, each of the n reactive intermediate precursor functionalities, E, which are the same or, different, is independently selected from: a group which is capable of being converted into a carbene reactive intermediate group; a group which is capable of being converted into a nitrene reactive intermediate group; and a group which is capable of being converted into an organic radical.

In one embodiment, each of the $[R]_x$-E-L- groups in the functionalised compound of formula (II), which are the same or different, are independently selected from groups of the following formula (Ia), (Ib), (Ic) and (Id):

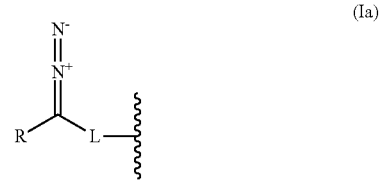
(Ia)

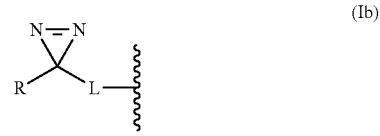
(Ib)

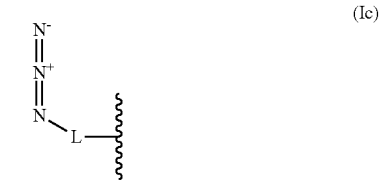
(Ic)

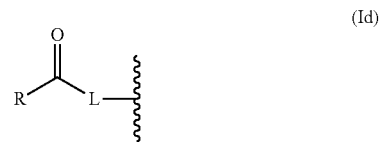
(Id)

wherein R and L are as defined above.

Typically, the $[R]_x$-E-L- groups in the functionalised compound of formula (II) are selected from diazo groups of formula (Ia), diazirine groups of formula (Ib) and azide groups of formula (Ic). More typically, the $[R]_x$-E-L- groups in the functionalised compound of formula (II) are selected from diazo groups of formula (Ia) and diazirine groups of formula (Ib).

Even more typically, the $[R]_x$-E-L- groups in the functionalised compound of formula (II) are diazo groups of formula (Ia).

Accordingly, disclosed herein is a process for producing a diazo-functionalised compound, which diazo-functionalised compound comprises n carbene precursor groups of formula (Ia), which are the same or different, wherein n is an integer equal to or greater than 2

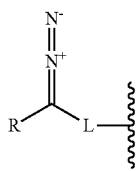

(Ia)

wherein L is a single bond or a linker group and R is a terminal group, the process comprising:

(a) treating a first compound which bears n functional groups, with at least one second compound of formula (VIa)

(VIa)

wherein:

L' is a leaving group or a reactive precursor to said linker group, wherein L' is reactable with a said functional group to couple the second compound to the first compound, R is said terminal group, and Y is N=N, O or N—NHR$^1$, wherein R$^1$ is H or —S(O)$_2$R$^2$ and wherein R$^2$ is C$_{1-6}$ alkyl, phenyl or naphthyl, which phenyl or naphthyl is unsubstituted or substituted with C$_{1-6}$ alkyl or di(C$_{1-6}$ alkyl)amino, thereby producing a third compound which comprises n groups of formula (VIIa):

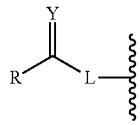

(VIIa)

wherein L is said single bond or linker group, R is said terminal group and Y is as defined above, which third compound is said diazo-functionalised compound when Y is N=N;

provided that:

when Y is N—NHR$^1$, the process further comprises:

(b) converting the groups of formula (VIIa) of said third compound, by oxidation or elimination, into carbene precursor groups of formula (Ia), thereby producing said diazo-functionalised compound; and provided that:

when Y is O, the process further comprises:

(b) treating the third compound with H$_2$N—NHR$^1$ in the presence of heat, wherein R$^1$ is as defined above, thereby producing a fourth compound which comprises n groups of formula (VIII):

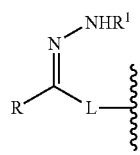

(VIII)

wherein L is said single bond or linker group, R is said terminal group and R$^1$ is as defined above; and (c) converting the groups of formula (VIII) of said fourth compound, by oxidation or elimination, into carbene precursor groups of formula (Ia), thereby producing said diazo-functionalised compound.

Typically, the diazo-functionalised compound produced by the process is a compound of formula (IIa)

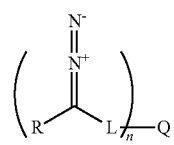

(IIa)

wherein:

n is an integer equal to or greater than 2;

each L is a single bond or a linker group;

each R is a terminal group; and

Q is a core moiety, a polymer or a dendrimer;

and the process comprises:

(a) treating a first compound, Q', which is a core moiety, a polymer or a dendrimer and which bears n functional groups, with at least one second compound of formula (VIa)

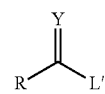

(VIa)

wherein:

L' is a leaving group or a reactive precursor to said linker group, wherein L' is reactable with a said functional group to couple the second compound to the first compound, R is said terminal group, and Y is N=N, O or N—NHR$^1$, wherein R$^1$ is H or —S(O)$_2$R$^2$ and wherein R$^2$ is C$_{1-6}$ alkyl, phenyl or naphthyl, which phenyl or naphthyl is unsubstituted or substituted with C$_{1-6}$ alkyl or di(C$_{1-6}$ alkylamino, thereby producing a third compound of formula (IXa):

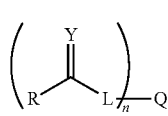

(IXa)

wherein Q, L, R, Y and n are as defined above, which third compound is said diazo-functionalised compound when Y is N=N;

provided that:

when Y is N—NHR$^1$, the process further comprises:

(b) converting the Y groups of said third compound, by oxidation or elimination, into diazo groups, thereby producing said diazo-functionalised compound of formula (IIa); and provided that:

when Y is O, the process further comprises:

(b) treating the third compound with H$_2$N—NHR$^1$ in the presence of heat, wherein R$^1$ is as defined above, thereby producing a fourth compound of formula (X):

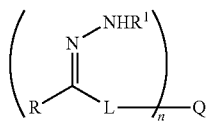

wherein Q, L, R, $R^1$ and n are as defined above; and (c) converting the N—$NHR^1$ groups of said fourth compound, by oxidation or elimination, into diazo groups, thereby producing said diazo-functionalised compound of formula (IIa).

Typically, in the disclosed process for producing a functionalised compound, L' is a group of formula (XI)

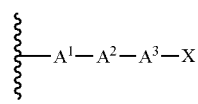

and L is a group of formula (XII)

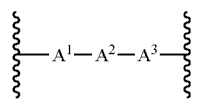

wherein:

$A^1$ is bonded to the carbon atom bonded to R, wherein $A^1$ is a single bond or an unsubstituted or substituted group selected from arylene, heteroarylene, $C_{1-20}$ perfluoroalkylene, *—O—$C_{1-20}$ alkylene, *—O—$C_{1-20}$ perfluoroalkylene, *—O-arylene, *—O-heteroarylene, *—N(R")—$C_{1-20}$ alkylene, *—N(R")—$C_{1-20}$ perfluoroalkylene, *—N(R")-arylene, *—N(R")-heteroarylene, *—S—$C_{1-20}$ alkylene, *—S—$C_{1-20}$ perfluoroalkylene, *—S-arylene, *—S-heteroarylene, *—C(R')$_2$—$C_{1-20}$ alkylene, *—C(R')$_2$—$C_{1-20}$ perfluoroalkylene, *—C(R')$_2$-arylene, *—C(R')$_2$-heteroarylene and $C_{1-20}$ alkylene, wherein each R' is independently selected from a halogen atom, $C_{1-10}$ haloalkyl, $C_{1-10}$ fluoroalkyl, $C_{1-10}$ perfluoroalkyl, aryl, heteroaryl, $C_{3-10}$ carbocyclyl, $C_{3-10}$ heterocyclyl, tri($C_{1-10}$ alkyl)silyl, aryldi($C_{1-10}$ diaryl($C_{1-10}$ alkyl)silyl, triarylsilyl, $C_{2-10}$ alkenyl, $C_{2-10}$ alkynyl and $C_{1-10}$ alkyl, wherein * is the point of attachment of $A^1$ to the carbon atom bonded to R, wherein each of said $C_{1-20}$ alkylene and $C_{1-20}$ perfluoroalkylene groups is optionally interrupted by N(R"), O, S or arylene, and wherein R" is H, $C_{1-6}$ alkyl or aryl;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl;

$A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$;

and, in the group of formula (XI):

X is H, a halo group or a leaving group, provided that when $A^3$ is a single bond, *—$Z^2$-arylene, *—$Z^2$-heteroarylene, *—$Z^2$—$C_{1-20}$ alkylene, arylene, heteroarylene, $C_{1-20}$ alkylene or S(O)$_2$, X is other than H and provided that when $A^3$ is O, S, N(R"), —C(O)O—*, —C(O)N(R")—* or —S(O)$_2$O—*, X is other than a halo group.

In one embodiment of the process for producing a functionalised compound, at least one of the n functional groups of the first compound, Q', is protected and the remaining functional group or groups are unprotected, wherein L' of said second compound of formula (VI) or (VIa) is reactable with said unprotected functional group or groups, to couple the second compound to the first compound, but not with said at least one protected functional group, wherein step (a) of the process comprises:

(i) treating said first compound, Q', with said second compound of formula (VI) or (VIa), thereby coupling the second compound to the first via the unprotected functional group or groups;

(ii) deprotecting said at least one protected functional group; and (iii) treating the resulting compound with a compound of formula (VI) or (VIa), which is the same as or different from the second compound used in step (i), thereby producing said third compound.

The process may be as further defined herein for the process of the invention.

In another broad aspect, disclosed herein is a hydrazone compound of formula (XXX)

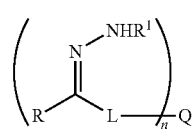

wherein:

n is an integer equal to or greater than 2;

each L, which is the same or different, is a single bond or a linker group;

each R, which is the same or different, is a terminal group;

$R^1$ is H or —S(O)$_2R^2$, wherein $R^2$ is $C_{1-6}$ alkyl, phenyl or naphthyl, which phenyl or naphthyl is unsubstituted or substituted with $C_{1-6}$ alkyl or di($C_{1-6}$ alkyl)amino; and Q is a core moiety, a polymer or a dendrimer.

R, L, Q, n and $R^1$ may be as further defined herein.

In another broad aspect, disclosed herein is a ketone compound of formula (XXXI)

(XXXI)

$$\left( R \underset{}{\overset{O}{\|}} L \right)_n Q$$

wherein:

n is an integer equal to or greater than 2;

each L, which is the same or different, is a single bond or a linker group;

each R, which is the same or different, is a terminal group; and

Q is a core moiety, a polymer or a dendrimer.

R, L, Q and n may be as further defined herein.

In one embodiment, the ketone compound is a compound of formula (XXXII)

(XXXII)

$$R \underset{}{\overset{O}{\|}} A^1 - A^2 - O \underset{Z^1}{\overset{N}{\underset{N}{\bigcirc}}} Z^1$$

wherein

R is a terminal group;

$A^1$ is a single bond or an unsubstituted or substituted group selected from arylene, heteroarylene, $C_{1-20}$ perfluoroalkylene, *—O—$C_{1-20}$ alkylene, *—O—$C_{1-20}$ perfluoroalkylene, *—O-arylene, *—O-heteroarylene, *—N(R")—$C_{1-20}$ alkylene, *—N(R")—$C_{1-20}$ perfluoroalkylene, *—N(R")-arylene, *—N(R")-heteroarylene, *—S—$C_{1-20}$ alkylene, *—S—$C_{1-20}$ perfluoroalkylene, *—S-arylene, *—S-heteroarylene, *—C(R')$_2$—$C_{1-20}$ alkylene, *—C(R')$_2$—$C_{1-20}$ perfluoroalkylene, *—C(R')$_2$-arylene, *—C(R')$_2$-heteroarylene and $C_{1-20}$ alkylene, wherein each R' is independently from a halogen atom, $C_{1-10}$ haloalkyl, $C_{1-10}$ fluoroalkyl, $C_{1-10}$ perfluoroalkyl, aryl, heteroaryl, $C_{3-10}$ carbocyclyl, $C_{3-10}$ heterocyclyl, tri($C_{1-10}$ alkyl)silyl, aryldi($C_{1-10}$ alkyl)silyl, diaryl($C_{1-10}$ alkyl)silyl, triarylsilyl, $C_{2-10}$ alkenyl, $C_{2-10}$ alkynyl and $C_{1-10}$ alkyl, wherein * is the point of attachment of $A^1$ to the carbonyl carbon atom bonded to R, wherein each of said $C_{1-20}$ alkylene and $C_{1-20}$ perfluoroalkylene groups is optionally interrupted by N(R"), O, S or arylene, and wherein R" is H, $C_{1-6}$ alkyl or aryl;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and each $Z^1$ is a halo group.

In one embodiment, the ketone compound is of formula (XXXII), and R, $A^1$ and $A^2$ are as further defined hereinbefore. Typically, both $Z^1$ groups are chloro, bromo or iodo groups. More typically, both $Z^1$ groups are chloro groups.

In one embodiment the ketone compound has the following formula:

The invention is further described in the following Examples:

EXAMPLES

Example 1

Synthesis of Chemical Agents Capable of 3-D Network Formation

Route 1

Synthesis of Triazine Linked Diazomethane Locust Bean Gum, with Reference to FIG. 1

Synthesis of 4-methyl-4'-nitrobenzophenone (1)

4-Nitrobenzoyl chloride (5.00 g, 26.0 mmol, 1 eq) was suspended in toluene (10 mL) and the cloudy yellow mixture was cooled to 0° C. in an ice/water bath. Aluminium trichloride (4.50 g, 33.7 mmol, 1.25 eq) was added portionwise over a period of 20 min and the mixture was allowed to warm to room temperature. After stirring at room temperature for 2 hr HPLC indicated that the starting material had been consumed. The reaction was quenched by pouring onto an ice/1 M HCl solution where the product precipitated out as a yellow solid. The aqueous mixture was extracted with ethyl acetate (3×50 mL). The organic washings were dried over magnesium sulfate and concentrated under reduced pressure to give a yellow solid. The yellow solid was recrystallised from 2-propanol to give 4-methyl-4'-nitrobenzophenone (4.05 g, 62% yield) as a yellow crystalline solid.

Synthesis of 4-bromomethyl-4'-nitrobenzophenone (2)

4-Methyl-4'nitrobenzophenone (46.80 g, 194.0 mmol, 1 eq) was dissolved in chloroform (400 mL) giving a pale yellow solution. N-Bromosuccinimide (69.10 g, 388.0 mmol, 2.0 eq) was then added portionwise over 5 min turning the solution cloudy. The mixture was heated to reflux and stirred for 7 hr and allowed to cool. The mixture was left to stand for 18 hr and then heated under reflux for a further 3 hr. After this time HPLC indicated that most of the starting material had been consumed and the 4-dibromomethyl-4'-nitrobenzophenone was forming as a side product. The reaction mixture was cooled, washed with saturated sodium thiosulfate solution (2×200 mL) and dried over magnesium sulfate. The solution was concentrated under reduced pressure to give a beige solid. The solid was recrystallised from 30% petroleum ether/ethyl acetate to give 4-bromomethyl-4'-nitrobenzophenone (26.25 g, 42%)

Synthesis of 4-hydroxymethyl-4'-nitrobenzophenone (3)

4-bromomethyl-4'-nitrobenzophenone (3.20 g, 10.0 mmol, 1 eq) was dissolved in a 2:1 acetonitrile/water mixture (300 mL) and calcium carbonate (3.00 g, 30.0 mmol, 3 eq) was added. The turbid mixture was stirred under reflux for 60 hr. After this time the reaction mixture was allowed to cool and the solid calcium carbonate was filtered off. The solid was washed with ethyl acetate (10 mL) and the filtrate was concentrated under reduced pressure to give an off-white solid. The solid was dissolved in ethyl acetate and washed with concentrated hydrochloric acid. The organic solution was then neutralised with sodium bicarbonate, dried over magnesium sulfate and concentrated under reduced pressure to give 4-hydroxymethyl-4'-nitrobenzophenone (2.08 g, 81%) as a beige solid.

Synthesis of 4-di(ethyleneglycol)benzyl ether-4'-nitrobenzophenone (4)

4-Hydroxymethyl-4'-nitrobenzophenone (3.00 g, 11.7 mmol, 1 eq) was dissolved in THF (45 mL) and the yellow solution was cooled to 0° C. in an ice/water bath. The sodium hydride (0.70 g, 17.5 mmol, 1.5 eq, 60% dispersion) was added portionwise other 10 min turning the solution a dark blue/black colour. The mixture was warmed to room temperature and stirred for 30 min. The mixture was cooled to 0° C. and 2-(2-chloroethoxy)ethanol (1.48 mL, 14.0 mmol, 1.2 eq) was added dropwise over 5 min turning the solution a dark orange colour. The orange mixture was then allowed to warm to room temperature and stirred for a further 18 h. After this time the reaction was quenched with a small amount of water and the mixture was concentrated under reduced pressure to give an orange oil. The product was used in the next step without further purification due to the difficult work up involved with molecules such as this which exhibit surfactant properties.

Attachment of cyanuric chloride to 4-di(ethyleneglycol)benzyl ether-4'-nitrobenzophenone (5)

Cyanuric chloride (0.42 g, 2.3 mmol, 1.5 eq) and Hünig's base (0.63 mL, 2.3 mmol, 1.5 eq) were dissolved in tetrahydrofuran (20 mL) and the colourless solution was cooled to 0° C. A solution of 4-di(ethyleneglycol)benzyl ether-4'-nitrobenzophenone (0.50 g, 1.5 mmol, 1 eq) in tetrahydrofuran (5 mL) was added dropwise over 5 min to give an orange turbid mixture. The mixture was then allowed to warm to room temperature and stirred for 18 h. At this point HPLC showed that the starting material had been consumed and so the precipitate was filtered off. The filtrate was concentrated under reduced pressure to give an orange oil which was used in the next stage without further purification.

Coupling of triazine-linked 4-di(ethyleneglycol)benzyl ether-4'-nitrobenzophenone to Locust bean gum (6)

The triazine-linked 4-di(ethyleneglycol)benzyl ether-4'-nitrobenzophenone (0.74 g, 1.5 mmol, 500 eq) was dissolved in tetrahydrofuran (20 mL) and Hünig's base (0.32 mL, 1.8 mmol, 600 eq) was added to give an orange solution. Locust bean gum (1.00 g, 3 μmol, 1 eq) was added in one portion and the turbid mixture was heated to 50° C. The mixture was then stirred for 24 hr at which point HPLC indicated that there was no more starting material present in the reaction mixture. The reaction was cooled and filtered to yield an orange solid. The solid was washed with THF, dried and used in the next stage without further purification.

Formation of Tosyl Hydrazone from the Locust Bean Gum-Triazine Attached Nitrobenzophenone (7)

The Locust bean gum-attached nitrobenzophenone (1.70 g, 1.5 mmol, 1 eq) was suspended in methanol (20 mL) and tosyl hydrazide (0.70 g, 3.8 mmol, 2.5 eq) was added portionwise over 2 min. The suspension was then heated to reflux for 24 hr and then allowed to cool to yield the product.

Route 2

Figure 2:
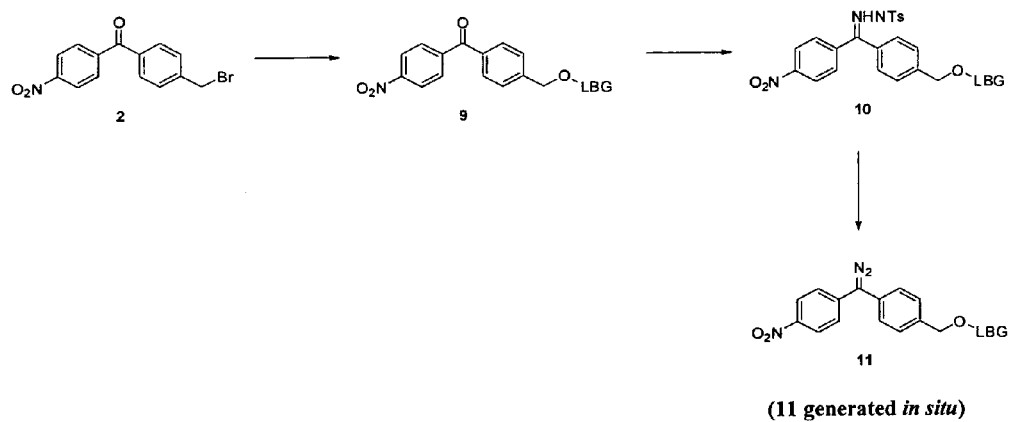
FIG. 2 is a schematic representation of the synthesis of ether linked diazomethane locust bean gum.

Synthesis of Ether Linked Diazomethane Locust Bean Gum, with Reference to FIG. 2

Attachment of Locust Bean Gum to 4-bromomethyl-4'-nitro-benzophenone (9)

Locust bean gum (1.00 g, 3 μmol, 1 eq) was suspended in THF (20 mL) and the beige suspension was cooled to 0° C. Sodium hydride (0.05 g, 3.12 mmol, 106.0 eq, 60% dispersion) was added portionwise over 5 mins to give a brown suspension. The suspension was allowed to warm to room temperature and stirred for 10 mins. The suspension was then cooled again to 0° C. and 4-bromomethyl-4'-nitro-benzophenone (1.00 g, 3.12 mmol, 105.8 eq) was added slowly over 30 mins. The mixture was then allowed to warm to room temperature and stirred for 18 hr. The reaction was quenched carefully with water (0.5 mL) and the dark brown solid was filtered from the mixture. The solid was washed with methanol and dried in air to give a fine brown solid (2 g). This compound was then used in the next step without further purification.

Formation of Tosyl Hydrazone from Ether Attached Locust Bean Gum Benzophenone (10)

The benzophenone (2.00 g, 3.12 mmol, 1 eq) and tosyl hydrazide (1.45 g, 7.80 mmol, 2.5 eq) were mixed in methanol (15 mL) to give a beige suspension. The suspension was heated to reflux for 18 hr and then allowed to cool. The suspension was then filtered and used directly in the next step.

Figure 4:
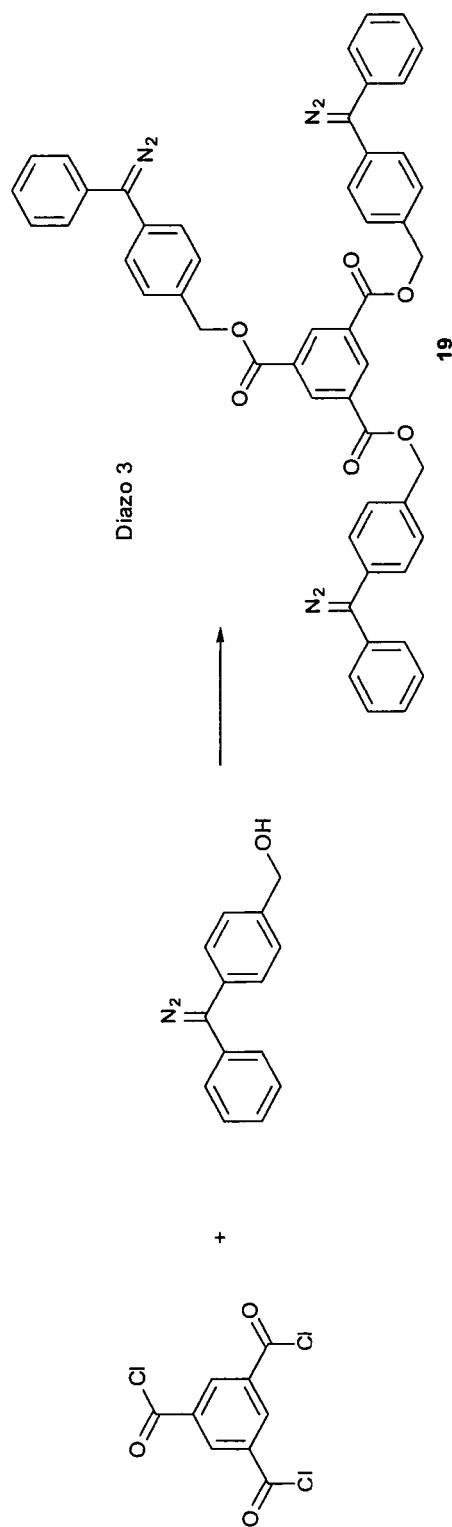
FIG. 4 is a schematic representation of the synthesis of tris(4-methyl diaryldiazomethane) 1,3,5-benzene triester.

Synthesis of tris(4-methyl diaryldiazomethane) 1,3,5-benzene triester (19), with reference to FIG. 4

A solution of 1,3,5 benzene tricarbonyl trichloride 1 (2.33 g, 8.8=101) in DCM (10 mL) was cooled to 0° C. in an ice bath. DMAP (cat. 54 mg, 0.4 mmol) and triethylamine (12.2 mL, 88 mmol) were added to the solution and allowed to cool. Then hydroxymethyl benzophenone diazo 2 (6 g, 26 mmol) in DCM (40 mL) was added and stirring maintained as the mixture warmed to room temperature. After 4 hours there was no starting material left by TLC and the reaction was worked up by diluting with DCM (60 mL) and partitioning between DCM and brine. The combined organic layer (200 mL) was dried with MgSO$_4$ filtered and concentrated in vacuo to yield 3 (7.99 g, quant.) as a red solid; $v_{max}$ (thin film) 2010, 1720, 1220 cm$^{-1}$.

Figure 5:
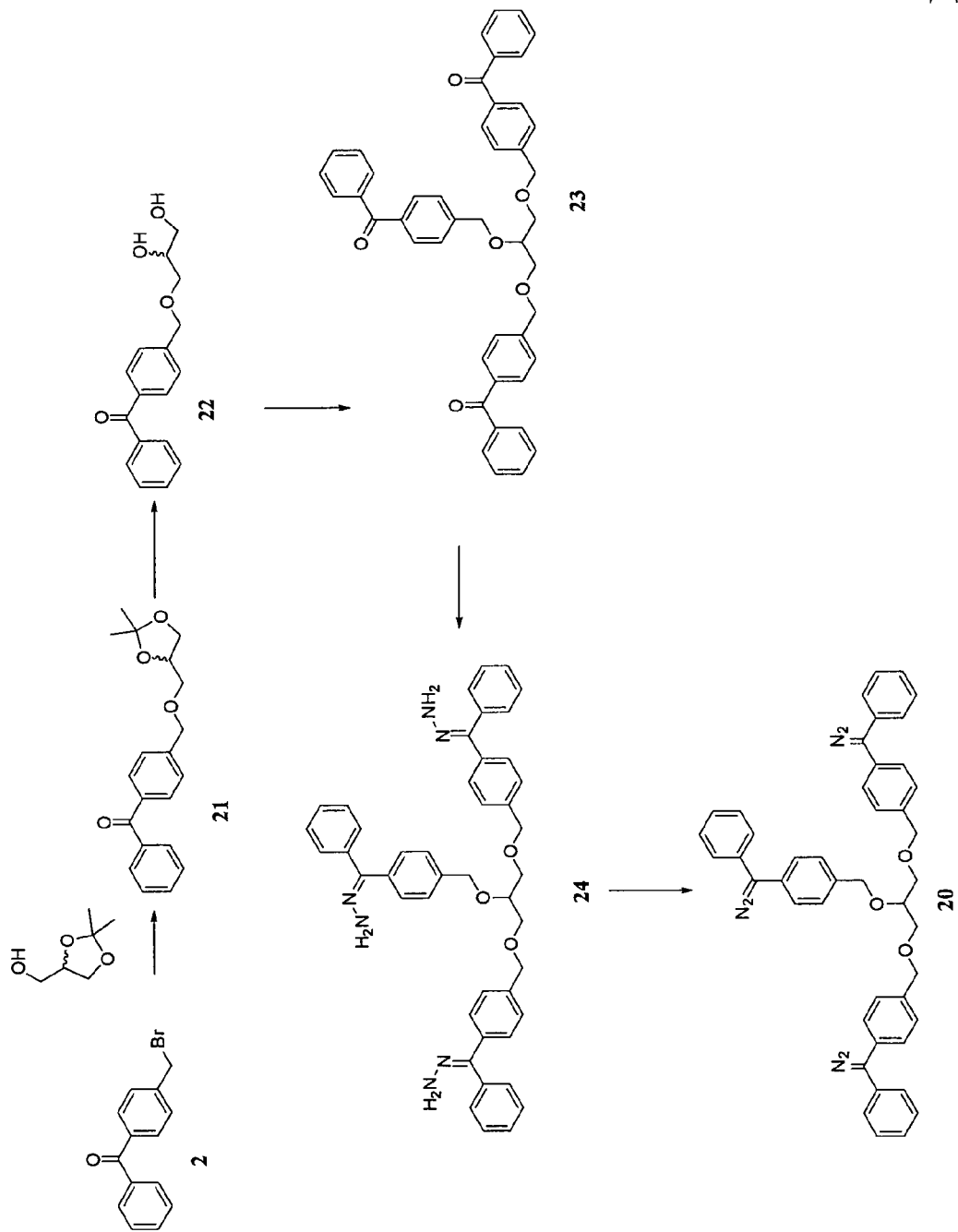
FIG. 5 is a schematic representation of the synthesis of 1,2,3-tri-O-(4-hydroxymethyl diaryl diazomethane-D,L-glyceryl ether.

Synthesis of 1,2,3-tri-O-(4-hydroxymethyl diaryl diazomethane-D,L-glyceryl ether (20), with reference to FIG. 5

Synthesis of 4-(1',2'-O-isopropylidene-D,L-glyceryl)-methylbenzophenone (21)

To a solution of 1,2-O-isopropylidene-D,L-glycerol (1.0 eq) in THF (1 ml/mmol) at 0° C. was added sodium hydride (60% dispersion, 1.25 eq). The mixture was stirred for 5 mins then quenched with 4-bromomethylbenzophenone 2 (1.0 eq). The mixture was allowed to warm to room temperature, stirred for 4 h, then diluted with water. The THF was removed in vacuo and the residue portioned between ethyl acetate and water. The organic layer was collected and concentrated to yield the product 21 in a quantitative yield.

Synthesis of 4-(D,L-glyceryl)-methylbenzophenone (22)

A mixture of 4-(1',2'-O-isopropylidene-D,L-glyceryl)-methylbenzophenone 21 (1.0 eq) in acetic acid (1 ml/mmol) and water (1 ml/mmol) was heated to 50° C. for 3.5 h after which the solvent was removed in vacuo. The residue was diluted with water and concentrated in vacuo a further 3 times to remove trace acetic acid to afford a 22 (98%) as a colourless oil.

Synthesis of 1,2,3-tri-O-(4-hydroxymethylbenzophenone)-D,L-glyceryl ether (23)

To a solution of 4-hydroxymethylbenzophenone-D,L-glyceryl ether 21 (1.0 eq) in N,N-dimethylformamide (1 ml/mmol) at 0° C. was added sodium hydride (60% dispersion, 2.4 eq). The mixture was stirred for 5 min then quenched with 4-bromomethylbenzophenone 2 (2.0 eq) and allowed to warm to ambient temperature. After 18 h the mixture diluted with water and extracted with methyl tert-butyl ether. The organic extract was washed with water and concentrated to yield 23 (76%) as a colourless oil.

Synthesis of 1,2,3-tri-O-(4-hydroxymethylbenzophenone hydrazone)-D,L-glyceryl ether (24)

To a solution of 1,2,3-tri-O-(4-hydroxymethylbenzophenone)-D,L-glyceryl ether 23 (1.0 eq) in propanol (1 ml/mmol) was added hydrazine monohydrate (12 eq). The mixture was heated to reflux for 18 h the diluted ethyle acetetae and water. The organic phase was collected, washed with water then concentrated to yield the product 24 (98%) as a yellow oil.

Synthesis of 1,2,3-tri-O-(4-hydroxymethyl diaryl diazomethane-D,L-glyceryl ether (20)

To a solution of 1,2,3-tri-O-(4-hydroxymethylbenzophenone hydrazone)-D,L-glyceryl ether 24 (1.0 eq) in tetrahydrofuran (2 ml/mmol) was added sodium sulfate (4 eq), a methanolic solution of potassium hydroxide (1 ml/g, 6 eq) and yellow mercury oxide (3.3 eq). The mixture was stirred for 18 h in the dark before being filtered to a pad of Celite. The filtrate was concentrated in vacuo and the residue dissolved in ethyl acetate and washed with water. The organic layer was collected and concentrated to yield the product 20 (99%) as a dark red oil.

Figure 6:
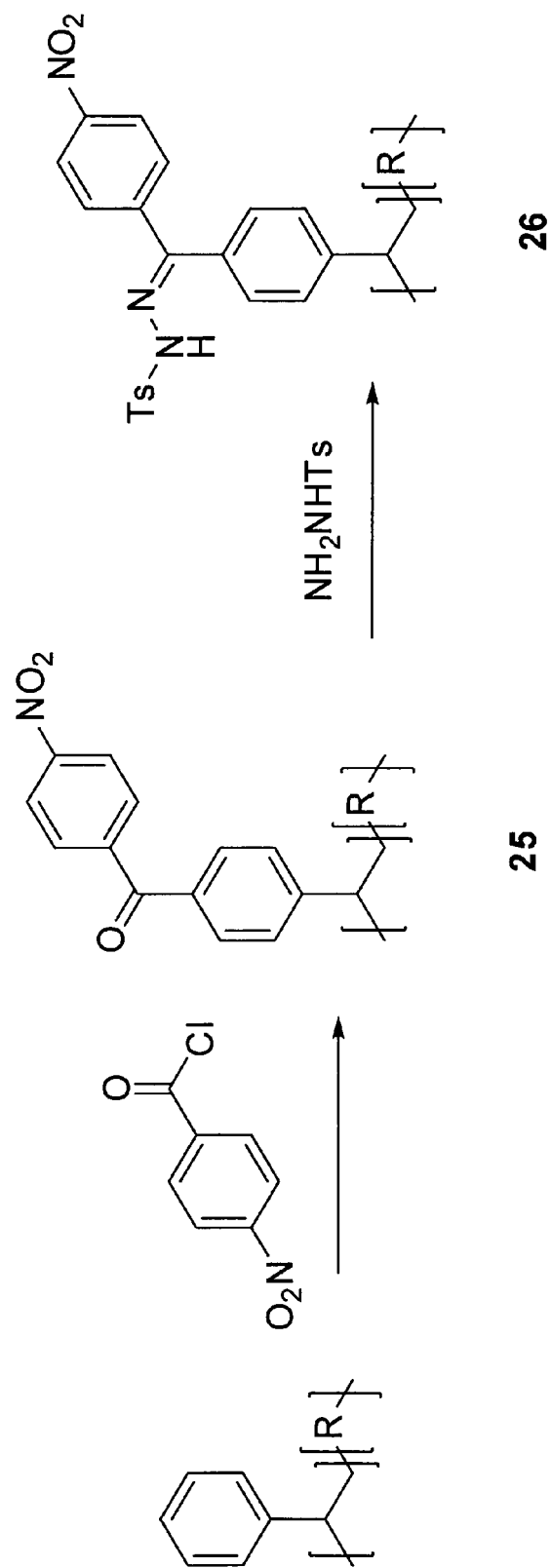
FIG. 6 is a schematic representation of the synthesis of tosyl hydrazone-functionalised polystyrene polymers and copolymers.
Figure 7:
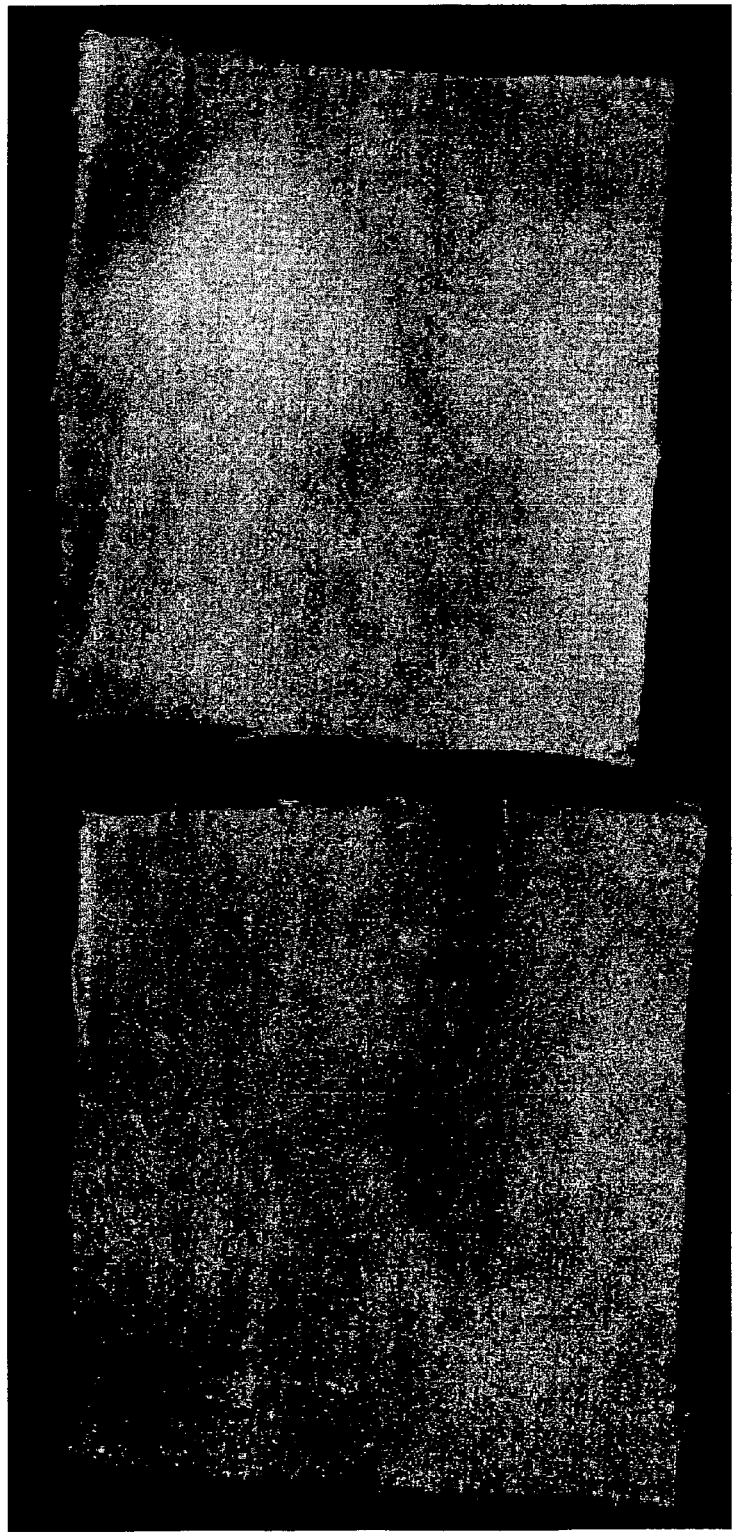
FIG. 7 is a fluorescence image which shows increased deposition of encapsulates onto cotton using the functionalized compound of the invention compared to a control experiment.

General Synthesis of Poly Tosylhydrazones with Reference to FIG. 6

Synthesis of Benzophenone Modified Polymer (25)

A solution of polymer in a suitable solvent (nitroethane, dichloromethane, chloroform) was treated with 4-nitro benzoyl chloride (1 eq) and aluminium chloride (1.2 eq). The solution was stirred at room temperature or at 40° C. then quenched with water. The organic layer was collected and washed with 1M HCl and 1M NaOH solutions sequentially. Concentration of the organic layer yielded the product.

Synthesis of Tosyl Hydrazone Modified Polymer (26)

A suspension of benzophenone polymer (25) in an organic solvent (nitroethane, toluene/methanol or chloroform/methanol) was treated with tosyl hydrazide) and heated to 60-70° C. The mixture was quenched with water and the organic layer washed with 1MCl, collected and evaporated to yield the product (26).

TABLE 1

Overview of modified polymer prepared

| Base polymer | Mw | % of Tosyl hydrazone | Sample Number |
|---|---|---|---|
| Polystyrene | 200 | 70% | 27 |
| Polystyrene | 2000 | 25% | 28 |
| Polystyrene | 60000 | 12.4% | 29 |
| SEBS | >2000 | 2% | 30 |

Example 2

Figure 3:
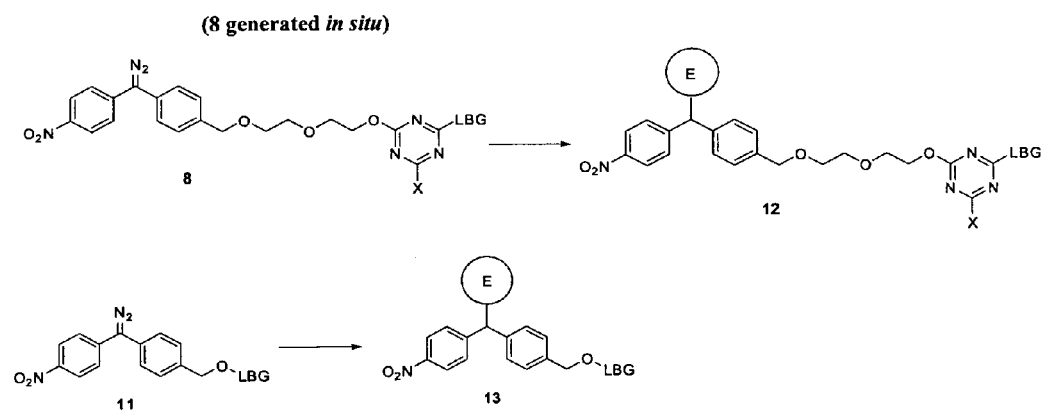
FIG. 3 is a schematic representation of the attachment of triazine- and ether-linked diazomethane locust bean gum compounds to perfume encapsulates.

Attaching Hydrophilic Polymers onto 3-Dimensional Surfaces, with Reference to FIG. 3

Attachment to the LBG to a Fluorescent Particle with Reference to FIG. 3

The functionalised Locust bean gum (100 mg) was suspended in methanol (15 mL) and triethylamine (0.5 mL) was added turning the yellow suspension a bright orange colour. The solvent was then removed under reduced pressure to yield the product (11). The direct linked diazomethane-LBG (11) was mixed with the 10 micron diameter fluorescent particles (1% w/w of polymer with regard to the particle) and sonicated to ensure they were thoroughly mixed. The mixture was heated under reflux for 2 hr Simulated Wash to Show Increased Deposition of Encapsulates onto Cotton Wool The encapsulate suspension was added to a standard basic buffer (30 mL, 0.1 M sodium carbonate/sodium hydrogen carbonate). The mixture was shaken and divided into two vials. Cotton Wool was added to the first vial and the mixture was shaken at 500 rpm for 45 mins to simulate the main wash cycle of a washing machine. The second vial was also shaken at 500 rpm for 45 mins and after this time samples were taken from the vials and the absorbance of the mixture at 400 nm was measured using a Varian UV-vis spectrometer.

TABLE 2

Results of simulated wash, showing increased deposition of encapsulates onto Cotton

| Sample name | % deposition |
|---|---|
| Control | 17 |
| 12 | 32 |

Simulated Wash to Show Increased Deposition of Encapsulates onto Cotton Fabric with Reference to FIG. 9

The encapsulate suspension was added to a standard basic buffer (30 mL, 0.1 M sodium carbonate/sodium hydrogen carbonate). The mixture was shaken and divided into two vials. Cotton Fabric was added to the first vial and the mixture was shaken at 500 rpm for 45 mins to simulate the main wash cycle of a washing machine. The second vial was also shaken at 500 rpm for 45 mins and after this time samples were taken from the analysed using a fluorescent microscope. The fabric sample that had been exposed to modified particle showed considerably more fluorescence then that of the control sample Example 3

Attachment of a Coating to a Surface

Experiment 1

A layer of tris-diazo 19 dissolved in methyl ethyl ketone (3% w/w) was applied to the substrate using a grade 1 K bar and allowed to dry. Then a layer of poly(ethyleneimine) in methanol (50% w/w) was applied using a grade 1 K bar and allowed to dry. The sample was then heat cured in an oven at 120° C. for 10-15 mins.

Experiment 2

A mixture of tris-diazo 19 in methanol (6% w/w) and poly (ethyleneimine) in methanol (200% w/w) where mixed together then applied to the substrate using a grade 1 K bar and allowed to dry. The sample was heat cured in an oven at 120° C. for 10-15 mins.

Experiment 3

A layer of diazo dissolved in methyl ethyl ketone (1% w/w) was applied to the substrate using a grade 1 K bar and allowed to dry. A mixture of tris-diazo 19 in methanol (1% w/w) and poly(ethyleneimine) in methanol (60% w/w) where mixed together then applied to the substrate using a grade 1 K bar and allowed to dry. The sample was heat cured in an oven at 120° C. for 10-15 mins. allowed to dry. The sample was then heat cured in an oven at 120° C. for 10-15 mins.

Experiment 4

A mixture of tris-diazo 20 in methanol (6% w/w) and poly (ethyleneimine) in methanol (200% w/w) where mixed together then applied to the substrate using a grade 1 K bar and allowed to dry. The sample was heat cured in an oven at 120° C. for 10-15 mins.

Experiment 5

A layer of diazo dissolved in methyl ethyl ketone (1% w/w) was applied to the substrate using a grade 1 K bar and allowed to dry. A mixture of tris-diazo 20 in methanol (1% w/w) and poly(ethyleneimine) in methanol (60% w/w) where mixed together then applied to the substrate using a grade 1 K bar and allowed to dry. The sample was heat cured in an oven at 120° C. for 10-15 mins.

TABLE 3

Results of Experiments 1 to 5

| | Substrate | |
|---|---|---|
| | Poly(ethylene terephthalate), Water Contact angle | Biaxial orientated polypropylene, Water Contact angle |
| Untreated | 66° | 72° |
| Experiment 1 | 56° | 23° |
| Experiment 2 | 25° | 26° |
| Experiment 3 | 27° | 25° |
| Experiment 4 | 40° | 39° |
| Experiment 5 | 59° | 50° |

Example 4

Network Formation of Polymers Via Solution Process

Experiment 6

To a solution of polyethylene imine in methyl ethyl ketone was added a sample of chemical agent. The mixture was stirred until a solution was formed then cast onto a PTFE sheet. The resulting film was cured at a 140° C. for 15 mins, cooled then examined.

TABLE 4

Results of Experiments 6

| Chemical Agent | Apperence after cure |
|---|---|
| None | Thick oil |
| 19 | Solid |
| 27 | Solid |
| 28 | Solid |

Example 5

Network Formation of Polymers Coating Via Hot Melt Process

Experiment 7

To a mixture of Elvax 150 (65 eq w/w) and Picolastic A5 (35 eq w/w) was added chemical agent (27) (3 eq w/w) and the sample heated to 100° C. with mixing until a homogenous mixture was obtained. The mixture was cooled and DBU was added (3 eq w/w) slowly. The mixture was warmed to 100° C. then stirred until a homogenous red colour was achieved through out the mixture. The mixture was then heated to 150° C. for XX then cooled. The viscosity of sample was measured using a brookfiled viscometer at 120° c., a shear rate of and a equilibration time of 1 hr.

TABLE 5

Results of Experiments 7

| Chemical Agent | Cure | % Viscosity |
|---|---|---|
| None | Pre Cure | 70 |
| None | Pre Cure | 70 |
| 27 | Post Cure | 70 |
| 27 | Post Cure | >100% |

Experiment 8

To a solution of chemical agent (27) (3 eq w/w) in methanol/MEK was added LiOH (3 eq w/w). The mixture was stirred the concentrated in vacuo to yield a red solid. This red solid was added to a mixture of Elvax 150 (65 eq w/w) and Picolastic A5 (35 eq w/w) and the sample heated to 100° C. with mixing until a homogenous mixture was obtained. The mixture was then heated to 150° C. for XX then cooled. The viscosity of sample was measured using a brookfiled viscometer at 120° c., a shear rate of 0.3 rpm and an equilibration time of 1 hr.

TABLE 5

Results of Experiments 7

| Chemical Agent | Cure | % Viscosity* |
|---|---|---|
| None | Pre Cure | 50-60 |
| None | Pre Cure | 50-60 |
| 27 | Post Cure | 50-60 |
| 27 | Post Cure | >100% |

Example 5

Network Formation Between a Coating and Two Substrates

Experiment 9

Solution Based Processing

To a solution of polymer in toluene (20 wt %) was added triethylamine (5% w/w wrt polymer chemical agent 27 or 19 (5% w/w wrt polymer) and the mixture stirred until a solution was formed. This solution was applied to an FR-4 C stage expoy board using a "k-bar" to achieve a 150 micron wet film thickness. A second sheet of FR4 epoxy resin is the applied to the adhesive and the sandwich is the clamped and heated to 150° C. for 2 h before being allowed to cool for 24 h. The adhesive strength is obtained using a T-Peel configuration. (Table 6)

TABLE 6

Results of Experiments 9

| Chemical Agent | Polymer | T-Peel Strength N/cm |
|---|---|---|
| None | Kraton 1102 | 2.6 |
| 19 | Kraton 1102 | 5.6 |
| 27 | Kraton 1102 | 9.1 |
| None | Kraton 1153 | 2.7 |
| 27 | Kraton 1153 | 7.4 |
| None | Kraton 1184 | 5.7 |
| 27 | Kraton 1184 | 7.7 |
| None | Kraton 1652 | 1.3 |
| 27 | Kraton 1652 | 8.5 |
| None | Kraton 1111 | 3.3 |
| 27 | Kraton 1111 | 4.5 |

Experiment 10

Dry Film Based Processing

To a solution of polymer in toluene (20 wt %) was added triethylamine (5% w/w wrt polymer chemical agent 27 (5% w/w wrt polymer) and the mixture stirred until a solution was formed. This solution was coated onto a PTFE sheet and allowed to dry. The resulting dry film was applied to an FR-4 C stage expoy board. A second sheet of FR4 epoxy resin is the applied to the adhesive and the sandwich is the clamped and heated to 150° C. for 2 h before being allowed to cool for 24 h. The adhesive strength is obtained using a T-Peel configuration. (Table 10)

TABLE 7

Results of Experiments 10

| Chemical Agent | Polymer | T-Peel Strength N/cm |
|---|---|---|
| None | Kraton 1102 | 2.6 |
| 27 | Kraton 1102 | 9.2 |

The invention claimed is:

1. A functionalised compound of formula (II), which functionalised compound comprises carbene precursor groups which are the same or different, wherein n is an integer equal to or greater than 3:

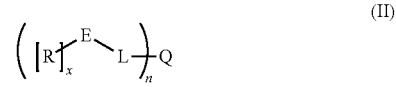

(II)

wherein x is 1, E is a group which is capable of being converted into a carbene reactive intermediate group, Q is a core moiety, a polymer or a dendrimer, and each of the $[R]_x$-E-L- groups, which are the same or different, is independently selected from a group of formula (Ie) and a group of formula (Ia):

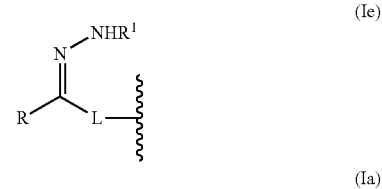

(Ie)

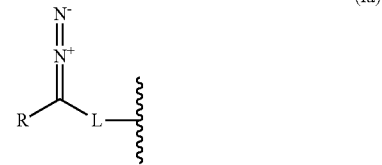

(Ia)

wherein

R is aryl or heteroaryl, which aryl is a monocyclic or bicyclic aromatic group, and which aryl or heteroaryl is unsubstituted or substituted by one or two groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

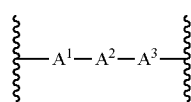
(XII)

wherein:
A$^1$ is bonded to the carbon atom bonded to R, wherein A$^1$ is an unsubstituted or substituted group selected from arylene and heteroarylene;
A$^2$ is a single bond or an unsubstituted or substituted group selected from C$_{1-20}$ alkylene, C$_{1-20}$ perfluoroalkylene, arylene, heteroarylene, *—C$_{1-20}$ alkylene-(O—C$_{1-20}$ alkylene-)$_m$ wherein m is 1 to 20, *—Z$^1$—C$_{1-20}$ alkylene, *—Z$^1$—C$_{1-20}$ perfluoroalkylene, *—Z$^1$-arylene, *—Z$^1$-heteroarylene and *—Z$^1$—C$_{1-20}$ alkylene-(O—C$_{1-20}$ alkylene-)$_m$ wherein m is 1 to 20, wherein Z$^1$ is selected from O, S, C(O), S(O), S(O)$_2$, N(R"), C(O)O, OC(O), C(O)N(R") and N(R")C(O), wherein * is the point of attachment of A$^2$ to A$^1$, wherein each of said C$_{1-20}$ alkylene and C$_{1-20}$ perfluoroalkylene groups is optionally interrupted by N(R"), O, S or arylene, and wherein each R" is independently selected from H, C$_{1-6}$ alkyl and aryl; and
A$^3$ is a single bond or an unsubstituted or substituted group selected from *—Z$^2$-arylene, *—Z$^2$-heteroarylene, *—Z$^2$—C$_{1-20}$ alkylene, arylene, heteroarylene, C$_{1-20}$ alkylene, *—Z$^2$-arylene-O, heteroarylene-O, *—Z$^2$—C$_{1-20}$ alkylene-O, *-arylene-O, *-heteroarylene-O, *—C$_{1-20}$ alkylene-O, C(O), S(O)$_2$, *—OC(O), *—N(R")C(O), O, S, N(R"), *—C(O)O, *—C(O)N(R"), *—S(O)$_2$O, C$_{1-20}$ alkenylene, C$_{1-20}$ alkynylene, *—Z$^2$—C$_{1-20}$ alkenylene and *—Z$^2$—C$_{1-20}$ alkynylene, wherein Z$^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$;
R$^1$ is —S(O)$_2$R$^2$ or H, wherein R$^2$ is an unsubstituted or substituted C$_{1-6}$ alkyl group or an unsubstituted or substituted aryl group;
wherein said core moiety, polymer or dendrimer comprises n linker groups of formula A$^4$, each of which is attached to L, wherein n is an integer equal to or greater than 3;
each A$^4$ is the same or different and is independently selected from a single bond, —Z$^3$-arylene-*, —Z$^3$-heteroarylene-*, —Z$^3$—C$_{1-20}$ alkylene-*, arylene, heteroarylene, C$_{1-20}$ alkylene, —Z$^3$-arylene-O—*, —Z$^3$-heteroarylene-O—*, —Z$^3$—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, C$_{1-20}$ alkenylene, C$_{1-20}$ alkynylene, —Z$^3$—C$_{1-20}$ alkenylene-* and —Z$^3$—C$_{1-20}$ alkynylene-*, wherein Z$^3$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^4$ to L;
said core moiety is a straight-chained or branched, saturated or unsaturated C$_{1-20}$ hydrocarbon moiety; an aryl ring; a heteroaryl ring; a C$_{5-10}$ carbocyclic ring; a C$_{5-10}$ heterocyclic ring; or a fused bi-, tri- or tetracyclic ring system wherein each ring of said fused bi-, tri- or tetracyclic ring system is independently selected from an aryl ring, a heteroaryl ring, a C$_{5-10}$ carbocyclic ring and a C$_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n linker groups, A$^4$, and is or is not substituted with one or more groups other than said n linker groups, A$^4$; and
said dendrimer is (a) a poly(amidoamine) (PAMAM) dendrimer or (b) a dendrimer which comprises from 50 to 500 surface groups which are linker groups of formula A$^4$;
with the proviso that when none of the [R]$_x$-E-L- groups is a group of formula (Ie) in which R$^1$ is —S(O)$_2$R$^2$, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

2. The functionalised compound according to claim 1 which is a hydrazone compound of formula (XXX)

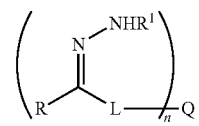
(XXX)

wherein:
n is an integer equal to or greater than 3;
R is aryl or heteroaryl, which aryl is a monocyclic or bicyclic aromatic group, and which aryl or heteroaryl is unsubstituted or substituted by one or two groups, which groups are the same or different and are independently selected from C$_{1-20}$ alkyl, C$_{2-20}$ alkenyl, C$_{2-20}$ alkynyl, C$_{1-20}$ haloalkyl, C$_{1-20}$ fluoroalkyl, C$_{1-20}$ perfluoroalkyl, aryl, cyano, nitro, hydroxy, halo, carboxy, amino, C$_{1-10}$ alkylamino, di(C$_{1-10}$)alkylamino, arylamino, diarylamino, arylalkylamino, amido, acyl, acyloxy, acylamido, ester, C$_{1-10}$ alkoxy, aryloxy, haloalkyl, thiol, C$_{1-10}$ alkylthio, arylthio, sulfonic acid, sulfonyl, sulfonamide, tri(C$_{1-20}$ alkyl)silyl, aryldi(C$_{1-20}$ alkyl)silyl, diaryl(C$_{1-20}$ alkyl)silyl and triarylsilyl;
each L, which is the same or different, is a single bond or a group of formula (XII)

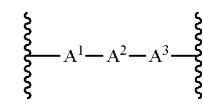
(XII)

wherein:
A$^1$ is bonded to the carbon atom bonded to R, wherein A$^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^3$ to $A^2$;

$R^1$ is H or —S(O)$_2R^2$, wherein $R^2$ is an unsubstituted or substituted $C_{1-6}$ alkyl group or an unsubstituted or substituted aryl group;

Q is a core moiety, a polymer or a dendrimer, which core moiety, polymer or dendrimer comprises n linker groups of formula $A^4$, each of which is attached to L, wherein n is an integer equal to or greater than 3;

each $A^4$ is the same or different and is independently selected from a single bond, —$Z^3$-arylene-*, —$Z^3$-heteroarylene-*, —$Z^3$—$C_{1-20}$ alkylene-*, arylene, heteroarylene, $C_{1-20}$ alkylene, —$Z^3$-arylene-O—*, —$Z^3$-heteroarylene-O—*, —$Z^3$—$C_{1-20}$ alkylene-O—*, arylene-O—*, heteroarylene-O—*, $C_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, $C_{1-20}$ alkenylene, $C_{1-20}$ alkynylene, —$Z^3$—$C_{1-20}$ alkenylene-* and —$Z^3$—$C_{1-20}$ alkynylene-*, wherein $Z^3$ is selected from O, S, N(R"), C(O), S(O), S(O)$_2$, C(O)O, OC(O), C(O)N(R") and N(R")C(O), wherein each R" is independently selected from H, $C_{1-6}$ alkyl and aryl, and wherein * is the point of attachment of $A^4$ to L;

said core moiety is a straight-chained or branched, saturated or unsaturated $C_{1-20}$ hydrocarbon moiety; an aryl ring; a heteroaryl ring; a $C_{5-10}$ carbocyclic ring; a $C_{5-10}$ heterocyclic ring; or a fused bi-, tri- or tetracyclic ring system wherein each ring of said fused bi-, tri- or tetracyclic ring system is independently selected from an aryl ring, a heteroaryl ring, a $C_{5-10}$ carbocyclic ring and a $C_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n linker groups, $A^4$, and is or is not substituted with one or more groups other than said n linker groups, $A^4$; and said dendrimer is (a) a poly(amidoamine) (PAMAM) dendrimer or (b) a dendrimer which comprises from 50 to 500 surface groups which are linker groups of formula $A^4$;

with the proviso that when $R^1$ is H, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof.

3. The functionalised compound according to claim 1 which is a sulfonylhydrazone compound of formula (XXXa)

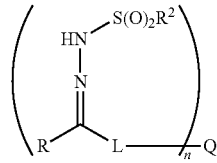

(XXXa)

wherein:
n is an integer equal to or greater than 3;
R is aryl or heteroaryl, which aryl is a monocyclic or bicyclic aromatic group, and which aryl or heteroaryl is unsubstituted or substituted by one or two groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl;

each L, which is the same or different, is a single bond or a group of formula (XII)

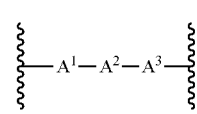

(XII)

wherein:
$A^1$ is bonded to the carbon atom bonded to R, wherein $A^1$ is an unsubstituted or substituted group selected from arylene and heteroarylene;

$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and $A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—Z²-arylene-O, *—Z²-heteroarylene-O, *—Z²—C$_{1-20}$ alkylene-O, *-arylene-O, *-heteroarylene-O, *—C$_{1-20}$ alkylene-O, C(O), S(O)$_2$, *—OC(O), *—N(R")C(O), O, S, N(R"), *—C(O)O, *—C(O)N(R"), *—S(O)$_2$O, C$_{1-20}$ alkenylene, C$_{1-20}$ alkynylene, *—Z²—C$_{1-20}$ alkenylene and *—Z²—C$_{1-20}$ alkynylene, wherein Z² is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A³ to A²;

R² is an unsubstituted or substituted C$_{1-6}$ alkyl group or an unsubstituted or substituted aryl group;

Q is a core moiety, a polymer or a dendrimer, which core moiety, polymer or dendrimer comprises n linker groups of formula A⁴, each of which is attached to L, wherein n is an integer equal to or greater than 3;

each A⁴ is the same or different and is independently selected from a single bond, —Z³-arylene-*, —Z³-heteroarylene-*, —Z³—C$_{1-20}$ alkylene-*, arylene, heteroarylene, C$_{1-20}$ alkylene, —Z³-arylene-O—*, —Z³-heteroarylene-O—*, —Z³—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, C$_{1-20}$ alkenylene, C$_{1-20}$ alkynylene, —Z³—C$_{1-20}$ alkenylene-* and —Z³—C$_{1-20}$ alkynylene-*, wherein Z³ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A⁴ to L;

said core moiety is a straight-chained or branched, saturated or unsaturated C$_{1-20}$ hydrocarbon moiety; an aryl ring; a heteroaryl ring; a C$_{5-10}$ carbocyclic ring; a C$_{5-10}$ heterocyclic ring; or a fused bi-, tri- or tetracyclic ring system wherein each ring of said fused bi-, tri- or tetracyclic ring system is independently selected from an aryl ring, a heteroaryl ring, a C$_{5-10}$ carbocyclic ring and a C$_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n linker groups, A⁴, and is or is not substituted with one or more groups other than said n linker groups, A⁴; and said dendrimer is (a) a poly(amidoamine) (PAMAM) dendrimer or (b) a dendrimer which comprises from 50 to 500 surface groups which are linker groups of formula A⁴.

4. The functionalised compound according to claim 1 wherein L is a single bond, and Q comprises at least n aryl or heteroaryl rings, wherein n is an integer equal to or greater than 3, wherein each L which is single bond is attached directly to said aryl or heteroaryl ring, thereby bonding the aryl or heteroaryl ring directly to the carbon atom of E which is bonded to R.

5. The functionalised compound according to claim 1 wherein:

(a) Q comprises polystyrene, a copolymer comprising polystyrene, a thermoplastic elastomer, polyisoprene, a copolymer comprising polyisoprene, SBS rubber, SIS rubber or poly(styrene)-poly(ethylene/butylene)-poly(styrene) (SEBS); or (b) Q is a core moiety of formula (XIV), which core moiety comprises n linker groups of formula A⁴, each of which is attached to L, wherein n is an integer from 3 to 10:

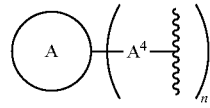

(XIV)

wherein each A⁴ is the same or different and is independently selected from a single bond, —Z³-arylene-*, —Z³-heteroarylene-*, —Z³—C$_{1-20}$ alkylene-*, arylene, heteroarylene, C$_{1-20}$ alkylene, —Z³-arylene-O—*, —Z³-heteroarylene-O—*, —Z³—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, C$_{1-20}$ alkenylene, C$_{1-20}$ alkynylene, —Z³—C$_{1-20}$ alkenylene-* and —Z³—C$_{1-20}$ alkynylene-*, wherein Z³ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A⁴ to L, and wherein A is an aryl ring, a heteroaryl ring, a C$_{5-10}$ carbocyclic ring, a C$_{5-10}$ heterocyclic ring, or a fused bi-, tri- or tetracyclic ring system wherein each ring of said fused bi-, tri- or tetracyclic ring system is independently selected from an aryl ring, a heteroaryl ring, a C$_{5-10}$ carbocyclic ring and a C$_{5-10}$ heterocyclic ring; or (c) Q is a core moiety of formula (XVI), which core moiety comprises n linker groups of formula A⁴, each of which is attached to L, wherein n is an integer from 3 to 10:

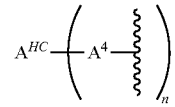

(XVI)

wherein each A⁴ is the same or different and is independently selected from a single bond, —Z³-arylene-*, —Z³-heteroarylene-*, —Z³—C$_{1-20}$ alkylene-*, arylene, heteroarylene, C$_{1-20}$ alkylene, —Z³-arylene-O—*, —Z³-heteroarylene-O—*, —Z³—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O— *, C$_{1-20}$ alkenylene, C$_{1-20}$ alkynylene, —Z³—C$_{1-20}$ alkenylene-* and —Z³—C$_{1-20}$ alkynylene-*, wherein Z³ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A⁴ to L, and wherein A$^{HC}$ is straight-chained or branched, saturated or unsaturated C$_{1-20}$ hydrocarbon moiety which is substituted with said n linker groups, A⁴, and is or is not substituted with one or more groups other than said n linker groups, A⁴.

6. A method for the use of a functionalised compound as defined in claim 1 as an agent for producing a chemically-bound three-dimensional network on or within a substrate, or as a cross linking agent.

7. A process for producing a chemically-bound three-dimensional network on or within a substrate, which process comprises:

(a) contacting a substrate with a functionalised compound as defined in claim 1; and (b) generating carbene reactive intermediate groups from said carbene precursor groups, so that said carbene reactive intermediate groups react with the substrate to produce said chemically-bound three-dimensional network on or within the substrate.

8. A process for producing a chemically-bound three-dimensional network between a first substrate and a second substrate, which process comprises:
(a) contacting a first substrate and a second substrate with a functionalised compound as defined in claim 1; and
(b) generating carbene reactive intermediate groups from said carbene precursor groups, so that said carbene reactive intermediate groups react with the first substrate and the second substrate to produce said chemically-bound three-dimensional network between said first and second substrates.

9. A process for producing a film or a coating, which process comprises:
(a) disposing a film formulation or a coating formulation onto the surface of a substrate, which film or coating formulation comprises a functionalised compound as defined in claim 1; and
(b) generating carbene reactive intermediate groups from said carbene precursor groups, thereby forming a film or a coating on said substrate.

10. A process for producing a treated particle, which process comprises:
(a) contacting a functionalised cross linking compound with a substrate particle, wherein the functionalised cross linking compound is a compound as defined in claim 1; and
(b) generating carbene reactive intermediate groups from said carbene precursor groups, so that a carbene reactive intermediate group reacts with the substrate particle to attach the particle to the compound, thereby yielding said treated particle.

11. A process for cross linking a first substrate to a second substrate, which first and second substrates are the same or different, which process comprises
(a) contacting the first and second substrates with a functionalised cross linking compound, wherein the functionalised cross linking compound is a compound as defined in claim 1; and
(b) generating carbene reactive intermediate groups from said carbene precursor groups, so that at least one carbene reactive intermediate group reacts with the first substrate and at least one other reactive intermediate group reacts with the second substrate, thereby cross linking the first and second substrates.

12. A process for producing a functionalised compound of formula (II), which functionalised compound comprises carbene precursor groups which are the same or different, wherein n is an integer equal to or greater than 3:

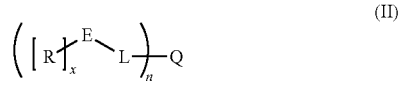

(II)

wherein x is 1, E is a group which is capable of being converted into a carbene reactive intermediate group, Q is a core moiety, a polymer or a dendrimer, and each of the [R]$_x$-E-L- groups, which are the same or different, is independently selected from a group of formula (Ie) and a group of formula (Ia):

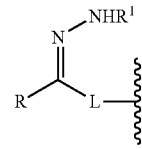

(Ie)

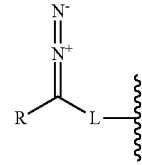

(Ia)

wherein
R is aryl or heteroaryl, which aryl is a monocyclic or bicyclic aromatic group, and which aryl or heteroaryl is unsubstituted or substituted by one or two groups, which groups are the same or different and are independently selected from $C_{1-20}$ alkyl, $C_{2-20}$ alkenyl, $C_{2-20}$ alkynyl, $C_{1-20}$ haloalkyl, $C_{1-20}$ fluoroalkyl, $C_{1-20}$ perfluoroalkyl, aryl, cyano, nitro, hydroxy, halo, carboxy, amino, $C_{1-10}$ alkylamino, di($C_{1-10}$)alkylamino, arylamino, diarylamino, arylalkylamino, amido, acyl, acyloxy, acylamido, ester, $C_{1-10}$ alkoxy, aryloxy, haloalkyl, thiol, $C_{1-10}$ alkylthio, arylthio, sulfonic acid, sulfonyl, sulfonamide, tri($C_{1-20}$ alkyl)silyl, aryldi($C_{1-20}$ alkyl)silyl, diaryl($C_{1-20}$ alkyl)silyl and triarylsilyl; each L, which is the same or different, is a single bond or a group of formula (XII)

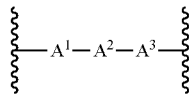

(XII)

wherein:
$A^1$ is bonded to the carbon atom bonded to R, wherein $A^1$ is an unsubstituted or substituted group selected from arylene and heteroarylene;
$A^2$ is a single bond or an unsubstituted or substituted group selected from $C_{1-20}$ alkylene, $C_{1-20}$ perfluoroalkylene, arylene, heteroarylene, *—$C_{1-20}$ alkylene-(O—$C_{1-20}$ alkylene-)$_m$ wherein m is 1 to 20, *—$Z^1$—$C_{1-20}$ alkylene, *—$Z^1$—$C_{1-20}$ perfluoroalkylene, *—$Z^1$-arylene, *—$Z^1$-heteroarylene and *—$Z^1$—$C_{1-20}$ alkylene-(O—$C_{1-20}$ alkylene-)$_m$ wherein m is 1 to 20, wherein $Z^1$ is selected from O, S, C(O), S(O), S(O)$_2$, N(R"), C(O)O, OC(O), C(O)N(R") and N(R")C(O), wherein * is the point of attachment of $A^2$ to $A^1$, wherein each of said $C_{1-20}$ alkylene and $C_{1-20}$ perfluoroalkylene groups is optionally interrupted by N(R"), O, S or arylene, and wherein each R" is independently selected from H, $C_{1-6}$ alkyl and aryl; and
$A^3$ is a single bond or an unsubstituted or substituted group selected from *—$Z^2$-arylene, *—$Z^2$-heteroarylene, *—$Z^2$—$C_{1-20}$ alkylene, arylene, heteroarylene, $C_{1-20}$ alkylene, *—$Z^2$-arylene-O, *—$Z^2$-heteroarylene-O, *—$Z^2$—$C_{1-20}$ alkylene-O, *-arylene-O, *-heteroarylene-O, *—$C_{1-20}$ alkylene-O, C(O), S(O)$_2$, *—OC(O), *—N(R")C(O), O, S, N(R"), *—C(O)O, *—C(O)N(R"), *—S(O)$_2$O, $C_{1-20}$ alkenylene, $C_{1-20}$ alkynylene, *—$Z^2$—$C_{1-20}$ alkenylene and *—$Z^2$—$C_{1-20}$ alkynylene, wherein $Z^2$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^3$ to A$^2$;

R$^1$ is —S(O)$_2$R$^2$ or H, wherein R$^2$ is an unsubstituted or substituted C$_{1-6}$ alkyl group or an unsubstituted or substituted aryl group;

wherein said core moiety, polymer or dendrimer comprises n linker groups of formula A$^4$, each of which is attached to L, wherein n is an integer equal to or greater than 3, each A$^4$ is the same or different and is independently selected from a single bond, —Z$^3$-arylene-*, —Z$^3$-heteroarylene-*, —Z$^3$—C$_{1-20}$ alkylene-*, arylene, heteroarylene, C$_{1-20}$ alkylene, —Z$^3$-arylene-O—*, —Z$^3$-heteroarylene-O—*, —Z$^3$—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, C$_{1-20}$ alkenylene, C$_{1-20}$ alkynylene, —Z$^3$—C$_{1-20}$ alkenylene-* and —Z$^3$—C$_{1-20}$ alkynylene-*, wherein Z$^3$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^4$ to L;

said core moiety is a straight-chained or branched, saturated or unsaturated C$_{1-20}$ hydrocarbon moiety; an aryl ring; a heteroaryl ring; a C$_{5-10}$ carbocyclic ring; a C$_{5-10}$ heterocyclic ring; or a fused bi-, tri- or tetracyclic ring system wherein each ring of said fused bi-, tri- or tetracyclic ring system is independently selected from an aryl ring, a heteroaryl ring, a C$_{5-10}$ carbocyclic ring and a C$_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n linker groups, A$^4$, and is or is not substituted with one or more groups other than said n linker groups, A$^4$; and said dendrimer is (a) a poly(amidoamine) (PAMAM) dendrimer or (b) a dendrimer which comprises from 50 to 500 surface groups which are linker groups of formula A$^4$;

with the proviso that when none of the [R]$_x$-E-L- groups is a group of formula (Ie) in which R$^1$ is —S(O)$_2$R$^2$, then:
each L is a group of formula (XII); and
Q is a core moiety, a dendrimer, or a polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof;

which process comprises:
(a) treating a first compound, Q', which is a core moiety, a polymer or a dendrimer and which bears n functional groups, wherein n is an integer equal to or greater than 3, with at least one second compound of formula (VIa)

(VIa)

wherein:
L' is a leaving group or a reactive precursor to said group of formula (XII), wherein L' is reactable with a said functional group to couple the second compound to the first compound, R is aryl or heteroaryl, which aryl is a monocyclic or bicyclic aromatic group, and which aryl or heteroaryl is unsubstituted or substituted by one or two groups, which groups are the same or different and are independently selected from C$_{1-20}$ alkyl, C$_{2-20}$ alkenyl, C$_{2-20}$ alkynyl, C$_{1-20}$ haloalkyl, C$_{1-20}$ fluoroalkyl, C$_{1-20}$ perfluoroalkyl, aryl, cyano, nitro, hydroxy, halo, carboxy, amino, C$_{1-10}$ alkylamino, di(C$_{1-10}$)alkylamino, arylamino, diarylamino, arylalkylamino, amido, acyl, acyloxy, acylamido, ester, C$_{1-10}$ alkoxy, aryloxy, haloalkyl, thiol, C$_{1-10}$ alkylthio, arylthio, sulfonic acid, sulfonyl, sulfonamide, tri(C$_{1-20}$ alkyl)silyl, aryldi(C$_{1-20}$ alkyl)silyl, diaryl(C$_{1-20}$ alkyl)silyl and triarylsilyl, Y is N=N, O or N—NHR$^1$, wherein R$^1$ is H or —S(O)$_2$R$^2$ and wherein R$^2$ is an unsubstituted or substituted C$_{1-6}$ alkyl group or an unsubstituted or substituted aryl group, the n functional groups of said first compound Q' are groups of formula -A$^4$-X$^2$, wherein each A$^4$ is the same or different and is independently selected from a single bond, —Z$^3$-arylene-*, —Z$^3$-heteroarylene-*, —Z$^3$—C$_{1-20}$ alkylene-*, arylene, heteroarylene, C$_{1-20}$ alkylene, —Z$^3$-arylene-O—*, —Z$^3$-heteroarylene-O—*, —Z$^3$—C$_{1-20}$ alkylene-O—*, arylene-O—*, heteroarylene-O—*, C$_{1-20}$ alkylene-O—*, —C(O)—*, S(O)$_2$, —OC(O)—*, —N(R")C(O)—*, O, S, N(R"), —C(O)O—*, —C(O)N(R")—*, —S(O)$_2$O—*, C$_{1-20}$ alkenylene, C$_{1-20}$ alkynylene, —Z$^3$—C$_{1-20}$ alkenylene-* and —Z$^3$—C$_{1-20}$ alkynylene-*, wherein Z$^3$ is selected from O, S, N(R"), C(O), S(O), S(O)$_2$, C(O)O, OC(O), C(O)N(R") and N(R")C(O), wherein each R" is independently selected from H, C$_{1-6}$ alkyl and aryl, and wherein * is the point of attachment of A$^4$ to X$^2$, X$^2$ is H, a halo group or a leaving group, provided that when A$^4$ is a single bond, arylene, heteroarylene, C$_{1-20}$ alkylene, —Z$^2$-arylene-*, —Z$^2$-heteroarylene-*, —Z$^2$—C$_{1-20}$ alkylene-* or S(O)$_2$, X$^2$ is other than H and provided that when A$^4$ is O, S, N(R"), —C(O)O—*, —C(O)N(R")—*, —S(O)$_2$O—*, —Z$^3$-arylene-O—*, —Z$^3$-heteroarylene-O—*, —Z$^3$-C$_{1-20}$ alkylene-O—*, arylene-O—*, heteroarylene-O—* or C$_{1-20}$ alkylene-O—*, X$^2$ is other than a halo group, and said core moiety Q' is a straight-chained or branched, saturated or unsaturated C$_{1-20}$ hydrocarbon moiety; an aryl ring; a heteroaryl ring; a C$_{5-10}$ carbocyclic ring; a C$_{5-10}$ heterocyclic ring; or a fused bi-, tri- or tetracyclic ring system wherein each ring of said fused bi-, tri- or tetracyclic ring system is independently selected from an aryl ring, a heteroaryl ring, a C$_{5-10}$ carbocyclic ring and a C$_{5-10}$ heterocyclic ring; wherein said hydrocarbon moiety, aryl ring, heteroaryl ring, carbocyclic ring, heterocyclic ring or fused bi-, tri- or tetracyclic ring system is substituted with said n functional groups, -A$^4$-X$^2$, and is or is not substituted with one or more groups other than said n functional groups, -A$^4$-X$^2$, provided that when none of the [R]$_x$-E-L- groups in the functionalised compound of formula (II) to be produced is a group of formula (Ie) in which R$^1$ is —S(O)$_2$R$^2$, then each L' is a reactive precursor to said group of formula (XII) and Q' is said core moiety, said dendrimer, or said polymer, which polymer comprises: a polysaccharide, a protein, a polyester, a polyether, a polyacrylate, a polymethacrylate, a polycarbonate, polyetheretherketone (PEEK), a polyetherimide, a polyimide, a polysulfone, poly(vinyl chloride), a polysilane, a polysiloxane, a polyurea, a polyurethane, polylactic acid, polyvinylidene chloride, a fluoro-polymer, a polyethylene imine, or a salt thereof; thereby producing a third compound of formula (IXa):

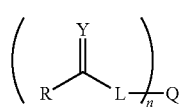

(IXa)

wherein Q, L, R, Y and n are as defined above;
provided that:
when Y is O, the process further comprises:
(b1) treating the third compound with $H_2N$—$NHR^1$ in the presence of heat, wherein $R^1$ is as defined above, thereby producing a fourth compound of formula (X):

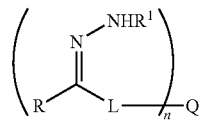

(X)

wherein Q, L, R, $R^1$ and n are as defined above; and, optionally,
(c1) converting some or all of the N—$NHR^1$ groups of said fourth compound into diazo groups, N=N;
and provided that:
when Y is N—$NHR^1$, the process optionally further comprises:
(b2) converting some or all of the Y groups of said third compound into diazo groups; thereby producing said functionalised compound of formula (II).

13. The functionalised compound according to claim 1, wherein Q is a polymer or a core moiety.

14. The functionalised compound according to claim 1, wherein Q is a polymer.

15. The functionalised compound according to claim 3, wherein Q is a polymer or a core moiety.

16. The functionalised compound according to claim 3, wherein Q is a polymer.

* * * * *